United States Patent
Slusarewicz et al.

(10) Patent No.: US 7,309,491 B2
(45) Date of Patent: Dec. 18, 2007

(54) HEAT SHOCK PROTEIN-BASED VACCINES AND IMMUNOTHERAPIES

(75) Inventors: Paul Slusarewicz, San Antonio, TX (US); Jessica Baker Flechtner, Maynard, MA (US); Sunil Mehta, Collegeville, PA (US); Kenya Prince-Cohane, Worcester, MA (US); Sofija Andjelic, Nanuet, NY (US); Brian H. Barber, Toronto (CA)

(73) Assignee: Antigenics Inc., New York, NY (US)

( * ) Notice: Subject to any disclaimer, the term of this patent is extended or adjusted under 35 U.S.C. 154(b) by 0 days.

(21) Appl. No.: 10/820,067

(22) Filed: Apr. 8, 2004

(65) Prior Publication Data

US 2005/0214312 A1 Sep. 29, 2005

Related U.S. Application Data

(60) Provisional application No. 60/503,417, filed on Sep. 16, 2003, provisional application No. 60/463,746, filed on Apr. 18, 2003, provisional application No. 60/462,469, filed on Apr. 11, 2003.

(51) Int. Cl.
*A61K 39/385* (2006.01)
*A61K 39/00* (2006.01)
*A61K 39/29* (2006.01)

(52) U.S. Cl. .............. 424/194.1; 424/196.11; 424/192.1

(58) Field of Classification Search ...... None
See application file for complete search history.

(56) References Cited

U.S. PATENT DOCUMENTS 5,348,945 A 9/1994 Berberian et al.
5,498,538 A 3/1996 Kay et al.
5,541,109 A 7/1996 Searfoss
5,679,352 A 10/1997 Chong et al.
5,750,119 A 5/1998 Srivastava
5,837,251 A 11/1998 Srivastava
5,935,576 A 8/1999 Srivastava
5,961,979 A 10/1999 Srivastava
5,962,262 A 10/1999 Hillman et al.
5,985,270 A 11/1999 Srivastava (Continued)

FOREIGN PATENT DOCUMENTS

| EP | 0 538 952 | 4/1993 |
|---|---|---|
| WO | WO 89/04871 | 6/1989 |
| WO | WO 93/17712 | 9/1993 |
| WO | WO 94/11513 | 5/1994 |
| WO | WO 94/29459 | 12/1994 |

(Continued)

OTHER PUBLICATIONS

U.S. Appl. No. 10/170,738, filed Jun. 13, 2002, Rothman et al.

(Continued)

*Primary Examiner*—Bruce R. Campell
*Assistant Examiner*—Benjamin P. Blumel
(74) *Attorney, Agent, or Firm*—Jones Day

(57) ABSTRACT

Hybrid antigens comprising at least one antigenic domain, at least one heat shock protein binding domain, and at least one improved peptide linker there between are described which are useful for the induction of an immune response to the antigenic domain when administered alone or in a complex with at least one heat shock protein. The hybrid antigens and complexes can be used to treat infectious diseases and cancers that express an antigen of the antigenic domain.

47 Claims, 1 Drawing Sheet

U.S. PATENT DOCUMENTS

| | | | |
|---|---|---|---|
| 5,997,873 | A | 12/1999 | Srivastava |
| 6,017,540 | A | 1/2000 | Srivastava et al. |
| 6,030,618 | A | 2/2000 | Srivastava |
| 6,048,530 | A | 4/2000 | Srivastava |
| 6,127,393 | A | 10/2000 | Fernandez-Pol |
| 6,258,782 | B1 | 7/2001 | Barney et al. |
| 6,663,868 | B1 | 12/2003 | Rothman et al. |
| 2003/0166530 | A1 | 9/2003 | Rothman et al. |
| 2004/0043419 | A1 | 3/2004 | Rothman et al. |
| 2004/0071656 | A1 | 4/2004 | Weiland et al. |
| 2005/0202033 | A1 | 9/2005 | Flechtner et al. |

FOREIGN PATENT DOCUMENTS

| | | |
|---|---|---|
| WO | WO 95/25923 | 9/1995 |
| WO | WO 96/10411 | 4/1996 |
| WO | WO 97/06685 | 2/1997 |
| WO | WO 97/06821 | 2/1997 |
| WO | WO 97/10000 | 3/1997 |
| WO | WO 97/10001 | 3/1997 |
| WO | WO 97/10002 | 3/1997 |
| WO | WO 97/26910 | 7/1997 |
| WO | WO 98/23735 | 6/1998 |
| WO | WO 98/35705 | 8/1998 |
| WO | WO 99/22761 | 5/1999 |
| WO | WO 99/42121 | 8/1999 |
| WO | WO 2001/78772 | 10/2001 |
| WO | WO 03/062262 | 7/2003 |
| WO | WO 2004/071457 | 8/2004 |

OTHER PUBLICATIONS

Anderson, 1998, "Human gene therapy", Nature 392(6679 Suppl):25-30.

Arnold et al., 1995, "Cross-priming of Minor Histocompatibility Antigen-specific Cytotoxic T Cells upon Immunization with the Heat Shock Protein gp96." J. Exp. Med. 182:885-9.

Auger et al., 1996, "HLA-DR4 and HLA-DR10 motifs that carry susceptibility to rheumatoid arthritis bind 70-kD heat shock proteins." Nature Medicine 2:306-310.

Barrios et al., 1992, "Mycobacterial heat-shock proteins as carrier molecules. II: The use of the 70-kDa mycobacterial heat-shock protein as carrier for conjugated vaccines can circumvent the need for adjuvants and Bacillus Calmette Guerin priming." Euro. J. Immunol. 22:1365-1372.

Barrios et al., 1994, "Specificity of antibodies induced after immunization of mice with the mycobacterial heat shock protein of 65 kD." Clin. Exp. Immunol. 98:224-228.

Barrios et al., 1994, Heat shock proteins as carrier molecules: in vivo helper effect mediated by *Escherichia coli* GroEL and DnaK proteins requires cross-linking with antigen. Clin. Exp. Immunol. 98:229-233.

Bauer et al., 1995, "Identification of H-2Kb binding and immunogenic peptides from human papilloma virus tumour antigens E6 and E7." Scand. J. Immunol. 42:317-323.

Blachere & Srivastava, 1995, "Heat shock protein-based cancer vaccines and related thoughts on immunogenicity of human tumors." Seminars in Cancer Biology 6:349-355.

Blachere et al., 1993, "Heat shock protein vaccines against cancer.", J. Immunother. 14(4):352-356.

Blachere et al., 1997, "Heat shock protein-peptide complexes, reconstituted in vitro, elicit peptide-specific cytotoxic T lymphocyte response and tumor immunity." J. Exp. Med. 186:1315-1322.

Blond-Elguindi et al., Affinity Panning of Library of Peptides Displayed on Bacteriophages Reveals the Binding Specificity of BiP. Cell 75:717-728 (1993).

Borras-Cuesta et al., 1987, "Engineering of immunogenic peptides by co-linear synthesis of determinants recognized by B and T cells." Eur. J. Immunol. 17:1213-1215.

Castelli et al., 2001, "Human heat shock protein 70 peptide complexes specifically activate antimelanoma T cells." Cancer Res. 61(1):222-227.

Chen et al., 2000, "Enhancement of DNA vaccine potency by linkage of antigen gene to an HSP70 gene." Cancer Res. 60(4):1035-1042.

Cox et al., 1988, "Orientation of epitopes influences the immunogenicity of synthetic peptide dimers." Eur. J. Immunol. 18:2015-2019.

Czar et al., 1997, "Geldanamycin, a heat shock protein 90-binding benzoquinone ansamycin, inhibits steriod-dependent translocation of the glucocorticoid receptor from the cytoplasm to the nucleus." Biochemestry 36:7776-7785.

Davidoff et al., 1992, "Immune response to p53 is dependent upon p53/HSP70 complexes in breast cancers." Proc. Natl. Acad. Sci. USA 89:3439-3442.

Del Guidice, 1994, "Hsp70: a carrier molecule with built-in adjuvanticity." Experientia 50:1061-1066.

DeNagel & Pierce et al., 1993, "Heat shock proteins in immune responses." Critical Reviews In Immunology 13:71:81.

Dillman et al., 1995, "Heat Shock Proteins and Ischemic Injury." J. Cell. Biochem., Suppl. 19B, p. 190.

Edgington, 1995, "Therapeutic applications of heat shock proteins." Biotechnol. 13:1442-1444.

Fedoseyeva et al., 2001, "CD4+ T cell responses to self- and mutated p53 determinants during tumorigenesis in mice." J. Immunol. 164(11):5641-5651.

Feldweg & Srivastava, 1995, "Molecular heterogeneity of tumor rejection antigen/heat shock protein GP96." Int. J. Cancer 63:310-314.

Flajnik et al., 1991, "Which came first, MHC Class 1 or Class II?" Immunogenetics 33:295-300.

Flynn et al., 1989, "Peptide-dependent stimulation of the ATPase activity of the molecular chaperone BiP is the result of conversion of oligomers to active monomers." Science 245:385-390.

Francis et al., 1987, "Non-responsiveness to a foot-and-mouth disease virus peptide overcome by addition of foreign helper T-cell determinants." Nature 330:168-170.

Galigniana et al., 1998, "Heat shock protein 90-dependent (geldanamycin-inhibited) movement of the glucocorticoid receptor through the cytoplasm to the nucleus requires intact cytoskeleton." Mol. Endo. 12:1903-1913.

Gething, et al., 1995, "Binding Sites for Hsp70 Molecular Chaperones in Natural Proteins." Cold Spring Harb. Symp. Quant. Biol. 60:417-28.

Giboa, 1996, "Immunotherapy of cancer with genetically modified tumor vaccines." Seminars in Oncology 23:101-107.

Gragerov et al., 1994, "Different peptide binding specificities of hsp70 family members." J. Mol. Biol. 235:133-135.

Gragerov et al., 1994, "Specificity of DnaK-peptide binding." J. Mol. Biol. 235:848-854.

Greene et al., 1995, "Effect of nucleotide on the binding of peptides to 70-kDa heat shock protein." J. Biol. Chem. 270(7):2967-2978.

Heike et al., 1996, "Heat shock protein-peptide complexes for use in vaccines." J. Leukoc. Biol. 60(2):153-158.

Heikema et al., 1997, "Generation of heat shock protein-based vaccines by intracellular loading of gp96 with antigenic peptides." Immunol. Lett. 57(1-3):69-74.

Hinds et al., 1987, "Immunological evidence for the association of p53 with a heat shock proteins, hsc70, in p53-plus-ras-transformed cell lines." Mol Cell Biol. 7(8):2863-2869.

Hohfeld et al., 1995, "Hip, a novel cochaperone involved in the eukaryotic Hsc70/Hsp40 reaction cycle." Cell 83:589-598.

Huang et al., 2000, "In Vivo Cytotoxic T Lymphocytes Elicitation by Mycobacterial Heat Shock Protein 70 Fusion Proteins Maps to a Discrete Domain and Is CD4.sup.30 T Cell Independent." J. Exp. Med. 191:403-408.

Jaattela, 1995, "Over-expression of hsp70 confers tumorigenicity to mouse fibrosarcoma cells." Int. J. Cancer, 60 (5), pp. 689-693.

Jakob et al., 1996, "Assessment of the ATP binding properties of Hsp90." J. Biol. Chem. 271:10035-10041.

Jindal, S., 1996, "Heat shock proteins: applications in health and disease." Trends Biotechnol. 14:17-20.

Konen-Waisman et al., 1999, "Self heat-shock protein (hsp60) peptide serves in a conjugate vaccine against a lethal pneumococcal infection." J. Infect. Dis. 179(2):403-413.

Lewis et al., 1999, "Pilot study of vaccination with autologous tumor-derived gp96 heat shock protein-peptide complex(HSPPC-96) in patients with resected pancreatic adenocarcinoma." Meeting Abstract, Proceedings of the Annual Meeting of the American Society of Clinical Oncology, 18:A1687.

Li, Z. et al., 1993, "Tumor rejection antigen gp96/grp94 is an ATPase: implications for protein folding and antigen presentation." EMBO J. 12:3143-51.

Little, et al., 1994, "The glucose-regulated proteins (GRP78 and GRP94): functions, gene regulation, and applications." Critical Reviews in Eukaryotic Gene Expression, 1994 4(1) pp. 1-18.

Lopez-Guerrero et al., 1993, "Modulation of adjuvant arthritis in Lewis rats by recombinant vaccinia virus expressing the human 60-kilodalton heat shock protein." Infect. Immun. 61(10):4225-4231.

Lovett et al., 1993, "Rubella virus-specific cytotoxic T-lymphocyte responses: identification of the capsid as a target of major histocompatibility complex class I-restricted lysis and definition of two epitopes." J. Virol. 67(10):5849-5858.

Lowrie et al., 1994, "Towards a DNA vaccine against tuberculosis." Vaccine 12:1537-1540.

Lowrie et al., 1995, "*Mycobacterium leprae* HSP65 Vaccinates mice against Tuberculosis when Expressed from the Cloned Gene in Transplanted Bone Marrow Cells." J. Cell. Biochem. Suppl. 0(19b):220.

Lukacs et al., 1993, "Tumor cells transfected with a bacterial heat-shock gene lose tumorigenicity and induce protection against tumors." J. Exp. Med. 178:343-348.

Lukacs et al., 1994,"Protection against tumours by mycobacterial heat shock protein gene." Cancer Gene Therapy, 1:217.

Lussow et al., 1991, "Mycobacterial heat-shock proteins as carrier molecules." J. Eur. Immunol. 21:2297-2302.

Mastrangelo et al., 1996, "Gene therapy for human cancer: an essay for clinicians." Seminars in Oncology, 23:4-21.

McCarty et al., 1995, "The role of ATP in the functional cycle of the DnaK chaperone system." J. Mol. Biol. 249:126-137.

Melcher et al., 1998, "Tumor Immonogenicity is Determined by the Mechanism of Cell Death Via Induction of Heat Shock Protein Expression." Nature Medicine 4:581-587.

Melnick, et al., 1992, "The endoplasmic reticulum stress protein GRP94 in addition to BiP, associates with unassembled immunoglobulin chains." J. of Biochem. 267:21303-21306.

Meng et al., 1999, "Tumor suppressor gene as targets for cancer therapy." Gene Therapy of Cancer, Lattime and Gerson, Eds., Academic Press, Chap. 1, pp. 3-20.

Minami et al., 1996, "Regulation of the heat-shock protein 70 reaction cycle by the mammalian DnaJ homolog, Hsp40." J. Biol. Chem. 271:19617-19624.

Moroi, 2000, "Induction of cellular immunity by immunization with novel hybrid peptides complexed to heat shock protein 70." Proc Natl Acad Sci U S A 97(7):3485-90.

Multhoff et al., 1995, "A stress-inducible 72-kDa heat-shock protein (HSP72) is expressed on the surface of human tumor cells, but not on normal cells." Int. J. Cancer 61:272-279.

Munro and Pelham, 1987, "A C-terminal signal prevents secretion of luminal ER proteins." Cell, 480:899-907.

Mustafa et al., 1993, "Human T cells recognize mycobacterial heat shock proteins in the context of multiple HLA-DR molecules: studies with healty subjects vaccinated with *Mycobacterium bovis* BCG and *Mycobacterium leprae*." Infection and Immunity 61:5294-5301.

Nadeau et al., 1992, "83-kilodalton heat shock proteins of trypanosomes are potent peptide-stimulated ATPases." Protein Science 1:970-979.

Nadeau et al., 1992, "Hsp90 chaperonins possess ATPase activity and bind heat shock transcription factors and peptidyl prolyl isomerases." J. Biol. Chem. 268:1479-1487.

Ngo et al., 1994, "Computational Complexity Protein Structure Prediction and the Levinthal Paradox." Birkhauser Boston, vol. 14, pp. 491-495.

Nieland et al., 1996, "Isolation of an immunodominant viral peptide that is endogenously bound to the stress protein GP96/GRP94." Proc. Natl. Acad. Sci. USA 93:6135-6139.

Nilsson et al., 1992, "Fusion proteins in biotechnology and structural biology." Curr. Opin. Struct. Biol. 2:569-575.

Nygren et al., 1994, "Engineering proteins to facilitate bioprocessing." Trends Biotechnol. 12(5):184-188.

Omura et al., 1979, "Herbimycin, a new antibiotic produced by a strain of Strepotomyces." J. Antibiotics 32:255-261.

Palleros et al., 1993, "ATP-induced protein-Hsp70 complex dissociation requires K+ but not ATP hydrolysis." Nature 365:664-666.

Pardoll, 1993, "New strategies for enhancing the immunogenicity of tumors." Current Opinion in Immunology 5:719-725.

Partidos et al., 1991, "Immune responses in mice following immunization with chimeric synthetic peptides representing B and T cell epitopes of measles virus proteins." J. Gen. Virol. 72:1293-1299.

Pelham, 1988, "Evidence that luminal ER proteins are sorted from secreted proteins in a post-ER compartment." EMBO J. 7:913-918.

Perraut, 1993, "Successful primate immunization with peptides conjugated to purified protein derivative or mycobacterial heat shock proteins in the absence of adjuvants." Clin. Exp. Immunol. 93:382-386.

Pidoux et al., 1992, "Analysis of the BiP gene and identification of an ER retention signal in Schizosaccharomyces pombe." EMBO J. 11:1583-1591.

Plumier et al., 1995, "Transgenic mice expressing the human heat shock protein 70 have improved post-ischemic myocardial recovery." J. Clin. Invest. 95 (4), pp. 1854-1860.

Porgador et al., 1994, "Immunotherapy of tumor metastasis via gene therapy." Nat. Immun. 13:113-130.

Retzlaff et al., 1994, "Bacterial heat shock proteins directly induce cytokine mRNA and interleukin-1 secretion in macrophage cultures." Infect. Immun. 62:5689-5693.

Riddell et al., 1996, "T-cell mediated rejection of gene-modified HIV-specific cytotoxic T lymphocytes in HIV-infected patients." Nature Medicine 2:216-233.

Rosenberg et al., 1996, "T7 Select Phage Display System: A powerful new protein display system based on Bacteriophage T7." inNovations (newsletter of Novagen, Inc.) No. 6, pp. 1-6.

Sato et al., 1994, "70 kDA heat shock protein as a tumor antigen and a target for the host's anti-tumor resistance by cytotoxic T lymphocytes." Proc. Annu. Meet. Am. Assoc. Cancer Res. 35:A2959.

Scheerlinck et al., 1993, Redistribution of a murine humoral immune response following removal of an immunodominant B cell epitope from a recombinant fusion protein. Mol. Immunol. 30:733-739.

Schmid et al., 1994, "Kinetics of molecular chaperone action." Science 263:971-973.

Silva and Lowrie, 1994, "A single mycobacterial protein (hsp 65) expressed by a transgenic antigen-presenting cell vaccinates mice against tuberculosis." Immunology 82:244-248.

Srivastava & Maki, 1991, "Stress-induced proteins in immune response to cancer." Current Topics in Microbiology and Immunology 167:109-123.

Srivastava and Udono, 1994, "Heat shock protein-peptide complexes in cancer immunotherapy." Curr. Opin. Immunol. 6(5):728-732.

Srivastava et al., 1986, "Tumor rejection antigens of chemically induced sarcomas of inbred mice." Proc. Natl. Acad. Sci. USA 83:3407-3411.

Srivastava, 1993, "Peptide-binding heat shock proteins in the endoplasmic reticulum: role in immune response to cancer and in antigen presentation." Adv. Cancer Res. 62:153-177.

Srivastava, 1994, "Heat shock proteins in immune response to cancer: the Fourth Paradigm." Experentia 50:1054-1060.

Srivastava, 2002, "Interaction of Heat Shock Proteins and Antigen Presenting Cells: Chaperoning of the Innate and Adaptive Immune Response." Ann. Rev. Immunol. 20:395-425.

Srivatava et al., 1987, "5'-structural analysis of genes encoding polymorphic antigens of chemically induced tumors." Proc. Natl. Acad. Sci USA 84:3807-3811.

Suto, et al., 1995, "A Mechanism for the Specific Immunogenicity of Heat Shock Protein-Chaperoned Peptides." Science 269:1585-7.

Suzue, et al., 1996, "Adjuvant-Free hsp Fusion Protein System Elicits Humoral and Cellular Immune Responses to HIV-1 p24.sup. 1." J. Immunol. 156:873-9.

Suzuki et al., 1991, "Regulating the retention of T-cell receptor alpha chain variants within the endoplasmic reticulum: Ca(2-30)-dependent association with BiP." J. Cell Biol. 114:189-205.

Tamura, et al., 1997, "Immunotherapy of tumors with autologous tumor-derived heat shock protein preparations." Science 278:117-120.

Tarpey, I. et al., 1994, "Human cytotoxic T lymphocytes stimulated by endogenously processed human papillomavirus type 11 E7 recognize a peptide containing a HLA-A2 (A*0201) motif." Immunology 81:222-7.

Tavaria et al., 1996, "Cell Stress and Chaperones 1:23-28." Cell Stress and Chaperones 1:23-28.

Theobald et al., 1995, "Targeting p53 as a general tumor antigen." Proc. Natl. Acad. Sci. USA 92(26):11993-11997.

Thomson et al., 1995, "Minimal epitopes expressed in a recombinant polyepitope protein are processed and presented to CD8+ cytotoxic T cells: implications for vaccine design." Proc. Natl. Acad. Sci. USA 92(13):5845-5849.

Thomson et al., 1996, "Recombinant polyepitope vaccines for the delivery of multiple CD8 cytotoxic T cell epitopes." J. Immunol. 157(2):822-6.

Todryk et al., 1999, "Heat Shock Protein 70 Induced during Tumor Cell Killing Induces Th1 Cytokines and Targets Immature Dendritic Cell Precursors to Enhance Antigen Uptagke." J. Immunol. 163:1398-1408.

Udono et al., 1994, "Comparison of tumor-specific immunogenicities of stress-induced proteins gp96, hsp90, and hsp70." J. Immun. 152, pp. 5398-5403.

Udono, et al., 1993, "Heat shock protein 70-associated peptides elicit specific cancer immunity." J. Exp. Med. 178:1391-6.

Udono, et al., 1994, "Cellular requirements for tumor-specific immunity elicited by heat shock proteins: Tumor rejection antigen gp96 primes CD8+ T Cells in vivo." Pro. Natl. Acad. Sci. 91:3077-81.

Ullrich et al., 1986, "A mouse tumor-specific transplantation antigen is a heat shock-related protein." Proc. Natl. Acad. Sci. USA 83:3121-3125.

Verma et al., 1997, "Gene therapy—promises, problems and prospects." Nature 389(6648):239-242.

Von Heijne, 1985, "Signal sequences. The limits of variation." J. Mol. Biol. 184:99-105.

Wearsch et al., 1997, "Interaction of endoplasmic reticulum chaperone GRP94 with peptide substrates is adenine nucleotide-independent." J. Biol. Chem. 272:5152-5156.

Wells et al., 1998, "Hsp72-mediated Augmentation of MHC Class I Surface Expression and Endogenous Antigen Presentation." Int. Immunol 10:609-617.

Whitesell, et al., 1994, "Inhibition of heat shock protein HSP90-pp60v-src heteroprotein complex formation by benzoquinone ansamycins: essential role for stress proteins in oncogenic transformation." Proc. Natl. Acad. Sci. USA 91:8324-8328.

Yamamoto et al., 1993, "Listeria monocytogenes-induced gamma interferon secretion by intestinal intraepithelial gamma/delta T lymphocytes." Infection and Immunity 61:2154-2161.

Yamazaki et al., 1999, "Cutting Edge: Tumor Secreted Heat Shock-Fusion Protein Elicits CD8 Cells for Rejection." J. Immunol. 163:5178-5182.

Zhu et al., 1995, "Both immunization with protein and recombinant vaccinia virus can stimulate CTL specific for the E7 protein of human papilloma virus 16 in H-2d mice." Scand. J. Immunol. 42:557-563.

Zhu et al., 1996, "Structural analysis of substrate binding by the molecular chaperone DnaK." Science 272:1606-1614.

HEAT SHOCK PROTEIN-BASED VACCINES AND IMMUNOTHERAPIES

CROSS-REFERENCE TO RELATED APPLICATIONS

This application claims priority under 35 U.S.C. § 119(e) to provisional applications Ser. No. 60/462,469, filed Apr. 11, 2003; Ser. No. 60/463,746, filed Apr. 18, 2003; and Ser. No. 60/503,417, filed Sep. 16, 2003, all three of which are incorporated herein by reference in their entireties.

INTRODUCTION

The present invention relates to methods and compositions for inducing an immune response in a subject, wherein the subject is administered an effective amount of at least one or more defined hybrid antigens optionally in combination with one or more heat shock proteins. These methods and compositions may be used in the treatment of infectious diseases and cancers.

BACKGROUND OF THE INVENTION

Heat shock proteins were originally observed to be expressed in increased amounts in mammalian cells which were exposed to sudden elevations of temperature, while the expression of most cellular proteins is significantly reduced. It has since been determined that such proteins are produced in response to various types of stress, including glucose deprivation. As used herein, the term "heat shock protein" will be used to encompass both proteins that are expressly labeled as such as well as other stress proteins, including homologues of such proteins that are expressed constitutively (i.e., in the absence of stressful conditions). Examples of heat shock proteins include BiP (also referred to as grp78), hsp70, hsc70, gp96 (grp94), hsp60, hsp40 and hsp90.

Heat shock proteins have the ability to bind other proteins in their non-native states, and in particular to bind nascent peptides emerging from ribosomes or extruded into the endoplasmic reticulum. Hendrick and Hartl, *Ann. Rev. Biochem.* 62:349-384 (1993); Hartl, *Nature* 381:571-580 (1996). Further, heat shock proteins have been shown to play an important role in the proper folding and assembly of proteins in the cytosol, endoplasmic reticulum and mitochondria; in view of this function, they are referred to as "molecular chaperones." Frydman et al., *Nature* 370:111-117 (1994); Hendrick and Hartl, *Ann. Rev. Biochem.* 62:349-384 (1993); Hartl, *Nature* 381:571-580 (1996).

For example, the protein BiP, a member of a class of heat shock proteins referred to as the hsp70 family, has been found to bind to newly synthesized, unfolded µ immunoglobulin heavy chain prior to its assembly with light chain in the endoplasmic reticulum. Hendershot et al., *J. Cell Biol.* 104:761-767 (1987). Another heat shock protein, gp96, is a member of the hsp90 family of stress proteins which localizes in the endoplasmic reticulum. Li and Srivastava, *EMBO J.* 12:3143-3151 (1993); Mazzarella and Green, *J. Biol. Chem.* 262:8875-8883 (1987). It has been proposed that gp96 may assist in the assembly of multi-subunit proteins in the endoplasmic reticulum. Wiech et al., *Nature* 358:169-170 (1992).

It has been observed that heat shock proteins prepared from tumors in experimental animals were able to induce immune responses in a tumor-specific manner; that is to say, heat shock protein purified from a particular tumor could induce an immune response in an experimental animal which would inhibit the growth of the same tumor, but not other tumors. Srivastava and Maki, *Curr. Topics Microbiol.* 167:109-123 (1991). Genes encoding heat shock proteins have not been found to exhibit tumor-specific DNA polymorphism. Srivastava and Udono, *Curr. Opin. Immunol.* 6:728-732 (1994). High resolution gel electrophoresis has indicated that gp96 may be heterogeneous at the molecular level. Feldweg and Srivastava, *Int. J. Cancer* 63: 310-314 (1995). Evidence suggests that the source of heterogeneity may be populations of small peptides adherent to the heat shock protein, which may number in the hundreds. Id. It has been proposed that a wide diversity of peptides adherent to tumor-synthesized heat shock proteins may render such proteins capable of eliciting an immune response in subjects having diverse HLA phenotypes, in contrast to more traditional immunogens which may be somewhat HLA-restricted in their efficacy. Id.

Nieland et al. (*Proc. Natl. Acad. Sci. U.S.A.* 93:6135-6139 (1996)) identified an antigenic peptide containing a cytotoxic T lymphocyte (CTL) vesicular stomatitis virus (VSV) epitope bound to gp96 produced by VSV-infected cells. Neiland's methods precluded the identification of any additional peptides or other compounds which may also have bound to gp96, and were therefore unable to further characterize higher molecular weight material which was bound to gp96 and detected by high pressure liquid chromatography.

It has been reported that a synthetic peptide comprising multiple iterations of NANP (Asp Ala Asp Pro; SEQ ID NO:1) malarial antigen, chemically cross-linked to glutaraldehyde-fixed mycobacterial hsp65 or hsp70, was capable of inducing antibody formation (i.e., a humoral response) in mice in the absence of any added adjuvant; a similar effect was observed using heat shock protein from the bacterium *Escherichia coli*. Del Guidice, *Experientia* 50:1061-1066 (1994); Barrios et al., *Clin. Exp. Immunol.* 98:224-228 (1994); Barrios et al., *Eur. J. Immunol.* 22:1365-1372 (1992). Cross-linking of synthetic peptide to heat shock protein and possibly glutaraldehyde fixation was required for antibody induction. Barrios et al., *Clin. Exp. Immunol.* 98:229-233.

PCT/US96/13363 describes hybrid antigens comprising an antigenic domain and a heat shock protein binding domain that, in a complex with a heat shock protein, induces immunological responses to antigens and are thus useful for treatment of cancer and infectious diseases. PCT/US98/22335 describes additional heat shock protein binding domains for similar uses, as well as the ability for hybrid antigen administered alone to induce an immune response. It has now been discovered that improvements in the peptide linker present between the at least one antigenic domain and at least one heat shock protein binding domain in a hybrid antigen leads to an increase in biological activity. This increase is also found to provide an increase in inducing an immune response against the antigenic portion of the hybrid antigen. It is towards these improved peptide linkers, hybrid peptides containing them and their uses with and without heat shock protein, that the present application is directed.

SUMMARY OF THE INVENTION

The present invention relates to methods and compositions for inducing an immune response in a subject, wherein at least one defined hybrid antigen optionally in a complex with a heat shock protein is administered to the subject. The hybrid antigen comprises at least one antigenic domain and at least one heat shock protein binding domain, and at least one peptide linker there between. Induction of an immune response to an antigen associated with a disease such as an infectious disease or tumor is useful for treatment of the disease. The antigenic or immunogenic domain of the hybrid antigen may be an entire protein or peptide antigen, or may be only a portion of the selected antigen, for example a selected epitope of the antigen. The heat shock protein binding domain is a peptide that binds to a heat shock protein, preferably a peptide of 7-15 amino acids that binds to a heat shock protein, more preferably a hydrophobic peptide that binds to a heat shock protein, and most preferably a hydrophobic peptide of 7-15 amino acids that binds to a heat shock protein. The linker has a sequence from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gin Leu Lys (QLK), Gin Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A; $AA_2$ is K, V, or E, preferably E, more preferably V and most preferably K; and $AA_3$ is V, S, F, K, A, E, or T, preferably F, more preferably S and most preferably V. Among the foregoing, Gin Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred.

The present invention provides for methods of administering such hybrid antigens alone, as well as heat shock protein/hybrid antigen compositions, the latter comprising (i) combining one or more heat shock protein with one or more hybrid antigens in vitro, under conditions wherein binding of hybrid antigen to heat shock protein occurs to form a hybrid antigen/heat shock protein complex; and (ii) administering the hybrid antigen, bound to heat shock protein, in an effective amount to a subject in need of such treatment.

Alternatively, hybrid antigens optionally in combination with heat shock protein may be introduced into a subject by administering to the subject a nucleic acid encoding the hybrid antigen, optionally with nucleic acid encoding the heat shock protein.

Thus, in a first aspect, the invention is directed to a hybrid antigen consisting essentially of an antigenic domain of an infectious agent or tumor antigen, a binding domain that non-covalently binds to a heat shock protein, and a peptide linker separating the antigenic domain and the binding domain, and wherein the peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gin Leu Lys (QLK), Gin Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A; $AA_2$ is K, V, or E, preferably E, more preferably V and most preferably K; and $AA_3$ is V, S, F, K, A, E, or T, preferably F, more preferably S and most preferably V. Among the foregoing, Gin Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred.

In a second aspect, the invention is directed to a hybrid antigen consisting essentially of a plurality of antigenic domains of one or more infectious agents or one or more tumor antigens, at least one binding domain that non-covalently binds to a heat shock protein, and at least one peptide linker separating the antigenic domains and the at least one binding domain, and wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gin Leu Lys (QLK), Gin Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A ; $AA_2$ is K, V, or E, preferably E, more preferably V and most preferably K; and $AA_3$ is V, S, F, K, A, E, or T, preferably F, more preferably S and most preferably V. Among the foregoing, Gin Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred. In a particular embodiment, at least one of the antigenic domains in the aforementioned hybrid antigen is a T helper epitope.

In a third aspect, the invention is directed to a hybrid antigen comprising an antigenic domain of an infectious agent or tumor antigen and a binding domain that non-covalently binds to a heat shock protein, and a peptide linker there between, and wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gin Leu Lys (QLK), Gin Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A; $AA_2$ is K, V, or E, preferably E, more preferably V and most preferably K; and $AA_3$ is V, S, F, K, A, E, or T, preferably F, more preferably S and most preferably V. Among the foregoing, Gin Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred. In a particular embodiment, the aforementioned hybrid antigen has a peptide linker separating the antigenic domain and the binding domain.

In a fourth aspect, the invention is directed to a hybrid antigen comprising a plurality of antigenic domains of one or more infectious agents or one or more tumor antigens and at least one binding domain that non-covalently binds to a heat shock protein, and at least one peptide linker there between, and wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gin Leu Lys (QLK), Gin Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A ; $AA_2$ is K, V, or E, preferably E, more preferably V and most preferably K; and $AA_3$ is V, S, F, K, A, E, or T, preferably F, more preferably S and most preferably V. Among the foregoing, Gln Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred. In a particular embodiment, at least one of the antigenic domains is a T helper epitope.

In a fifth aspect, the invention is directed to a composition for inducing an immune response to an infectious agent or tumor antigen comprising at least one hybrid antigen, the hybrid antigen comprising an antigenic domain of the infectious agent or tumor antigen, a binding domain that non-covalently binds to a heat shock protein, and at least one peptide linker there between, and wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gin Leu Lys (QLK), Gin Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A ; $AA_2$ is K, V, or E, preferably E, more preferably V and most preferably K; and $AA_3$ is V, S, F, K, A, E, or T, preferably F, more preferably S and most preferably V. Among the foregoing, Gin Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred. In one embodiment, the composition comprises a plurality of hybrid antigens, and one of the hybrid antigens can comprise a T helper epitope.

In a sixth aspect, the invention is directed to a composition for inducing an immune response to an infectious agent or tumor antigen comprising at least one hybrid antigen, the hybrid antigen comprising a plurality of antigenic domains at least one of which is from the infectious agent or tumor antigen, at least one binding domain that non-covalently binds to a heat shock protein, and at least one $$ peptide linker there between, and wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gin Leu Lys (QLK), Gin Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A ; $AA_2$ is K, V, or E, preferably E, more preferably V and most preferably K; and $AA_3$ is V, S, F, K, A, E, or T, preferably F, more preferably S and most preferably V. Among the foregoing, Gln Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred.

In a seventh aspect, the invention is directed to a composition for inducing an immune response to an infectious agent or tumor antigen comprising at least one hybrid antigen, the hybrid antigen consisting essentially of an antigenic domain of the infectious agent or tumor antigen, a binding domain that non-covalently binds to a heat shock protein, and a peptide linker separating the antigenic domain and the binding domain, and wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gln Leu Lys (QLK), Gln Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A; $AA_2$ is K, V, or E, preferably E, more preferably V and most preferably K; and $AA_3$ is V, S, F, K, A, E, or T, preferably F, more preferably S and most preferably V. Among the foregoing, Gin Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred. In one embodiment, the aforementioned composition comprises a plurality of hybrid antigens. In another aspect, at least one of the plurality of hybrid antigens comprises a T helper epitope.

In an eighth aspect, the invention is directed to a composition for inducing an immune response to an infectious agent or tumor antigen comprising at least one hybrid antigen, the hybrid antigen consisting essentially of a plurality of antigenic domains at least one of which is from the infectious agent or tumor antigen, at least one binding domain that non-covalently binds to a heat shock protein, and at least one peptide linker separating the antigenic domain and the binding domain, and wherein at least one peptide linker is from among Phe Phe Arg Lys (FFRK; _SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gln Leu Lys (QLK), Gln Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A; $AA_2$ is K, V, or E, preferably E, more preferably V and most preferably K; and $AA_3$ is V, S, F, K, A, E, or T, preferably F, more preferably S and most preferably V. In one embodiment, at least one of the antigenic domains comprises a T helper epitope.

In a ninth aspect, the invention is directed to a method for inducing an immune response to an infectious agent or tumor antigen comprising administering to a subject a complex of a heat shock protein and a hybrid antigen comprising at least one antigenic domain of the infectious agent or tumor antigen, at least one binding domain comprising a peptide that non-covalently binds to a heat shock protein, and a peptide linker there between; wherein the hybrid antigen and the heat shock protein are non-covalently bound, and wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gin Leu Lys (QLK), Gin Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A; $AA_2$ is K, V, or E, preferably E, more preferably V and most preferably K; and $AA_3$ is V, S, F, K, A, E, or T, preferably F, more preferably S and most preferably V. Among the foregoing, Gln Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred. In one embodiment, the complex comprises a plurality of hybrid antigens. In an embodiment, at least one of the hybrid antigens is a T helper epitope. In another embodiment, the hybrid antigen comprises a plurality of antigenic domains, and at least one of the antigenic domains can be a T helper epitope. In yet another embodiment wherein the complex comprises a plurality of hybrid antigens, at least one of the hybrid antigens comprises a plurality of antigenic domains. In another embodiment of this aspect of the invention, the heat shock protein is a hsp70 .

In a tenth aspect, the invention is directed to a method for inducing an immune response to an infectious agent or tumor antigen comprising administering to a subject a complex of a heat shock protein and a hybrid antigen, the hybrid antigen consisting essentially of at least one antigenic domain of an infectious agent or tumor antigen, a binding domain that non-covalently binds to a heat shock protein, and a peptide linker separating the antigenic domain and the binding domain, and wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gln Leu Lys (QLK), Gln Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A ; $AA_2$ is K, V, or E, preferably E, more preferably V and most preferably K; and $AA_3$ is V, S, F, K, A, E, or T, preferably F, more preferably S and most preferably V. Among the foregoing, Gln Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred. In one embodiment, the complex comprises a plurality of hybrid antigens. In another embodiment, at least one of the hybrid antigens is a T helper epitope. In a further embodiment, the hybrid antigen comprises a plurality of antigenic domains. In yet a further embodiment, at least one of the antigenic domains is a T helper epitope. In still yet another embodiment, the complex comprises a plurality of hybrid antigens, at least one of the hybrid antigens comprising a plurality of antigenic domains. In a preferred embodiment of this aspect, the heat shock protein is a hsp70.

In an eleventh aspect, the invention is directed to a method for inducing an immune response to an infectious agent or tumor antigen comprising administering to a subject at least one hybrid antigen comprising at least one antigenic domain of the infectious agent or tumor antigen, at least one binding domain comprising a peptide that non-covalently binds to a heat shock protein, and at least one peptide linker there between, and wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gln Leu Lys (QLK), Gln Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A; $AA_2$ is K, V, or E, preferably E, more preferably V and most preferably K; and $AA_3$ is V, S, F, K, A, E, or T, preferably F, more preferably S and most preferably V. Among the foregoing, Gln Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred. In one embodiment, the complex comprises a plurality of hybrid antigens. In another embodiment, at least one of the hybrid antigens is a T helper epitope. In another embodiment, the hybrid antigen comprises a plurality of antigenic domains. In a further embodiment, at least one of the antigenic domains is a T helper epitope. In yet a further embodiment, the complex comprises a plurality of hybrid antigens, at least one of the hybrid antigens comprising a plurality of antigenic domains. In another embodiment of this aspect of the invention, a peptide linker separates the antigenic domain and the binding domain.

In a twelfth embodiment, the invention is directed to a method for inducing an immune response to an infectious agent or tumor antigen comprising administering to a subject at least one hybrid antigen, the hybrid antigen consisting essentially of at least one antigenic domain of an infectious agent or tumor antigen, a binding domain that non-covalently binds to a heat shock protein, and a peptide linker separating the antigenic domain and the binding domain, and wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gln Leu Lys (QLK), Gln Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A; $AA_2$ is K, V, or E, preferably E, more preferably V and most preferably K; and $AA_3$ is V, S, F, K, A, E, or T, preferably F, more preferably S and most preferably V. Among the foregoing, Gln Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred. In one embodiment, the complex comprises a plurality of hybrid antigens. In a further embodiment, at least one of the hybrid antigens is a T helper epitope. In another embodiment, the hybrid antigen comprises a plurality of antigenic domains. In yet another embodiment, at least one of the antigenic domains is a T helper epitope. In yet still a further embodiment, the complex comprises a plurality of hybrid antigens, at least one of the hybrid antigens comprising a plurality of antigenic domains.

In a thirteenth aspect, the invention is directed to a method for treating an infectious disease or cancer comprising administering to a subject a complex of a heat shock protein and a hybrid antigen comprising at least one antigenic domain of an infectious agent or tumor antigen associated with the infectious disease or cancer, a binding domain comprising a peptide that non-covalently binds to a heat shock protein, and a peptide linker there between; and wherein the hybrid antigen and the heat shock protein are non-covalently bound, and wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gln Leu Lys (QLK), Gln Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A; $AA_2$ is K, V, or E, preferably E, more preferably V and most preferably K; and $AA_3$ is V, S, F, K, A, E, or T, preferably F, more preferably S and most preferably V. Among the foregoing, Gln Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred. In one embodiment, the complex comprises a plurality of hybrid antigens. In another embodiment, at least one of the hybrid antigens is a T helper epitope. In yet another embodiment, the hybrid antigen comprises a plurality of antigenic domains. In still another embodiment, at least one of the antigenic domains is a T helper epitope. In yet still a further embodiment, the complex comprises a plurality of hybrid antigens, at least one of the hybrid antigens comprising a plurality of antigenic domains. In an embodiment of this aspect of the invention, a peptide linker separates the antigenic domain and the binding domain. In a preferred embodiment of this aspect of the invention, the heat shock protein is a hsp70.

In a fourteenth aspect, the invention is directed to a method for treating an infectious disease or cancer comprising administering to a subject a complex of a heat shock protein and a hybrid antigen, the hybrid antigen consisting essentially of at least one antigenic domain of an infectious agent or tumor antigen associated with the infectious disease or cancer, at least one binding domain that non-covalently binds to a heat shock protein, and a peptide linker separating the antigenic domain and the binding domain, and wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gln Leu Lys (QLK), Gln Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A; $AA_2$ is K, V, or E, preferably E, more preferably V and most preferably K; and $AA_3$ is V, S, F, K, A, E, or T, preferably F, more preferably S and most preferably V. Among the foregoing, Gln Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred. In one embodiment, the complex comprises a plurality of hybrid antigens. In another aspect, at least one of the hybrid antigens is a T helper epitope. In yet another aspect, the hybrid antigen comprises a plurality of antigenic domains. In yet another aspect, at least one of the antigenic domains is a T helper epitope. In a further aspect, the complex comprises a plurality of hybrid antigens, at least one of the hybrid antigens comprising a plurality of antigenic domains. In a preferred embodiment, the heat shock protein is a hsp70.

In a fifteen aspect, the invention is directed to a method for treating an infectious disease or cancer comprising administering to a subject at least one hybrid antigen comprising at least one antigenic domain of an infectious agent or tumor antigen associated with the infectious disease or cancer, a binding domain comprising a peptide that non-covalently binds to a heat shock protein, and a peptide linker there between, and wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gln Leu Lys (QLK), Gln Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A; $AA_2$ is K, V, or E, preferably E, more preferably V and most preferably K; and $AA_3$ is V, S, F, K, A, E, or T, preferably F, more preferably S and most preferably V. Among the foregoing, Gln Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred. In one embodiment, the complex comprises a plurality of hybrid antigens. In another aspect, at least one of the hybrid antigens is a T helper epitope. In yet another aspect, the hybrid antigen comprises a plurality of antigenic domains. In still a further aspect, at least one of the antigenic domains is a T helper epitope. In still yet another aspect, the complex comprises a plurality of hybrid antigens, at least one of the hybrid antigens comprising a plurality of antigenic domains. In one embodiment of this aspect of the invention, a peptide linker separates the antigenic domain and the binding domain.

In a sixteenth aspect, the invention is directed to a method for treating an infectious disease or cancer comprising administering to a subject at least one hybrid antigen, the hybrid antigen consisting essentially of at least one antigenic domain of an infectious agent or tumor antigen associated with an infectious disease or cancer, a binding domain that non-covalently binds to a heat shock protein, and a peptide linker separating the antigenic domain and the binding domain, and wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gln Leu Lys (QLK), Gln Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A ; $AA_2$ is K, V, or E, preferably E, more preferably V and most preferably K; and $AA_3$ is V, S, F, K, A, E, or T, preferably F, more preferably S and most preferably V. Among the foregoing, Gln Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred. In one embodiment, the complex comprises a plurality of hybrid antigens. In another embodiment, at least one of the hybrid antigens is a T helper epitope. In yet another embodiment, the hybrid antigen comprises a plurality of antigenic domains. In still yet another embodiment, at least one of the antigenic domains is a T helper epitope. In another embodiment, the complex comprises a plurality of hybrid antigens, at least one of the hybrid antigens comprising a plurality of antigenic domains.

In a seventeenth aspect, the invention is directed to a peptide from among Phe Phe Arg Lys (FFRK; _SEQ ID NO:699); Phe Arg Lys (FRK); Phe Arg Lys Asn (FRKN, _SEQ ID NO:701); Arg Lys Asn (RKN); Phe Phe Arg Lys Asn (FFRKN, _SEQ ID NO:702); Phe Arg (FR), Gln Leu Lys (QLK), Gln Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A; $AA_2$ is K, V, or E, preferably E, more preferably V and most preferably K; and $AA_3$ is V, S, F, K, A, E, or T, preferably F, more preferably S and most preferably V.

In an eighteenth aspect, the invention is directed to an immunogenic polypeptide comprising a plurality of antigenic domains, at least one heat shock protein binding domain and at leatst one peptide linker there between wherein at least one peptide linker is from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gln Leu Lys (QLK), Gln Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A; $AA_2$ is K, V, or E, preferably E, more preferably V and most preferably K; and $AA_3$ is V, S, F, K, A, E, or T, preferably F, more preferably S and most preferably V. Among the foregoing, Gln Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred.

In a nineteenth aspect, the invention is directed to a polynucleotide encoding any of the hybrid antigens in the aforementioned first, second, third or fourth aspect.

In a twentieth aspect, the invention is directed to a method of inducing an immune response to an infectious disease or cancer comprising administering to a subject a polynucleotide encoding a hybrid antigen comprising an antigenic domain of an infectious agent or tumor antigen associated with the infectious disease or cancer, a heat shock protein binding domain, and a peptide linker there between from among Phe Phe Arg Lys (FFRK; SEQ ID NO:699); Phe Arg Lys (FRK); Phe Arg Lys Asn (FRKN, SEQ ID NO:701); Arg Lys Asn (RKN); Phe Phe Arg Lys Asn (FFRKN, SEQ ID NO:702); Phe Arg (FR), Gln Leu Lys (QLK), Gln Leu Glu (QLE), Ala Lys Val Leu (AKVL; SEQ ID NO:700); Lys Asn (KN); Arg Lys (RK); or $AA_1$-$AA_2$-$AA_3$-leucine (SEQ ID NO:9), wherein $AA_1$ is A, S, V, E, G, L, or K, preferably V, more preferably S, and most preferably A; $AA_2$ is K, V, or E, preferably E, more preferably V and most preferably K; and $AA_3$ is V, S, F, K, A, E, or T, preferably F, more preferably S and most preferably V. Among the foregoing, Gln Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred.

In a twenty-first aspect, the invention is directed a method of inducing an immune response to an infectious disease or cancer comprising administering to a subject a polynucleotide encoding a hybrid antigen as mentioned above, and a polynucleotide encoding a heat shock protein. In a preferred embodiment, the encoded heat shock protein is a hsp70.

In any or all of the aforementioned aspects of the invention, the infectious disease antigen may be derived from an infectious agent such as a bacterium, virus, protozoan, mycoplasma, fungus, yeast, parasite, or prion, by way of non-limiting example. A cancer or tumor antigen associated with cancer may be derived from a sarcoma, a lymphoma, a leukemia, or a carcinoma, a melanoma, carcinoma of the breast, carcinoma of the prostate, ovarian carcinoma, carcinoma of the cervix, colon carcinoma, carcinoma of the lung, glioblastoma, or astrocytoma, by way of non-limiting examples. The antigenic domain of an infectious agent or cancer comprises an antigen derived from or associated with the infectious disease or tumor antigen, such that induction of an immune response to the antigen of the infectious agent or cancer antigen, respectively, is useful for treating the corresponding infectious disease or cancer.

This application claims priority under 35 U.S.C. § 119(e) to provisional applications Ser. No. 60/462,469, filed Apr. 11, 2003; Ser. No. 60/463,746, filed Apr. 18, 2003; and Ser. No. 60/503,417, filed Sep. 16, 2003, all three of which are incorporated herein by reference in their entireties.

DETAILED DESCRIPTION OF THE INVENTION

Figure 1:
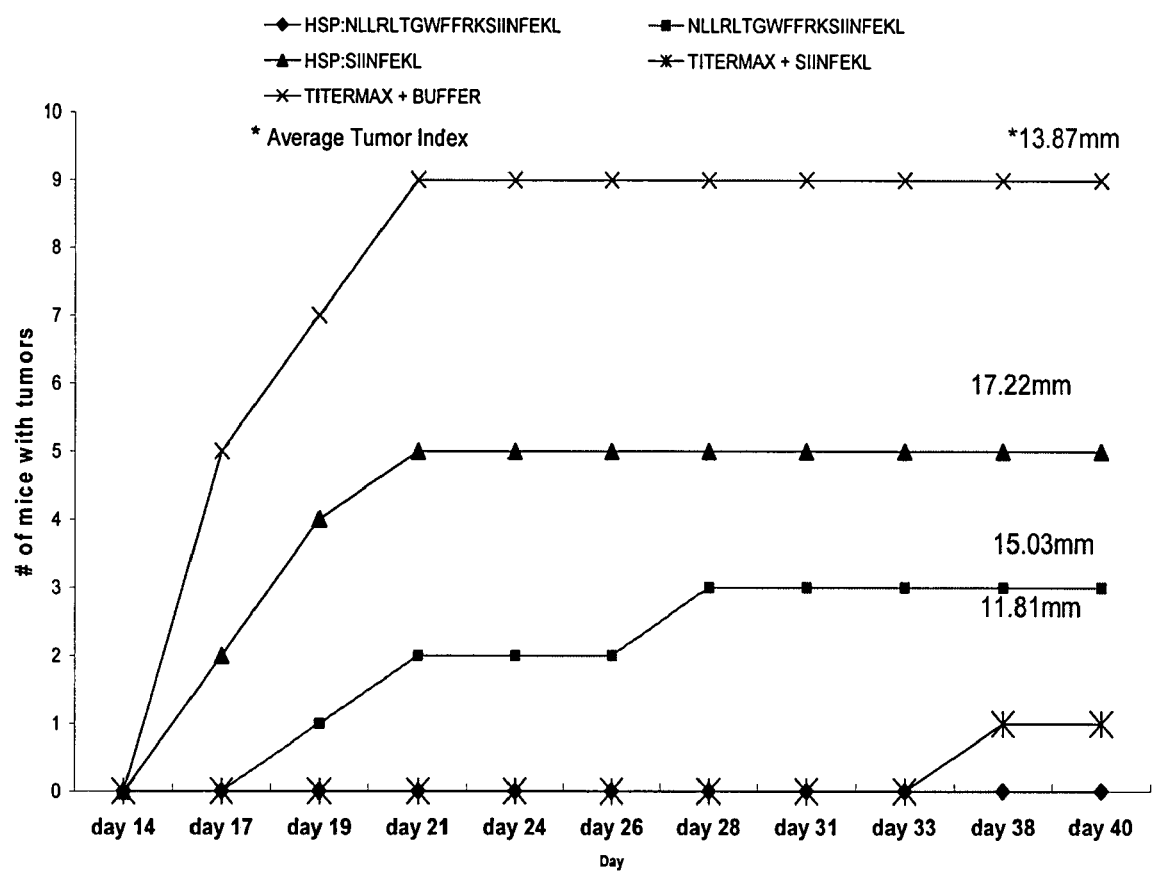
FIG. 1 shows the results of a tumor challenge study in which immunization using a hybrid antigen or complex of a hybrid antigen with a heat shock protein was performed, followed seven days later by challenge with a tumor expressing the antigen. In particular, the epitope SIINFEKL (SEQ ID NO:868) and the hybrid antigen NLLRLTGWFFRKSIINFEKL (SEQ ID NO:881) were assayed.

For purposes of clarity of description, and not by way of limitation, the detailed description is divided into the following subsections:
(i) hybrid antigens,
(ii) heat shock proteins; and
(iii) methods of administration.

Hybrid Antigens

A hybrid antigen, according to the invention comprises at least one antigenic (immunogenic) domain, at least one heat shock protein-binding domain, and a peptide linker between at least two of these domains, wherein the peptide linker is among Phe Phe Arg Lys (FFRK; SEQ ID NO:699),
Phe Arg Lys (FRK);
Phe Arg Lys Asn (FRKN, SEQ ID NO:701);
Arg Lys Asn (RKN);
Phe Phe Arg Lys Asn (FFRKN, SEQ ID NO:702);
Phe Arg (FR),
Gin Leu Lys (QLK),
Gin Leu Glu (QLE),
Ala Lys Val Leu (AKVL; SEQ ID NO:700),
Lys Asn (KN);
Arg Lys (RK); or
$AA_1$-$AA_2$-$AA_3$-leucine (SEQ ID NO:10), wherein $AA_1$ is A, S, V, E, G, L, or K,
preferably V, more preferably S, and most preferably A;
$AA_2$ is K, V, or E,
preferably E, more preferably V and most preferably K;
and $AA_3$ is V, S, F, K, A, E,
or T, preferably F, more preferably S and most preferably V.

Among the foregoing, Gln Leu Lys (QLK), Arg Lys (RK) and Ala Lys Val Leu (AKVL; SEQ ID NO:700) are preferred, and Phe Phe Arg Lys (FFRK; SEQ ID NO:699) is most preferred.

Thus, the hybrid antigen serves at least two functions, namely (i) it contains an epitope capable of inducing the desired immune response; and (ii) it is capable of physically binding to a heat shock protein. As will be noted below, such binding may occur in vivo such that administration of the hybrid antigen alone will induce the desired immune response and provide the desired therapeutic effect.

The term "antigen" as used herein, refers to a compound which may be composed of amino acids, carbohydrates, nucleic acids or lipids individually or in any combination.

The term "hybrid antigen," as used herein, refers to a compound which binds to one or more heat shock proteins and which is representative of the immunogen toward which an immune response is desirably directed. For example, where the immunogen is an influenza virus, the hybrid antigen may comprise a peptide fragment of the matrix protein of the influenza virus. As used herein, the term "immunogen" is applied to the neoplastic cell, infected cell, pathogen, or component thereof, towards which an immune response is to be elicited, whereas the hybrid antigen comprises a portion of that immunogen which can provoke the desired response and which binds to one or more heat shock proteins. In particular, the antigenic domain of the hybrid antigen is selected to elicit an immune response to a particular disease or pathogen, including peptides obtained from MHC molecules, mutated DNA gene products, and direct DNA products such as those obtained from tumor cells.

While the invention may be applied to any type of immunogen, immunogens of particular interest are those associated with, derived from, or predicted to be associated with a neoplastic disease, including but not limited to a sarcoma, a lymphoma, a leukemia, or a carcinoma, and in particular, with melanoma, carcinoma of the breast, carcinoma of the prostate, ovarian carcinoma, carcinoma of the cervix, colon carcinoma, carcinoma of the lung, glioblastoma, astrocytoma, etc. Selections of melanoma antigens useful in hybrid antigens of the present invention may be found, by way of non-limiting example, in PCT/US01/12449 (WO0178655), incorporated herein by reference in its entirety. Further, mutations of tumor suppressor gene products such as p53, or oncogene products such as ras may also provide hybrid antigens to be used according to the invention.

In further embodiments, the immunogen may be associated with an infectious disease, and, as such, may be a bacterium, virus, protozoan, mycoplasma, fungus, yeast, parasite, or prion. For example, but not by way of limitation, the immunogen may be a human papilloma virus (see below), a herpes virus such as herpes simplex or herpes zoster, a retrovirus such as human immunodeficiency virus 1 or 2, a hepatitis virus, an influenza virus, a rhinovirus, respiratory syncytial virus, cytomegalovirus, adenovirus, *Mycoplasma pneumoniae*, a bacterium of the genus *Salmonella, Staphylococcus, Streptococcus, Enterococcus, Clostridium, Escherichia, Klebsiella, Vibrio, Mycobacterium*, amoeba, a malarial parasite, *Trypanosoma cruzi*, etc.

Inmunogens may be obtained by isolation directly from a neoplasm, an infected cell, a specimen from an infected subject, a cell culture, or an organism culture, or may be synthesized by chemical or recombinant techniques. By way of non-limiting examples, suitable antigenic peptides, particularly for use in a hybrid antigen, for use against viruses, bacteria and the like can be designed by searching through their sequences for MHC class I restricted peptide epitopes containing HLA binding sequences such as but not limited to HLA-A2 peptide binding sequences:

Xaa(Leu/Met)XaaXaaXaa(VaV/Ile/Leu/Thr)XaaXaa(VaV-Leu) (SEQ ID NO:2), for example, from viruses:

```
Ser Gly Pro Ser Asn Thr Pro Pro Glu Ile;            (SEQ ID NO:10)

Ser Gly Val Glu Asn Pro Gly Gly Tyr Cys Leu;        (SEQ ID NO:11)

Lys Ala Val Tyr Asn Phe Ala Thr Cys Gly;            (SEQ ID NO:12)

Arg Pro Gln Ala Ser Gly Val Tyr Met;                (SEQ ID NO:13)

Phe Gln Pro Glu Asn Gly Glu Phe Ile;                (SEQ ID NO:14)

Ile Glu Gly Gly Trp Thr Gly Met Ile;                (SEQ ID NO:15)

Thr Tyr Val Ser Val Ser Thr Ser Thr Leu;            (SEQ ID NO:16)

Phe Glu Ala Asn Gly Asn Leu Ile;                    (SEQ ID NO:17)

Ile Tyr Ser Thr Val Ala Ser Ser Leu;                (SEQ ID NO:18)

Thr Tyr Gln Arg Thr Arg Ala Leu Val;                (SEQ ID NO:19)

Cys Thr Glu Leu Lys Leu Ser Asp Tyr;                (SEQ ID NO:20)

Ser Asp Tyr Glu Gly Arg Leu Ile;                    (SEQ ID NO:21)

Glu Glu Gly Ala Ile Val Gly Glu Ile;                (SEQ ID NO:22)

Val Ser Asp Gly Gly Pro Asn Leu Tyr;                (SEQ ID NO:23)

Ala Ser Asn Glu Asn Met Glu Thr Met;                (SEQ ID NO:24)

Ala Ser Asn Glu Asn Met Asp Ala Met;                (SEQ ID NO:25)

Lys Leu Gly Glu Phe Tyr Asn Glu Met Met;            (SEQ ID NO:26)

Leu Tyr Gln Asn Val Gly Thr Tyr Val;                (SEQ ID NO:27)

Thr Tyr Val Ser Val Gly Thr Ser Thr Leu;            (SEQ ID NO:28)

Phe Glu Ser Thr Gly Asn Leu Ile;                    (SEQ ID NO:29)

Val Tyr Glu Ile Leu Ala Ile Tyr Ala;                (SEQ ID NO:30)

Ile Tyr Ala Thr Val Ala Gly Ser Leu;                (SEQ ID NO:31)

Gly Ile Leu Gly Phe Val Phe Thr Leu;                (SEQ ID NO:32)

Ile Leu Gly Phe Val Phe Thr Leu Thr Val;            (SEQ ID NO:33)

Ile Leu Arg Gly Ser Val Ala His Lys;                (SEQ ID NO:34)

Glu Asp Leu Arg Val Leu Ser Phe Ile;                (SEQ ID NO:35)

Glu Leu Arg Ser Arg Tyr Trp Ala Ile;                (SEQ ID NO:36)

Ser Arg Tyr Trp Ala Ile Arg Thr Arg;                (SEQ ID NO:37)

Lys Thr Gly Gly Pro Ile Tyr Lys Arg;                (SEQ ID NO:38)

Phe Ala Pro Gly Asn Tyr Pro Ala Leu;                (SEQ ID NO:39)

Arg Arg Tyr Pro Asp Ala Val Tyr Leu;                (SEQ ID NO:40)

Asp Pro Val Ile Asp Arg Leu Tyr Leu;                (SEQ ID NO:41)
```

-continued

| | |
|---|---|
| Ser Pro Gly Arg Ser Phe Ser Tyr Phe; | (SEQ ID NO:42) |
| Tyr Pro Ala Leu Gly Leu His Glu Phe; | (SEQ ID NO:43) |
| Thr Tyr Lys Asp Thr Val Gln Leu; | (SEQ ID NO:44) |
| Phe Tyr Asp Gly Phe Ser Lys Val Pro Leu; | (SEQ ID NO:45) |
| Phe Ile Ala Gly Asn Ser Ala Tyr Glu Tyr Val; | (SEQ ID NO:46) |
| Tyr Pro His Phe Met Pro Thr Asn Leu; | (SEQ ID NO:47) |
| Ala Pro Thr Ala Gly Ala Phe Phe Phe; | (SEQ ID NO:48) |
| Ser Thr Leu Pro Glu Thr Thr Val Val Arg Arg; | (SEQ ID NO:49) |
| Phe Leu Pro Ser Asp Phe Phe Pro Ser Val; | (SEQ ID NO:50) |
| Trp Leu Ser Leu Leu Val Pro Phe Val; | (SEQ ID NO:51) |
| Gly Leu Ser Pro Thr Val Trp Leu Ser Val; | (SEQ ID NO:52) |
| Asp Leu Met Gly Tyr Ile Pro Leu Val; | (SEQ ID NO:53) |
| Leu Met Gly Tyr Ile Pro Leu Val Gly Ala; | (SEQ ID NO:54) |
| Ala Ser Arg Cys Trp Val Ala Met; | (SEQ ID NO:55) |
| Lys Leu Val Ala Leu Gly Ile Asn Ala Val; | (SEQ ID NO:56) |
| Phe Leu Arg Gly Arg Ala Tyr Gly Leu; | (SEQ ID NO:57) |
| Arg Arg Ile Tyr Asp Leu Ile Glu Leu; | (SEQ ID NO:58) |
| Ile Val Thr Asp Phe Ser Val Ile Lys; | (SEQ ID NO:59) |
| Arg Arg Arg Trp Arg Arg Leu Thr Val; | (SEQ ID NO:60) |
| Glu Glu Asn Leu Leu Asp Phe Val Arg Phe; | (SEQ ID NO:61) |
| Cys Leu Gly Gly Leu Leu Thr Met Val; | (SEQ ID NO:62) |
| Ser Ser Ile Glu Phe Ala Arg Leu; | (SEQ ID NO:63) |
| Leu Tyr Arg Thr Phe Ala Gly Asn Pro Arg Ala; | (SEQ ID NO:64) |
| Asp Tyr Ala Thr Leu Gly Val Gly Val; | (SEQ ID NO:65) |
| Leu Leu Leu Gly Thr Leu Asn Ile Val; | (SEQ ID NO:66) |
| Leu Leu Met Gly Thr Leu Gly Ile Val; | (SEQ ID NO:67) |
| Thr Leu Glu Asp Ile Val Leu His Leu; | (SEQ ID NO:68) |
| Gly Leu His Cys Tyr Glu Gln Leu Val; | (SEQ ID NO:69) |
| Pro Leu Lys Gln His Phe Gln Ile Val; | (SEQ ID NO:70) |
| Arg Leu Val Thr Leu Lys Asp Ile Val; | (SEQ ID NO:71) |
| Arg Ala His Tyr Asn Ile Val Thr Phe; | (SEQ ID NO:72) |
| Leu Leu Phe Gly Tyr Pro Val Tyr Val; | (SEQ ID NO:73) |
| Ser Ala Ile Asn Asn Tyr Ala Gln Lys Leu; | (SEQ ID NO:74) |
| His Glu Ala Ile Ser Pro Arg Thr Leu; | (SEQ ID NO:75) |
| Gln Met Val His Gln Ala Ile Ser Pro Arg Thr Leu; | (SEQ ID NO:76) |
| Cys Lys Gly Val Asn Lys Glu Tyr Leu; | (SEQ ID NO:77) |
| Glu Gly Ile Asn Asn Leu Asp Asn Leu; | (SEQ ID NO:78) |
| Asn Asn Leu Asp Asn Leu Arg Asp Tyr; | (SEQ ID NO:79) |
| Ser Glu Phe Leu Leu Glu Lys Arg Ile; | (SEQ ID NO:80) |
| Ser Tyr Ile Gly Ser Ile Asn Asn Ile; | (SEQ ID NO:81) |

-continued

| | |
|---|---|
| Ile Leu Gly Asn Lys Ile Val Arg Met Tyr; | (SEQ ID NO:82) |
| Arg Leu Arg Pro Gly Gly Lys Lys Lys; | (SEQ ID NO:83) |
| Glu Ile Lys Asp Thr Lys Glu Ala Leu; | (SEQ ID NO:84) |
| Gly Glu Ile Tyr Lys Arg Trp Ile Ile; | (SEQ ID NO:85) |
| Glu Ile Tyr Lys Arg Trp Ile Ile Leu; | (SEQ ID NO:86) |
| Arg Tyr Leu Lys Asp Gln Gln Leu Leu; | (SEQ ID NO:87) |
| Arg Gly Pro Gly Arg Ala Phe Val Thr Ile; | (SEQ ID NO:88) |
| Ile Val Gly Leu Asn Lys Ile Val Arg; | (SEQ ID NO:89) |
| Thr Val Tyr Tyr Gly Val Pro Val Trp Lys; | (SEQ ID NO:90) |
| Arg Leu Arg Asp Leu Leu Leu Ile Val Thr Arg; | (SEQ ID NO:91) |
| Lys Arg Trp Ile Ile Leu Gly Leu Asn Lys; | (SEQ ID NO:92) |
| Ser Phe Asn Cys Gly Gly Glu Phe Phe; | (SEQ ID NO:93) |
| Gly Arg Ala Phe Val Thr Ile Gly Lys; | (SEQ ID NO:94) |
| Thr Pro Gly Pro Gly Val Arg Tyr Pro Leu; | (SEQ ID NO:95) |
| Gln Val Pro Leu Arg Pro Met Thr Tyr Lys; | (SEQ ID NO:96) |
| Thr Glu Met Glu Lys Glu Gly Lys Ile; | (SEQ ID NO:97) |
| Ile Leu Lys Glu Pro Val His Gly Val; | (SEQ ID NO:98) |
| Val Glu Ala Glu Ile Ala His Glu Ile; | (SEQ ID NO:99) |
| Arg Gly Tyr Val Tyr Gln Gly Leu; | (SEQ ID NO:100) |
| Tyr Ser Gly Tyr Ile Phe Arg Asp Leu; | (SEQ ID NO:101) |
| Val Gly Pro Val Phe Pro Pro Gly Met; | (SEQ ID NO:102) |
| Ile Ile Tyr Arg Phe Leu Leu Ile;<br>from bacteria: | (SEQ ID NO:103) |
| Lys Tyr Gly Val Ser Val Gln Asp Ile; | (SEQ ID NO:104) |
| Ile Gln Val Gly Asn Thr Arg Thr Ile; | (SEQ ID NO:105) |
| Thr Pro His Pro Ala Arg Ile Gly Leu;<br>from parasites: | (SEQ ID NO:106) |
| Ser Tyr Ile Pro Ser Ala Glu Lys Ile; | (SEQ ID NO:107) |
| Lys Pro Lys Asp Glu Leu Asp Tyr; | (SEQ ID NO:108) |
| Lys Ser Lys Asp Glu Leu Asp Tyr; | (SEQ ID NO:109) |
| Lys Pro Asn Asp Lys Ser Leu Tyr; | (SEQ ID NO:110) |
| Lys Tyr Leu Lys Lys Ile Lys Asn Ser Leu; | (SEQ ID NO:111) |
| Tyr Glu Asn Asp Ile Glu Lys Lys Ile; | (SEQ ID NO:112) |
| Asn Tyr Asp Asn Ala Gly Thr Asn Leu; | (SEQ ID NO:113) |
| Asp Glu Leu Asp Tyr Glu Asn Asp Ile; | (SEQ ID NO:114) |
| Ser Tyr Val Pro Ser Ala Glu Gln Ile;<br>from cancers: | (SEQ ID NO:115) |
| Phe Glu Gln Asn Thr Ala Gln Pro; | (SEQ ID NO:116) |
| Phe Glu Gln Asn Thr Ala Gln Ala; | (SEQ ID NO:117) |
| Glu Ala Asp Pro Thr Gly His Ser Tyr; | (SEQ ID NO:118) |
| Glu Val Asp Pro Ile Gly His Leu Tyr; | (SEQ ID NO:119) |
| Ala Ala Gly Ile Gly Ile Leu Thr Val; | (SEQ ID NO:120) |

-continued

```
Tyr Leu Glu Pro Gly Pro Val Thr Ala;                        (SEQ ID NO:121)

Ile Leu Asp Gly Thr Ala Thr Leu Arg Leu;                    (SEQ ID NO:122)

Met Leu Leu Ala Leu Leu Tyr Cys Leu;                        (SEQ ID NO:123)

Tyr Met Asn Gly Thr Met Ser Glu Val;                        (SEQ ID NO:124)

Leu Pro Tyr Leu Gly Trp Leu Val Phe;                        (SEQ ID NO:125)

Phe Gly Pro Tyr Lys Leu Asn Arg Leu;                        (SEQ ID NO:126)

Lys Ser Pro Trp Phe Thr Thr Leu;                            (SEQ ID NO:127)

Gly Pro Pro His Ser Asn Asn Phe Gly Tyr;                    (SEQ ID NO:128)
and

Ile Ser Thr Gln Asn His Arg Ala Leu;                        (SEQ ID NO:129)
(Rammensee et at., Immunogenetics 41:178-223 (1995)), Xaa(Leu/Met)XaaXaaXaaXaaXaaXaaVal                           (SEQ ID NO:3)
(Tarpey et at., Immunology 81:222-227 (1994)), Xaa(Val/Gln)XaaXaaXaaXaaXaaXaaLeu,                          (SEQ ID NO:4)
for example, from virus:

Tyr Gly Ile Leu Gly Lys Val Phe Thr Leu;                    (SEQ ID NO:130)

Ser Leu Tyr Asn Thr Val Ala Thr Leu;                        (SEQ ID NO:131)
(Barouch et al., J. Exp. Med. 182:1847-1856 (1995)).
```

The foregoing epitopes are merely exemplary of selections available associated with various infectious diseases and cancer, and are provided without any intention whatsoever to be limiting.

It may also be desirable to consider the type of immune response which is desired. For example, under certain circumstances, a humoral immune response may be appropriate. In other cases, and indeed where an immune response directed toward neoplastic cells or infected cells is sought to be elicited, a cellular immune response is particularly desirable. Accordingly, particular epitopes associated with the activation of B cells, T helper cells, or cytotoxic T cells may be identified and selected for incorporation into the hybrid antigen.

It may also be desirable to utilize hybrid antigen associated with an autoimmune disease or allergy. Such a hybrid antigen may be administered, together with one or more heat shock proteins, in an amount sufficient to be tolerogenic or to inhibit a pre-existing immune response to the hybrid antigen in a subject. The amount of heat shock protein required to inhibit the immune response is expected to be substantially greater than the amount required for stimulation.

Although the size of hybrid antigen may vary depending upon the heat shock protein used, in non-limiting embodiments of the invention, the hybrid antigen may be the size of a peptide having between 10 and 500 amino acid residues, and preferably be the size of a peptide having between 14 and 100, most preferably 18 and 50 amino acid residues. As such, it may be desirable to produce a fragment of an immunogen to serve as the antigenic domain of a hybrid antigen, or, alternatively, to synthesize a hybrid antigen by chemical or recombinant DNA methods.

Based on the foregoing considerations, a hybrid antigen may be prepared, and then tested for its ability to bind to heat shock protein. In some instances, binding of hybrid antigen to a particular heat shock protein may be facilitated by the presence of at least one other protein, which may be a heat shock protein.

For example, binding of hybrid antigen to a heat shock protein may be evaluated by labeling the hybrid antigen with a detectable label, such as a radioactive, fluorescent, enzymatic or pigmented label, combining the hybrid antigen with heat shock protein under conditions which would be expected to permit binding to occur, and then isolating the heat shock protein while removing any unbound hybrid antigen, and determining whether any labeled hybrid antigen had adhered to the heat shock protein. As a specific example, and not by way of limitation, the ability of a hybrid antigen to bind to the heat shock protein BiP may be evaluated by combining 2 μg BiP with up to about 1150 pmole of radioactively labeled hybrid antigen in buffer containing 50 mM Tris HCl (pH 7.5), 200 mM NaCl, and 1 mM Na$_2$EDTA, in a final volume of 50 μl, for 30 minutes at 37 degrees Centigrade. Unbound hybrid antigen may then be removed from bound BiP-hybrid antigen by centrifugation at 100 g by desalting through a 1 ml Sephadex-G column for 2 minutes. Penefsky, *J. Biol. Chem.* 252:2891 (1977). To prevent binding to the resin, columns may first be treated with 100 μl of bovine serum albumin in the same buffer and centrifuged as above. Bound hybrid antigen may then be quantitated by liquid scintillation counting. See Flynn et al., *Science* 245:385-390 (1989).

Because ATP hydrolysis drives the release of peptides from many known heat shock proteins, the amount of ATPase activity may often be used to quantitate the amount of hybrid antigen binding to heat shock protein. An example of how such an assay may be performed is set forth in Flynn et al., *Science* 245:385-390 (1989).

The heat shock protein-binding domain is selected so that the hybrid antigen will bind in vitro or in vivo to a heat shock protein such as BiP, hsp70, gp96, or hsp90, or a member of the foregoing heat shock protein families, alone or in combination with accessory heat shock proteins such as hsp40, or hsp60.

Non-limiting examples of peptides which fulfill this criterion may be identified by panning libraries of antigens known to bind well to one or more heat shock proteins as described in Blond-Elguindi et al., *Cell* 75:717-728 (1993):

| | |
|---|---|
| Leu Phe Trp Pro Phe Glu Trp Ile; | (SEQ ID NO:132) |
| Asp Gly Val Gly Ser Phe Ile Gly; | (SEQ ID NO:133) |
| Glu Ser Leu Trp Asn Pro Gln Cys; | (SEQ ID NO:134) |
| Leu His Phe Asp Val Leu Trp Arg; | (SEQ ID NO:135) |
| Cys His Leu Lys Met Val Pro Trp; | (SEQ ID NO:136) |
| Asn Ser Val Leu Val Cys Glu Leu; | (SEQ ID NO:137) |
| Asp Arg Gly His Ser Thr Tyr Ser; | (SEQ ID NO:138) |
| Asp Val Trp Gly Trp Val Thr Trp; | (SEQ ID NO:139) |
| Ile Gln Phe Arg Val Glu Leu Phe; | (SEQ ID NO:140) |
| Leu Trp Leu Glu Leu Ser Leu Ser; | (SEQ ID NO:141) |
| Val Gly Ile Cys Ala Leu Phe Gly; | (SEQ ID NO:142) |
| Pro Tyr Pro Ser Gly Leu Asp Ser; | (SEQ ID NO:143) |
| Phe Trp Gly Val Leu Pro Tyr Pro; | (SEQ ID NO:144) |
| Phe Thr His Gly Ile Ser Leu Tyr; | (SEQ ID NO:145) |
| Asn His Ser Phe Gly Gly Ser Thr; | (SEQ ID NO:146) |
| Val Asp Tyr Val Tyr Phe His His; | (SEQ ID NO:147) |
| Phe Leu Asp Ile Ile Gly Tyr Gly; | (SEQ ID NO:148) |
| Trp Asp Asp Leu Leu His Gly Arg; | (SEQ ID NO:149) |
| Leu Arg Leu Leu Gly Thr Leu Asn; | (SEQ ID NO:150) |
| Phe Glu Gln His Asn Gln Glu Pro; | (SEQ ID NO:151) |
| Phe Val Gly Thr Val Thr Trp Ser; | (SEQ ID NO:152) |
| Leu Trp Ala Leu Thr Tyr Arg Gly; | (SEQ ID NO:153) |
| Ser Trp Gly Ser Asn Gly Gly Phe; | (SEQ ID NO:154) |
| Asp Met Trp Arg Arg Ala Val Gln; | (SEQ ID NO:155) |
| Cys Arg Val Ile Tyr His Ala Thr; | (SEQ ID NO:156) |
| Met Val Val Ala Arg Cys Gly His; | (SEQ ID NO:157) |
| His Met Trp Ile Asn Trp Val Gln; | (SEQ ID NO:158) |
| Cys Ala Gly Arg Cys Phe Gly Tyr; | (SEQ ID NO:159) |
| Cys Thr His Val Leu Ala Tyr Ser; | (SEQ ID NO:160) |
| Ser Trp Met Pro Trp Leu Thr Met; | (SEQ ID NO:161) |
| Leu Glu Trp Cys Ile Trp Arg Tyr; | (SEQ ID NO:162) |
| Cys Leu Ala Cys Ile Ile His Ser; | (SEQ ID NO:163) |
| Phe Trp Phe Pro Trp Asp Arg Ser; | (SEQ ID NO:164) |
| Trp Arg Thr Gly Val Phe His Gly; | (SEQ ID NO:165) |
| Met His Leu Arg Val Ala Asp Arg; | (SEQ ID NO:166) |
| Ala Leu Asp Leu Tyr Leu Tyr Val; | (SEQ ID NO:167) |

-continued

| | |
|---|---|
| Phe Phe Trp Phe Thr Leu Lys Glu; | (SEQ ID NO:168) |
| Leu Ser Phe Ala Gly Trp Gly Val; | (SEQ ID NO:169) |
| Met Met Met Leu Gly Arg Ala Pro; | (SEQ ID NO:170) |
| Trp Ser Phe Tyr Thr Trp Leu Asn; | (SEQ ID NO:171) |
| Phe Val Trp Met Arg Trp Ile Asp; | (SEQ ID NO:172) |
| Met Glu Val Asn Thr Pro Asp Asn; | (SEQ ID NO:173) |
| Phe Trp Gly Trp Leu Ile Pro Trp; | (SEQ ID NO:174) |
| Trp Gly Trp Val Trp Trp Asp; | (SEQ ID NO:175) |
| Trp Ile Phe Pro Trp Ile Glu Leu; | (SEQ ID NO:176) |
| Trp Met Phe Asn Trp Pro Trp Tyr; | (SEQ ID NO:177) |
| Met Asn Met Ile Val Leu Asp Lys; | (SEQ ID NO:178) |
| Phe Trp Gly Trp Pro Gly Trp Ser; | (SEQ ID NO:179) |
| Trp Leu Ile Arg Val Gly Thr Ala; | (SEQ ID NO:180) |
| Gly Leu Leu Thr His Leu Ile Trp; | (SEQ ID NO:181) |
| Leu Trp Trp Leu Asn Val His Gly; | (SEQ ID NO:182) |
| Trp Trp Trp Ile Asn Asp Glu Ser; | (SEQ ID NO:183) |
| Ala Asn Pro Ser Leu Ala Thr Tyr; | (SEQ ID NO:184) |
| Trp Leu Glu Gly Trp Trp Gly Trp; | (SEQ ID NO:185) |
| Met Met Pro Val Thr Ser Phe Arg; | (SEQ ID NO:186) |
| Gly Trp Met Asp Trp Trp Tyr Tyr; | (SEQ ID NO:187) |
| Leu Ala Ser Met Arg Asn Ser Met; | (SEQ ID NO:188) |
| Asp Leu Met Arg Trp Leu Gly Leu; | (SEQ ID NO:189) |
| Tyr Phe Tyr Ala Trp Trp Leu Asp; | (SEQ ID NO:190) |
| Leu Gly His Leu Trp Thr Glu Val; | (SEQ ID NO:191) |
| Leu Trp Trp Arg Asp Val Met Ala; | (SEQ ID NO:192) |
| Phe Ile Trp Trp Ala Pro Leu Ala; | (SEQ ID NO:193) |
| Gly Ser Val Gly Gly Gly Val Val; | (SEQ ID NO:194) |
| Asp Ser His Asp Asp Trp Arg Met; | (SEQ ID NO:195) |
| Phe Trp Arg Phe Asp Tyr Tyr Phe; | (SEQ ID NO:196) |
| Trp Thr Trp Trp Glu Trp Leu Ala; | (SEQ ID NO:197) |
| Trp Leu Trp Asp Trp Ile Val Val; | (SEQ ID NO:198) |
| Gly Trp Thr Trp Phe Phe Asp Met; | (SEQ ID NO:199) |
| Ala Trp Trp Gln His Phe Ile Val; | (SEQ ID NO:200) |
| Leu Trp Trp Asp Ile Ile Thr Gly; | (SEQ ID NO:201) |
| Phe Thr Tyr Gly Ser Arg Trp Leu; | (SEQ ID NO:202) |
| Phe Ser Leu Trp Pro Leu Ala Trp; | (SEQ ID NO:203) |
| Gly Ile Ile Leu Gly Tyr Asn Val; | (SEQ ID NO:204) |
| Ser Trp Met Thr Trp Ile Glu His; | (SEQ ID NO:205) |
| Gly Trp Trp Val Thr Trp Pro Trp; | (SEQ ID NO:206) |
| Val Val Ser Pro Trp Trp Leu Gly; | (SEQ ID NO:207) |

| | | |
|---|---|---|
| Asn Val Leu Ser Arg Gly Phe Ser; | (SEQ ID NO:208) |
| Ser Phe Glu Ser Leu Gly Gly Leu; | (SEQ ID NO:209) |
| Ile Thr Lys Gly Ser Ser Phe Pro; | (SEQ ID NO:210) |
| Leu Asp Trp Ala Arg Lys Leu Arg; | (SEQ ID NO:211) |
| Thr Ala Trp Asn Leu Leu Gly Tyr; | (SEQ ID NO:212) |
| Phe Gly Gln Gly Ile Lys His Val; | (SEQ ID NO:213) |
| Asp Val Val Trp Gln Arg Leu Leu; | (SEQ ID NO:214) |
| Tyr Val Asp Arg Phe Ile Gly Trp; | (SEQ ID NO:215) |
| Lys Met Ala Arg Pro Glu Gly Asn; | (SEQ ID NO:216) |
| Leu Gly Arg Trp Gly His Glu Ser; | (SEQ ID NO:217) |
| Ser Ile Trp Ser Leu Leu Val Leu; | (SEQ ID NO:218) |
| Val Trp Leu Asp Leu Leu Leu Ser; | (SEQ ID NO:219) |
| Tyr Leu Thr Asp Ser Leu Phe Gly; | (SEQ ID NO:220) |
| Thr Trp Trp Pro Ser Ile Thr Trp; | (SEQ ID NO:221) |
| Tyr Gly Leu Trp Trp Phe Pro Trp; | (SEQ ID NO:222) |
| Phe Ser Pro Ala Asp Thr Arg Tyr; | (SEQ ID NO:223) |
| Cys Asn Arg Leu Gln Ile Asp Cys; | (SEQ ID NO:224) |
| Ser Leu Val Ala Ala Arg Asn Leu; | (SEQ ID NO:225) |
| Phe Thr Ile His Asn Val Ala Val; | (SEQ ID NO:226) |
| Met Gly Pro Leu Gly Pro Leu Leu; | (SEQ ID NO:227) |
| Arg Gln Leu Ser Glu Leu Phe Val; | (SEQ ID NO:228) |
| Arg Val Val Cys Gln Ala Leu Leu; | (SEQ ID NO:229) |
| Trp Pro His Leu Trp Trp Leu Asp; | (SEQ ID NO:230) |
| Trp Met Asp Trp Val Trp His Thr; | (SEQ ID NO:231) |
| Trp Trp Gly Tyr Leu Ile Cys Gln; | (SEQ ID NO:232) |
| Phe Arg Gly Leu Ser Glu Gly Pro; | (SEQ ID NO:233) |
| Ser Trp Phe Asp Trp Leu Val Ala; | (SEQ ID NO:234) |
| Val Val Met Trp Tyr Ser Val Asp; | (SEQ ID NO:235) |
| Trp Gly Trp Ser Leu Ala Thr; | (SEQ ID NO:236) |
| Leu Gly Trp Phe Asp Arg Phe Phe; | (SEQ ID NO:237) |
| Ala Trp Trp Trp Pro Thr Tyr Val; | (SEQ ID NO:238) |
| Gly Phe Leu Ser Ser Trp Phe Leu; | (SEQ ID NO:239) |
| Gly Val Ile Asn Cys Ala Gly Thr; | (SEQ ID NO:240) |
| Val Cys Ala Arg Ala Ala His Leu; | (SEQ ID NO:241) |
| Gly Asn Ser Tyr Gly Asp Gly Gly; | (SEQ ID NO:242) |
| Gly Phe Leu Ser Ser Trp Phe Leu; | (SEQ ID NO:243) |
| Phe Asp Glu Pro Gly Arg Phe Leu; | (SEQ ID NO:244) |
| Arg Ser His Ala Thr Gly Val Val; | (SEQ ID NO:245) |
| Gly Tyr Trp Ala Met Met Ser Trp; | (SEQ ID NO:246) |
| Cys His Ser Met Trp Asp Gly Leu; | (SEQ ID NO:247) |
| Phe Ile Trp Arg Gly Trp Pro His; | (SEQ ID NO:248) |
| Leu Ser Phe Leu Gly Gly Arg Leu; | (SEQ ID NO:249) |
| Phe Ser Gly Val Arg Gln Pro Asn; | (SEQ ID NO:250) |
| Trp Gly Trp Met Pro Phe Tyr Tyr; | (SEQ ID NO:251) |
| Phe Thr Arg Pro Ala Val Val Asp; | (SEQ ID NO:252) |
| Asp Leu Trp Thr Trp Leu Gly Leu; | (SEQ ID NO:253) |
| Cys Asp Thr Ala Ala Val Ala Asp; | (SEQ ID NO:254) |
| Trp Trp Val Lys His His Met Leu; | (SEQ ID NO:255) |
| Ile Ala Phe Leu Arg Asp Asn Arg; | (SEQ ID NO:256) |
| Leu Ala Arg Pro Asp His Tyr Ser; | (SEQ ID NO:257) |
| Met Glu Ser Lys Arg Trp Thr Val; | (SEQ ID NO:258) |
| Met Ile Leu Lys Gly Tyr Ser Arg; | (SEQ ID NO:259) |
| Ala Pro Ser Asp Tyr Asp Glu Ser; | (SEQ ID NO:260) |
| His Trp Leu Arg Ser Lys Arg Thr; | (SEQ ID NO:261) |
| Gly Ala Arg Val Trp Asn Tyr Gln; | (SEQ ID NO:262) |
| Leu Ser Asn Trp Asn Met Arg Leu; | (SEQ ID NO:263) |
| Cys Gly Ala Ala Gln Gln Gly Met; and | (SEQ ID NO:264) |
| Gly Ser Ser Met Val Val Gln Arg. | (SEQ ID NO:265) |

Using this technique, Blond-Elguindi have concluded that the heat shock protein BiP recognizes polypeptides that contain a heptameric region having the sequence Hy(Trp/X)HyXHyXHy (SEQ ID NO:7)

where Hy represents a hydrophobic amino acid residue, particularly tryptophan, leucine or phenylalanine (SEQ ID NO:8), and X is any amino acid. High affinity heat-shock protein-binding sequences incorporating this motif include:

His Trp Asp Phe Ala Trp Pro Trp (SEQ ID NO:266); and
Phe Trp Gly Leu Trp Pro Trp Glu (SEQ ID NO:267).

Other heat shock protein binding motifs have also been identified. For example, Auger et al., *Nature Medicine* 2:306-310 (1996) have identified two pentapeptide binding motifs

| | |
|---|---|
| Gln Lys Arg Ala Ala | (SEQ ID NO:5) and |
| Arg Arg Arg Ala Ala | (SEQ ID NO:6) | in HLA-DR types associated with rheumatoid arthritis which bind to heat shock proteins. Heat shock binding motifs have also been identified as consisting of seven to fifteen residue long peptides which are enriched in hydrophobic amino acids.

Lys Arg Glu Ile Tyr Asp Leu Glu Met Asn Arg Leu Gly Lys;     (SEQ ID NO:269)

Leu Ser Ser Leu Phe Arg Pro Lys Arg Arg Pro Ile Tyr Lys Ser;
(SEQ ID NO:270)

Lys Leu Ile Gly Val Leu Ser Ser Leu Phe Arg Pro Lys;     (SEQ ID NO:271)

Arg Arg Pro Ile Tyr Lys Ser Asp Val Gly Met Ala His Phe Arg;  (SEQ ID NO:272)

Cys Lys Ile Glu Ser Thr Pro Val Lys Glu Ser;     (SEQ ID NO:273)

Tyr His Cys Asp Gly Phe Glu Asn Glu;     (SEQ ID NO:274)

Val Gly Ile Asp Leu Gly Thr Thr Tyr Ser Cys;     (SEQ ID NO:275)

Ser Asn Gly Ser Leu Glu Cys Arg Ile Cys     (SEQ ID NO:276)
(Flynn et al., Science 245: 385-390 (1989)), Moreover, other heat shock protein binding peptides include:

Gly Lys Trp Val Tyr Ile;     (SEQ ID NO:277)

Ala Lys Arg Glu Thr Lys;     (SEQ ID NO:278)

Lys Trp Val His Leu Phe;     (SEQ ID NO:279)

Arg Leu Val Leu Val Leu;     (SEQ ID NO:280)

Trp Lys Trp Gly Ile Tyr;     (SEQ ID NO:281)

Ser Ser His Ala Ser Ala;     (SEQ ID NO:282)

Trp Gly Pro Trp Ser Phe;     (1 SEQ ID NO:283)

Ala Ile Pro Gly Lys Val;     (SEQ ID NO:284)

Arg Val His Asp Pro Ala;     (SEQ ID NO:285)

Arg Ser Val Ser Ser Phe;     (SEQ ID NO:286)

Leu Gly Thr Arg Lys Gly;     (SEQ ID NO:287)

Lys Asp Pro Leu Phe Asn;     (SEQ ID NO:288)

Leu Ser Glu His Thr Asn;     (SEQ ID NO:289)

Asn Arg Leu Leu Leu Thr;     (SEQ ID NO:290)

Tyr Pro Leu Trp Val Ile;     (SEQ ID NO:291)

Leu Leu Ile Ile Asp Arg;     (SEQ ID NO:292)

Arg Val Ile Ser Leu Glu;     (SEQ ID NO:293)

Glu Val Ser Arg Glu Asp;     (SEQ ID NO:294)

Ser Ile Leu Arg Ser Thr;     (SEQ ID NO:295)

Pro Gly Leu Val Trp Leu;     (4 SEQ ID NO:296)

Val Lys Lys Leu Tyr Ile;     (SEQ ID NO:297)

Asn Asn Arg Leu Leu Asp;     (SEQ ID NO:298)

Ser Lys Gly Arg Trp Gly;     (SEQ ID NO:299)

Ile Arg Pro Ser Gly Ile;     (SEQ ID NO:300)

Ala Ser Leu Cys Pro Thr;     (SEQ ID NO:301)

Asp Val Pro Gly Leu Arg;     (SEQ ID NO:302)

Arg His Arg Glu Val Glu;     (SEQ ID NO:303)

Leu Ala Arg Lys Arg Ser;     (SEQ ID NO:304)

-continued

| | |
|---|---|
| Ser Val Leu Asp His Val; | (SEQ ID NO:305) |
| Asn Leu Leu Arg Arg Ala; | (SEQ ID NO:306) |
| Ser Gly Ile Ser Ala Trp; | (SEQ ID NO:307) |
| Phe Tyr Phe Trp Val Arg; | (SEQ ID NO:308) |
| Lys Leu Phe Leu Pro Leu; | (S SEQ ID NO:309) |
| Thr Pro Thr Leu Ser Asp; | (SEQ ID NO:310) |
| Thr His Ser Leu Ile Leu; | (SEQ ID NO:311) |
| Leu Leu Leu Leu Ser Arg; | (SEQ ID NO:312) |
| Leu Leu Arg Val Arg Ser; | (SEQ ID NO:313) |
| Glu Arg Arg ser Arg Gly; | (SEQ ID NO:314) |
| Arg Met Leu Glu Leu Ala; | (SEQ ID NO:315) |
| Age Gly Trp Ala Asn Ser; | (SEQ ID NO:316) |
| Arg Pro Phe Tyr Ser Tyr; | (SEQ ID NO:317) |
| Ser Ser Ser Trp Asn Ala; | (SEQ ID NO:318) |
| Leu Gly His Leu Glu Glu; | (SEQ ID NO:319) |
| Ser Ala Val Thr Asn Thr; | (SEQ ID NO:320) |
| Leu Arg Arg Ala Ser Leu; | (SEQ ID NO:321) |
| Leu Arg Arg Trp Ser Leu; | (SEQ ID NO:322) |
| Lys Trp Val His Leu Phe; | (SEQ ID NO:323) |
| Asn Arg Leu Leu Leu Thr; | (SEQ ID NO:324) |
| Ala Arg Leu Leu Leu Thr; | (SEQ ID NO:325) |
| Asn Ala Leu Leu Leu Thr; | (SEQ ID NO:326) |
| Asn Arg Leu Ala Leu Thr; | (SEQ ID NO:327) |
| Asn Leu Leu Arg Leu Thr; | (SEQ ID NO:328) |
| Asn Arg Leu Trp Leu Thr; | (SEQ ID NO:329) |
| Asn Arg Leu Leu Leu Ala; | (SEQ ID NO:330) |
| Met Glu Glu Arg Ile Thr Leu Lys Asp Tyr Ala Met; | (SEQ ID NO:331) |
| Leu Arg Arg Trp Ser Leu Gly; | (SEQ ID NO:332; |
| Lys Trp Val His Leu Phe Gly; | (SEQ ID NO:333) |
| Asn Arg Leu Leu Leu Thr Gly; | (SEQ ID NO:334) |
| Ala Arg Leu Leu Leu Thr Gly; | (SEQ ID NO:335) |
| Asn Ala Leu Leu Leu Thr Gly; | (SEQ ID NO:336) |
| Asn Arg Leu Ala Leu Thr Gly; | (SEQ ID NO:337) |
| Asn Leu Leu Arg Leu Thr Gly; | (SEQ ID NO:338) |
| Asn Arg Leu Trp Leu Thr Gly; | (SEQ ID NO:339) |
| Asn Arg Leu Leu Leu Ala Gly; | (SEQ ID NO:340) |
| Gly Lys Trp Val Tyr Ile Gly; | (SEQ ID NO:341) |
| Ala Lys Arg Glu Thr Lys Gly; | (SEQ ID NO:342) |
| Lys Trp Val His Leu Phe Gly; | (SEQ ID NO:343) |
| Arg Leu Val Leu Val Leu Gly; | (SEQ ID NO:344) |

-continued

| | |
|---|---|
| Trp Lys Trp Gly Ile Tyr; | (SEQ ID NO:345) |
| Ser Ser His Ala Ser Ala; | (SEQ ID NO:346) |
| Trp Gly Pro Trp Ser Phe; | (SEQ ID NO:347) |
| Ala Ile Pro Gly Lys Val; | (SEQ ID NO:348) |
| Arg Val His Asp Pro Ala Gly; | (SEQ ID NO:349) |
| Arg Ser Val Ser Ser Phe Gly; | (SEQ ID NO:350) |
| Leu Gly Thr Arg Lys Gly Gly; | (SEQ ID NO:351) |
| Lys Asp Pro Leu Phe Asn Gly; | (SEQ ID NO:352) |
| Leu Ser Glu His Thr Asn Gly; | (SEQ ID NO:353) |
| Asn Arg Leu Leu Leu Thr Gly; | (SEQ ID NO:354) |
| Tyr Pro Leu Trp Val Ile Gly; | (SEQ ID NO:355) |
| Leu Leu Ile Ile Asp Arg Gly; | (SEQ ID NO:356) |
| Arg Val Ile Ser Leu Glu Gly; | (SEQ ID NO:357) |
| Glu Val Ser Arg Glu Asp Gly; | (SEQ ID NO:358) |
| Ser Ile Leu Arg Ser Thr Gly; | (SEQ ID NO:359) |
| Pro Gly Leu Val Trp Leu Gly; | (SEQ ID NO:360) |
| Val Lys Lys Leu Tyr Ile Gly; | (SEQ ID NO:361) |
| Asn Asn Arg Leu Leu Asp Gly; | (SEQ ID NO:362) |
| Ser Lys Gly Arg Trp Gly Gly; | (SEQ ID NO:363) |
| Ile Arg Pro Ser Gly Ile Gly; | (SEQ ID NO:364) |
| Ala Ser Leu Cys Pro Thr Gly; | (SEQ ID NO:365) |
| Asp Val Pro Gly Leu Arg Gly; | (SEQ ID NO:366) |
| Arg His Arg Glu Val Glu Gly; | (SEQ ID NO:367) |
| Leu Ala Arg Lys Arg Ser Gly; | (SEQ ID NO:368) |
| Ser Val Leu Asp His Val Gly; | (SEQ ID NO:369) |
| Asn Leu Leu Arg Arg Ala Gly; | (SEQ ID NO:370) |
| Ser Gly Ile Ser Ala Trp Gly; | (SEQ ID NO:371) |
| Phe Tyr Phe Trp Val Arg Gly; | (SEQ ID NO:372) |
| Lys Leu Phe Leu Pro Leu Gly; | (SEQ ID NO:373) |
| Thr Pro Thr Leu Ser Asp Gly; | (SEQ ID NO:374) |
| Thr His Ser Leu Ile Leu Gly; | (SEQ ID NO:375) |
| Leu Leu Leu Leu Ser Arg Gly; | (SEQ ID NO:376) |
| Leu Leu Arg Val Arg Ser Gly; | (SEQ ID NO:377) |
| Glu Arg Arg ser Arg Gly Gly; | (SEQ ID NO:378) |
| Arg Met Leu Glu Leu Ala Gly; | (SEQ ID NO:379) |
| Age Gly Trp Ala Asn Ser Gly; | (SEQ ID NO:380) |
| Arg Pro Phe Tyr Ser Tyr Gly; | (SEQ ID NO:381) |
| Ser Ser Ser Trp Asn Ala Gly; | (SEQ ID NO:382) |

Leu Gly His Leu Glu Glu Gly;    (SEQ ID NO:383)
and

Ser Ala Val Thr Asn Thr Gly;    (SEQ ID NO:384)

as described by Gragerov et al., J. Molec. Biol. 235:848-854 (1994).

Other heat shock protein binding domains include Phe Tyr Gln Leu Ala Leu Thr (SEQ ID NO:385), Phe Tyr Gln Leu Ala Leu Thr Trp (SEQ ID NO:386), Arg Lys Leu Phe Phe Asn Leu Arg (SEQ ID NO:387), Arg Lys Leu Phe Phe Asn Leu Arg Trp (SEQ ID NO:388), Lys Phe Glu Arg Gln (SEQ ID NO:389), Asn Ile Val Arg Lys Lys Lys (SEQ ID NO:390), and Arg Gly Tyr Val Tyr Gln Gly Leu (SEQ ID NO:391).

Moreover, other heat shock protein binding domains include those described in WO9922761. Xaa represents any amino acid.

```
HTTVYGAG;       (SEQ ID NO:392)
TETPYPTG;       (SEQ ID NO:393)
LTTPFSSG;       (SEQ ID NO:394)
GVPLTMDG;       (SEQ ID NO:395)
KLPTVLRG;       (SEQ ID NO:396)
CRFHGNRG;       (SEQ ID NO:397)
YTRDFEAG;       (SEQ ID NO:398)
SSAAGPRG;       (SEQ ID NO:399)
SLIQYSRG;       (SEQ ID NO:400)
DALMWP Xaa G;   (SEQ ID NO:401)
SS Xaa SLYIG;   (SEQ ID NO:402)
FNTSTRTG;       (SEQ ID NO:403)
TVQHVAFG;       (SEQ ID NO:404)
DYSFPPLG;       (SEQ ID NO:405)
VGSMESLG;       (SEQ ID NO:406)
F Xaa PMI Xaa SG; (SEQ ID NO:407)
APPRVTMG;       (SEQ ID NO:408)
IATKTPKG;       (SEQ ID NO:409)
KPPLFQIG;       (SEQ ID NO:410)
YHTAHNMG;       (SEQ ID NO:411)
SYIQATHG;       (SEQ ID NO:412)
SSFATFLG;       (SEQ ID NO:413)
TTPPNFAG;       (SEQ ID NO:414)
ISLDPRMG;       (SEQ ID NO:415)
SLPLFGAG;       (SEQ ID NO:416)
NLLKTTLG;       (SEQ ID NO:417)
DQNLPRRG;       (SEQ ID NO:418)
SHFEQLLG;       (SEQ ID NO:419)
TPQLHHGG;       (SEQ ID NO:420)
APLDRITG;       (SEQ ID NO:421)
FAPLIAHG;       (SEQ ID NO:422)
SWIQTFMG;       (SEQ ID NO:423)
NTWPHMYG;       (SEQ ID NO:424)
EPLPTTLG;       (SEQ ID NO:425)
HGPHLFNG;       (SEQ ID NO:426)
YLNSTLAG;       (SEQ ID NO:427)
HLHSPSGG;       (SEQ ID NO:428)
TLPHRLNG;       (SEQ ID NO:429)
SSPREVHG;       (SEQ ID NO:430)
NQVDTARG;       (SEQ ID NO:431)
YPTPLLTG;       (SEQ ID NO:432)
HPAAFPWG;       (SEQ ID NO:433)
LLPHSSAG;       (SEQ ID NO:434)
LETYTASG;       (SEQ ID NO:435)
KYVPLPPG;       (SEQ ID NO:436)
APLALHAG;       (SEQ ID NO:437)
YESLLTKG;       (SEQ ID NO:438)
SHAASGTG;       (SEQ ID NO:439)
GLATVKSG;       (SEQ ID NO:440)
GATSFGLG;       (SEQ ID NO:441)
KPPGPVSG;       (SEQ ID NO:442)
TLYVSGNG;       (SEQ ID NO:443)
HAPFKSQG;       (SEQ ID NO:444)
VAFTRLPG;       (SEQ ID NO:445)
LPTRTPAG;       (SEQ ID NO:446)
ASFDLLIG;       (SEQ ID NO:447)
RMNTEPPG;       (SEQ ID NO:448)
KMTPLTTG;       (SEQ ID NO:449)
ANATPLLG;       (SEQ ID NO:450)
TIWPPPVG;       (SEQ ID NO:451)
QTKVMTTG;       (SEQ ID NO:452)
NHAVFASG;       (SEQ ID NO:453)
LHAA Xaa TSG;   (SEQ ID NO:454)
```

TWQPYFHG; (SEQ ID NO:455)
APLALHAG; (SEQ ID NO:456)
TAHDLTVG; (SEQ ID NO:457)
NMTNMLTG; (SEQ ID NO:458)
GSGLSQDG; (SEQ ID NO:459)
TPIKTIYG; (SEQ ID NO:460)
SHLYRSSG; (SEQ ID NO:461)
YTLVQPL; (SEQ ID NO:462)
TPDITPK; (SEQ ID NO:463)
TYPDLRY; (SEQ ID NO:464)
DRTHATS; (SEQ ID NO:465)
MSTTFYS; (SEQ ID NO:466)
YQHAVQT; (SEQ ID NO:467)
FPFSAST; (SEQ ID NO:468)
SSFPPLD; (SEQ ID NO:469)
MAPSPPH; (SEQ ID NO:470)
SSFPDLL; (SEQ ID NO:471)
HSYNRLP; (SEQ ID NO:472)
HLTHSQR; (SEQ ID NO:473)
QAAQSRS; (SEQ ID NO:474)
FATHHIG; (SEQ ID NO:475)
SMPEPLI; (SEQ ID NO:476)
IPRYHLI; (SEQ ID NO:477)
SAPHMTS; (SEQ ID NO:478)
KAPVWAS; (SEQ ID NO:479)
LPHWLLI; (SEQ ID NO:480)
ASAGYQI; (SEQ ID NO:481)
VTPKTGS; (SEQ ID NO:482)
EHPMPVL; (SEQ ID NO:483)
VSSFVTS; (SEQ ID NO:484)
STHFTWP; (SEQ ID NO:485)
GQWWSPD; (SEQ ID NO:486)
GPPHQDS; (SEQ ID NO:487)
NTLPSTI; (SEQ ID NO:488)
HQPSRWV; (SEQ ID NO:489)
YGNPLQP; (SEQ ID NO:490)
FHWWQP; (SEQ ID NO:491)
ITLKYPL; (SEQ ID NO:492)
FHWPWLF; (SEQ ID NO:493)
TAQDSTG; (SEQ ID NO:494)
FHWWQP; (SEQ ID NO:495)
FHWWDWW; (SEQ ID NO:496)
EPFFRMQ; (SEQ ID NO:497)
TWWLNYR; (SEQ ID NO:498)
FHWWQP; (SEQ ID NO:499)
QPSHLRW; (SEQ ID NO:500)
SPASPVY; (SEQ ID NO:501)
FHWWQP; (SEQ ID NO:502)
HPSNQAS; (SEQ ID NO:503)
NSAPRPV; (SEQ ID NO:504)
QLWSIYP; (SEQ ID NO:505)
SWPFFDL; (SEQ ID NO:506)
DTTLPLH; (SEQ ID NO:507)
WHWQMLW; (SEQ ID NO:508)
DSFRTPV; (SEQ ID NO:509)
TSPLSLL; (SEQ ID NO:510)
AYNYVSD; (SEQ ID NO:511)
RPLHDPM; (SEQ ID NO:512)
WPSTTLF; (SEQ ID NO:513)
ATLEPVR; (SEQ ID NO:514)
SMTVLRP; (SEQ ID NO:515)
QIGAPSW; (SEQ ID NO:516)
APDLYVP; (SEQ ID NO:517)
RMPPLLP; (SEQ ID NO:518)
AKATPEH; (SEQ ID NO:519)
TPPLRIN; (SEQ ID NO:520)
LPIHAPH; (SEQ ID NO:521)
DLNAYTH; (SEQ ID NO:522)
VTLPNFH; (SEQ ID NO:523)
NSRLPTL; (SEQ ID NO:524)
YPHPSRS; (SEQ ID NO:525)
GTAHFMY; (SEQ ID NO:526)
YSLLPTR; (SEQ ID NO:527)
LPRRTLL; (SEQ ID NO:528)
TSTLLWK; (SEQ ID NO:529)
TSDMKPH; (SEQ ID NO:530)
TSSYLAL; (SEQ ID NO:531)
NLYGPHD; (SEQ ID NO:532)
LETYTAS; (SEQ ID NO:533)
AYKSLTQ; (SEQ ID NO:534)

-continued

| | |
|---|---|
| STSVYSS; | (SEQ ID NO:535) |
| EGPLRSP; | (SEQ ID NO:536) |
| TTYHALG; | (SEQ ID NO:537) |
| VSIGHPS; | (SEQ ID NO:538) |
| THSHRPS; | (SEQ ID NO:539) |
| ITNPLTT; | (SEQ ID NO:540) |
| SIQAHHS; | (SEQ ID NO:541) |
| LNWPRVL; | (SEQ ID NO:542) |
| YYYAPPP; | (SEQ ID NO:543) |
| SLWTRLP; | (SEQ ID NO:544) |
| NVYHSSL; | (SEQ ID NO:545) |
| NSPHPPT; | (SEQ ID NO:546) |
| VPAKPRH; | (SEQ ID NO:547) |
| HNLHPNR; | (SEQ ID NO:548) |
| YTTHRWL; | (SEQ ID NO:549) |
| AVTAAIV; | (SEQ ID NO:550) |
| TLMHDRV; | (SEQ ID NO:551) |
| TPLKVPY; | (SEQ ID NO:552) |
| FTNQQYH; | (SEQ ID NO:553) |
| SHVPSMA; | (SEQ ID NO:554) |
| HTTVYGA; | (SEQ ID NO:555) |
| TETPYPT; | (SEQ ID NO:556) |
| LTTPFSS; | (SEQ ID NO:557) |
| GVPLTMD; | (SEQ ID NO:558) |
| KLPTVLR; | (SEQ ID NO:559) |
| CRFHGNR; | (SEQ ID NO:560) |
| YTRDFEA; | (SEQ ID NO:561) |
| SSAAGPR; | (SEQ ID NO:562) |
| SLIQYSR; | (SEQ ID NO:563) |
| DALMWP Xaa; | (SEQ ID NO:564) |
| SS Xaa SLYI; | (SEQ ID NO:565) |
| FNTSTRT; | (SEQ ID NO:566) |
| TVQHVAF; | (SEQ ID NO:567) |
| DYSFPPL; | (SEQ ID NO:568) |
| VGSMESL; | (SEQ ID NO:569) |
| F Xaa PMI Xaa S; | (SEQ ID NO:570) |
| APPRVTM; | (SEQ ID NO:571) |
| IATKTPK; | (SEQ ID NO:572) |
| KPPLFQI; | (SEQ ID NO:573) |
| YHTAHNM; | (SEQ ID NO:574) |

-continued

| | |
|---|---|
| SYIQATH; | (SEQ ID NO:575) |
| SSFATFL; | (SEQ ID NO:576) |
| TTPPNFA; | (SEQ ID NO:577) |
| ISLDPRM; | (SEQ ID NO:578) |
| SLPLFGA; | (SEQ ID NO:579) |
| NLLKTTL; | (SEQ ID NO:580) |
| DQNLPRR; | (SEQ ID NO:581) |
| SHFEQLL; | (SEQ ID NO:582) |
| TPQLHHG; | (SEQ ID NO:583) |
| APLDRIT; | (SEQ ID NO:584) |
| FAPLIAH; | (SEQ ID NO:585) |
| SWIQTFM; | (SEQ ID NO:586) |
| NTWPHMY; | (SEQ ID NO:587) |
| EPLPTTL; | (SEQ ID NO:588) |
| HGPHLFN; | (SEQ ID NO:589) |
| YLNSTLA; | (SEQ ID NO:590) |
| HLHSPSG; | (SEQ ID NO:591) |
| TLPHRLN; | (SEQ ID NO:592) |
| SSPREVH; | (SEQ ID NO:593) |
| NQVDTAR; | (SEQ ID NO:594) |
| YPTPLLT; | (SEQ ID NO:595) |
| HPAAFPW; | (SEQ ID NO:596) |
| LLPHSSA; | (SEQ ID NO:597) |
| LETYTAS; | (SEQ ID NO:598) |
| KYVPLPP; | (SEQ ID NO:599) |
| APLALHA; | (SEQ ID NO:600) |
| YESLLTK; | (SEQ ID NO:601) |
| SHAASGT; | (SEQ ID NO:602) |
| GLATVKS; | (SEQ ID NO:603) |
| GATSFGL; | (SEQ ID NO:604) |
| KPPGPVS; | (SEQ ID NO:605) |
| TLYVSGN; | (SEQ ID NO:606) |
| HAPFKSQ; | (SEQ ID NO:607) |
| VAFTRLP; | (SEQ ID NO:608) |
| LPTRTPA; | (SEQ ID NO:609) |
| ASFDLLI; | (SEQ ID NO:610) |
| RMNTEPP; | (SEQ ID NO:611) |
| KMTPLTT; | (SEQ ID NO:612) |
| ANATPLL; | (SEQ ID NO:613) |
| TIWPPPV; | (SEQ ID NO:614) |

```
QTKVMTT;      (SEQ ID NO:615)

NHAVFAS;      (SEQ ID NO:616)

LHAA Xaa TS;  (SEQ ID NO:617)

TWQPYFH;      (SEQ ID NO:618)

APLALHA;      (SEQ ID NO:619)

TAHDLTV;      (SEQ ID NO:620)

NMTNMLT;      (SEQ ID NO:621)

GSGLSQD;      (SEQ ID NO:622)

TPIKTIY;      (SEQ ID NO:623)

SHLYRSS;      (SEQ ID NO:624)

HGQAWQF;      (SEQ ID NO:625)
and

FHWWW.        (SEQ ID NO:626)
```

The aforementioned heat shock protein binding domains are merely exemplary of various peptides, among peptide and non-peptide heat shock protein binding molecules, that may be used in the practice of the present invention. In other embodiments, the heat shock protein binding domain may be directed to bind to a different part of the mammalian heat shock protein that those aforementioned, and the heat shock protein-binding domains of the invention are not limited to binding to any particular portion of the heat shock protein molecule. In a non-limiting example, the peptide IFAGIKK-KAERADLIAYLKQATAK (Greene et al., 1995, J. Biol. Chem. 270:2967-2973; SEQ ID NO:627) or a heat shock protein-binding fragment of this peptide, is used in any of the conjugates of the invention to facilitate the binding of a pre-selected molecule to a heat shock protein. In addition to the aforementioned peptides that bind to heat shock proteins, the binding may be achieved through the use of an organic molecule or compound with heat shock protein binding activity. For example, suitable molecules include members of the benzoquinone ansamycin antibiotics, such as herbimycin A, geldanamycin, macmimycin I, mimosamycin, and kuwaitimycin (Omura et al., 1979, J. Antibiotics 32:255-261; see also WO9922761, incorporated by reference herein in its entirety), or structurally related compounds, and analogs or derivatives thereof. These molecules may be conjugated though established chemical means to the antigenic domains of the invention, via the peptide linker, to produce hybrid antigens capable of binding to a heat shock protein in vitro or in vivo and eliciting an immune response to the antigen present therein.

As described in co-pending and commonly-owned application Ser. No. 10/776,521, filed Feb. 12, 2004, incorporated herein by reference in its entirety, it has been found that incorporation of a tryptophan residue (Trp, or single amino acid code W) at the C-terminus of the heat shock protein binding domains such as but not limited to those identified as described above, enhances binding to heat shock proteins. Increased binding to heat shock proteins has been found to increase the ability of hybrid antigens to induce an immune response to the antigenic domain of the hybrid antigen, whether administered in a complex with a heat shock protein or when administered alone. Increased immune response is correlated with increased efficacy of treating disease. Other examples of methods for determining affinity are described in PCT/US96/13363 (WO9706821), which is incorporated herein by reference in its entirety.

Among the foregoing selection of heat shock protein binding domains, those preferred in the present invention as part of a hybrid antigen comprising an antigenic domain and peptide linker of the invention there between includes the following heat shock protein binding domains:

```
Gly Lys Trp Val Tyr Ile Gly Trp;    (SEQ ID NO:628)

Ala Lys Arg Glu Thr Lys Gly Trp;    (SEQ ID NO:629)

Lys Trp Val His Leu Phe Gly Trp;    (SEQ ID NO:630)

Arg Leu Val Leu Val Leu Gly Trp;    (SEQ ID NO:631)

Trp Lys Trp Gly Ile Tyr Gly Trp;    (SEQ ID NO:632)

Ser Ser His Ala Ser Ala Gly Trp;    (SEQ ID NO:633)

Trp Gly Pro Trp Ser Phe Gly Trp;    (SEQ ID NO:634)

Ala Ile Pro Gly Lys Val Gly Trp;    (SEQ ID NO:635)

Arg Val His Asp Pro Ala Gly Trp;    (SEQ ID NO:636)

Arg Ser Val Ser Ser Phe Gly Trp;    (SEQ ID NO:637)

Leu Gly Thr Arg Lys Gly Gly Trp;    (SEQ ID NO:638)

Lys Asp Pro Leu Phe Asn Gly Trp;    (SEQ ID NO:639)

Leu Ser Glu His Thr Asn Gly Trp;    (SEQ ID NO:640)
```

-continued

Asn Arg Leu Leu Leu Thr Gly Trp; (SEQ ID NO:641)

Tyr Pro Leu Trp Val Ile Gly Trp; (SEQ ID NO:642)

Leu Leu Ile Ile Asp Arg Gly Trp; (SEQ ID NO:643)

Arg Val Ile Ser Leu Glu Gly Trp; (SEQ ID NO:644)

Glu Val Ser Arg Glu Asp Gly Trp; (SEQ ID NO:645)

Ser Ile Leu Arg Ser Thr Gly Trp; (SEQ ID NO:646)

Pro Gly Leu Val Trp Leu Gly Trp; (SEQ ID NO:647)

Val Lys Lys Leu Tyr Ile Gly Trp; (SEQ ID NO:648)

Asn Asn Arg Leu Leu Asp Gly Trp; (SEQ ID NO:649)

Ser Lys Gly Arg Trp Gly Gly Trp; (SEQ ID NO:650)

Ile Arg Pro Ser Gly Ile Gly Trp; (SEQ ID NO:651)

Ala Ser Leu Cys Pro Thr Gly Trp; (SEQ ID NO:652)

Asp Val Pro Gly Leu Arg Gly Trp; (SEQ ID NO:653)

Arg His Arg Glu Val Glu Gly Trp; (SEQ ID NO:654)

Leu Ala Arg Lys Arg Ser Gly Trp; (SEQ ID NO:655)

Ser Val Leu Asp His Val Gly Trp; (SEQ ID NO:656)

Asn Leu Leu Arg Arg Ala Gly Trp; (SEQ ID NO:657)

Ser Gly Ile Ser Ala Trp Gly Trp; (SEQ ID NO:658)

Phe Tyr Phe Trp Val Arg Gly Trp; (SEQ ID NO:659)

Lys Leu Phe Leu Pro Leu Gly Trp; (SEQ ID NO:660)

Thr Pro Thr Leu Ser Asp Gly Trp; (SEQ ID NO:661)

Thr His Ser Leu Ile Leu Gly Trp; (SEQ ID NO:662)

Leu Leu Leu Leu Ser Arg Gly Trp; (SEQ ID NO:663)

Leu Leu Arg Val Arg Ser Gly Trp; (SEQ ID NO:664)

Glu Arg Arg ser Arg Gly Gly Trp; (SEQ ID NO:665)

Arg Met Leu Glu Leu Ala Gly Trp; (SEQ ID NO:666)

Age Gly Trp Ala Asn Ser Gly Trp; (SEQ ID NO:667)

Arg Pro Phe Tyr Ser Tyr Gly Trp; (SEQ ID NO:668)

Ser Ser Ser Trp Asn Ala Gly Trp; (SEQ ID NO:669)

Leu Gly His Leu Glu Glu Gly Trp; (SEQ ID NO:670)

Ser Ala Val Thr Asn Thr Gly Trp; (SEQ ID NO:671)

Phe Tyr Glu Leu Ala Leu Thr; (SEQ ID NO:672)

Phe Tyr Glu Leu Ala Leu Thr Trp, (SEQ ID NO:673)

Arg Lys Leu Phe Phe Asn Leu Arg, (SEQ ID NO:674)

Arg Lys Leu Phe Phe Asn Leu Arg Trp, (SEQ ID NO:675)

Lys Phe Glu Arg Glu, (SEQ ID NO:676)

Asn Ile Val Arg Lys Lys Lys, (SEQ ID NO:677)
and

Arg Gly Tyr Val Tyr Glu Gly Leu. (SEQ ID NO:678)

Other non-limiting examples of such heat shock protein binding domains with a terminal Trp residue useful for the various aspects of the present invention include:

Asn Leu Leu Arg Leu Thr Gly Trp; (SEQ ID NO:679)
Phe Tyr Glu Leu Ala Leu Tyr Trp; (SEQ ID NO:680)
Arg Lys Leu Phe Phe Asn Leu Arg Trp; (SEQ ID NO:681)
Gly Lys Trp Val Tyr Ile Gly Trp; (SEQ ID NO:628)
Ala Lys Arg Glu Thr Lys Gly Trp; (SEQ ID NO:629)
Lys Trp Val His Leu Phe Gly Trp; (SEQ ID NO:630)
Arg Leu Val Leu Val Leu Gly Trp; (SEQ ID NO:631)
Trp Lys Trp Gly Ile Tyr Gly Trp; (SEQ ID NO:632)
Ser Ser His Ala Ser Ala Gly Trp; (SEQ ID NO:633)
Trp Gly Pro Trp Ser Phe Gly Trp; (SEQ ID NO:634)
Ala Ile Pro Gly Lys Val Gly Trp; (SEQ ID NO:635)
Arg Val His Asp Pro Ala Gly Trp; (SEQ ID NO:636)
Arg Ser Val Ser Ser Phe Gly Trp; (SEQ ID NO:637)
Leu Gly Thr Arg Lys Gly Gly Trp; (SEQ ID NO:638)
Lys Asp Pro Leu Phe Asn Gly Trp; (SEQ ID NO:639)
Leu Ser Glu His Thr Asn Gly Trp; (SEQ ID NO:640)
Asn Arg Leu Leu Leu Thr Gly Trp; (SEQ ID NO:641)
Tyr Pro Leu Trp Val Ile Gly Trp; (SEQ ID NO:642)
Leu Leu Ile Ile Asp Arg Gly Trp; (SEQ ID NO:643)
Arg Val Ile Ser Leu Glu Gly Trp; (SEQ ID NO:644)
Glu Val Ser Arg Glu Asp Gly Trp; (SEQ ID NO:645)
Ser Ile Leu Arg Ser Thr Gly Trp; (SEQ ID NO:646)
Pro Gly Leu Val Trp Leu Gly Trp; (SEQ ID NO:647)
Val Lys Lys Leu Tyr Ile Gly Trp; (SEQ ID NO:648)
Asn Asn Arg Leu Leu Asp Gly Trp; (SEQ ID NO:649)
Ser Lys Gly Arg Trp Gly Gly Trp; (SEQ ID NO:650)
Ile Arg Pro Ser Gly Ile Gly Trp; (SEQ ID NO:651)
Ala Ser Leu Cys Pro Thr Gly Trp; (SEQ ID NO:652)
Asp Val Pro Gly Leu Arg Gly Trp; (SEQ ID NO:653)
Arg His Arg Glu Val Glu Gly Trp; (SEQ ID NO:654)
Leu Ala Arg Lys Arg Ser Gly Trp; (SEQ ID NO:655)
Ser Val Leu Asp His Val Gly Trp; (SEQ ID NO:656)
Asn Leu Leu Arg Arg Ala Gly Trp; (SEQ ID NO:657)
Ser Gly Be Ser Ala Trp Gly Trp; (SEQ ID NO:658)
Phe Tyr Phe Trp Val Arg Gly Trp; (SEQ ID NO:659)
Lys Leu Phe Leu Pro Leu Gly Trp; (SEQ ID NO:660)
Thr Pro Thr Leu Ser Asp Gly Trp; (SEQ ID NO:661)
Thr His Ser Leu Ile Leu Gly Trp; (SEQ ID NO:662)

-continued

Leu Leu Leu Leu Ser Arg Gly Trp; (SEQ ID NO:663)
Leu Leu Arg Val Arg Ser Gly Trp; (SEQ ID NO:664)
Glu Arg Arg ser Arg Gly Gly Trp; (SEQ ID NO:665)
Arg Met Leu Glu Leu Ala Gly Trp; (SEQ ID NO:666)
Age Gly Trp Ala Asn Ser Gly Trp; (SEQ ID NO:667)
Arg Pro Phe Tyr Ser Tyr Gly Trp; (SEQ ID NO:668)
Ser Ser Ser Trp Asn Ala Gly Trp; (SEQ ID NO:669)
Leu Gly His Leu Glu Glu Gly Trp; (SEQ ID NO:670)
Ser Ala Val Thr Asn Thr Gly Trp; (SEQ ID NO:671)
Leu Arg Arg Ala Ser Leu Trp; (SEQ ID NO:682)
Leu Arg Arg Trp Ser Leu Trp; (SEQ ID NO:683)
Lys Trp Val His Leu Phe Trp; (SEQ ID NO:684)
Asn Arg Leu Leu Leu Thr Trp; (SEQ ID NO:685)
Ala Arg Leu Leu Leu Thr Trp; (SEQ ID NO:686)
Asn Ala Leu Leu Leu Thr Trp; (SEQ ID NO:687)
Asn Arg Leu Ala Leu Thr Trp; (SEQ ID NO:688)
Asn Leu Leu Arg Leu Thr Trp; (SEQ ID NO:689)
Asn Arg Leu Trp Leu Thr Trp; (SEQ ID NO:690)
and
Asn Arg Leu Leu Leu Ala Trp. (SEQ ID NO:691)

Other heat shock protein binding domains useful in the practice of the present invention include Phe Tyr Gln Leu Ala Leu Thr Trp (SEQ ID NO:692), Phe Tyr Gln Leu Ala Leu Thr Trp (SEQ ID NO:693), Arg Lys Leu Phe Phe Asn Leu Arg Trp (SEQ ID NO:694), Arg Lys Leu Phe Phe Asn Leu Arg Trp (SEQ ID NO:695), Lys Phe Glu Arg Gln Trp (SEQ ID NO:696), Asn Ile Val Arg Lys Lys Trp (SEQ ID NO:697), and Arg Gly Tyr Val Tyr Gln Gly Leu Trp (SEQ ID NO:698).

Moreover, other heat shock protein binding domains include those described in WO9922761, and may have a terminal Trp residue added to achieve the purposes of the present invention. Xaa represents any amino acid.

Tyr Thr Leu Val Gln Pro Leu Trp; (SEQ ID NO:703)
Thr Pro Asp Ile Thr Pro Lys Trp; (SEQ ID NO:704)
Thr Tyr Pro Asp Leu Arg Tyr Trp; (SEQ ID NO:705)
Asp Arg Thr His Ala Thr Ser Trp; (SEQ ID NO:706)
Met Ser Thr Thr Phe Tyr Ser Trp; (SEQ ID NO:707)
Tyr Gln His Ala Val Gln Thr Trp; (SEQ ID NO:708)
Phe Pro Phe Ser Ala Ser Thr Trp; (SEQ ID NO:709)
Ser Ser Phe Pro Pro Leu Asp Trp; (SEQ ID NO:710)
Met Ala Pro Ser Pro His Trp; (SEQ ID NO:711)
Ser Ser Phe Pro Asp Leu Leu Trp; (SEQ ID NO:712)
His Ser Tyr Asn Arg Leu Pro Trp; (SEQ ID NO:713)

| | |
|---|---|
| His Leu Thr His Ser Gln Arg Trp; | (SEQ ID NO:714) |
| Gln Ala Ala Gln Ser Arg Ser Trp; | (SEQ ID NO:715) |
| Phe Ala Thr His His Ile Gly Trp; | (SEQ ID NO:716) |
| Ser Met Pro Glu Pro Leu Ile Trp; | (SEQ ID NO:717) |
| Ile Pro Arg Tyr His Leu Ile Trp; | (SEQ ID NO:718) |
| Ser Ala Pro His Met Thr Ser Trp; | (SEQ ID NO:719) |
| Lys Ala Pro Val Trp Ala Ser Trp; | (SEQ ID NO:720) |
| Leu Pro His Trp Leu Leu Ile Trp; | (SEQ ID NO:721) |
| Ala Ser Ala Gly Tyr Gln Ile Trp; | (SEQ ID NO:722) |
| Val Thr Pro Lys Thr Gly Ser Trp; | (SEQ ID NO:723) |
| Glu His Pro Met Pro Val Leu Trp; | (SEQ ID NO:724) |
| Val Ser Ser Phe Val Thr Ser Trp; | (SEQ ID NO:725) |
| Ser Thr His Phe Thr Trp Pro Trp; | (SEQ ID NO:726) |
| Gly Gln Trp Trp Ser Pro Asp Trp; | (SEQ ID NO:727) |
| Gly Pro Pro His Gln Asp Ser Trp; | (SEQ ID NO:728) |
| Asn Thr Leu Pro Ser Thr Ile Trp; | (SEQ ID NO:729) |
| His Gln Pro Ser Arg Trp Val Trp; | (SEQ ID NO:730) |
| Tyr Gly Asn Pro Leu Gln Pro Trp; | (SEQ ID NO:731) |
| Phe His Trp Trp Trp Gln Pro Trp; | (SEQ ID NO:732) |
| Ile Thr Leu Lys Tyr Pro Leu Trp; | (SEQ ID NO:733) |
| Phe His Trp Pro Trp Leu Phe Trp; | (SEQ ID NO:734) |
| Thr Ala Gln Asp Ser Thr Gly Trp; | (SEQ ID NO:735) |
| Phe His Trp Trp Trp Gln Pro Trp; | (SEQ ID NO:736) |
| Phe His Trp Trp Asp Trp Trp Trp; | (SEQ ID NO:737) |
| Glu Pro Phe Phe Arg Met Gln Trp; | (SEQ ID NO:738) |
| Thr Trp Trp Leu Asn Tyr Arg Trp; | (SEQ ID NO:739) |
| Phe His Trp Trp Trp Gln Pro Trp; | (SEQ ID NO:740) |
| Gln Pro Ser His Leu Arg Trp Trp; | (SEQ ID NO:741) |
| Ser Pro Ala Ser Pro Val Tyr Trp; | (SEQ ID NO:742) |
| Phe His Trp Trp Trp Gln Pro Trp; | (SEQ ID NO:743) |
| His Pro Ser Asn Gln Ala Ser Trp; | (SEQ ID NO:744) |
| Asn Ser Ala Pro Arg Pro Val Trp; | (SEQ ID NO:745) |
| Gln Leu Trp Ser Ile Tyr Pro Trp; | (SEQ ID NO:746) |
| Ser Trp Pro Phe Phe Asp Leu Trp; | (SEQ ID NO:747) |
| Asp Thr Thr Leu Pro Leu His Trp; | (SEQ ID NO:748) |
| Trp His Trp Gln Met Leu Trp Trp; | (SEQ ID NO:749) |
| Asp Ser Phe Arg Thr Pro Val Trp; | (SEQ ID NO:750) |
| Thr Ser Pro Leu Ser Leu Leu Trp; | (SEQ ID NO:751) |
| Ala Tyr Asn Tyr Val Ser Asp Trp; | (SEQ ID NO:752) |
| Arg Pro Leu His Asp Pro Met Trp; | (SEQ ID NO:753) |
| Trp Pro Ser Thr Thr Leu Phe Trp; | (SEQ ID NO:754) |
| Ala Thr Leu Glu Pro Val Arg Trp; | (SEQ ID NO:755) |
| Ser Met Thr Val Leu Arg Pro Trp; | (SEQ ID NO:756) |
| Gln Ile Gly Ala Pro Ser Trp Trp; | (SEQ ID NO:757) |
| Ala Pro Asp Leu Tyr Val Pro Trp; | (SEQ ID NO:758) |
| Arg Met Pro Pro Leu Leu Pro Trp; | (SEQ ID NO:759) |
| Ala Lys Ala Thr Pro Glu His Trp; | (SEQ ID NO:760) |
| Thr Pro Pro Leu Arg Ile Asn Trp; | (SEQ ID NO:761) |
| Leu Pro Ile His Ala Pro His Trp; | (SEQ ID NO:762) |
| Asp Leu Asn Ala Tyr Thr His Trp; | (SEQ ID NO:763) |
| Val Thr Leu Pro Asn Phe His Trp; | (SEQ ID NO:764) |
| Asn Ser Arg Leu Pro Thr Leu Trp; | (SEQ ID NO:765) |
| Tyr Pro His Pro Ser Arg Ser Trp; | (SEQ ID NO:766) |
| Gly Thr Ala His Phe Met Tyr Trp; | (SEQ ID NO:767) |
| Tyr Ser Leu Leu Pro Thr Arg Trp; | (SEQ ID NO:768) |
| Leu Pro Arg Arg Thr Leu Leu Trp; | (SEQ ID NO:769) |
| Thr Ser Thr Leu Leu Trp Lys Trp; | (SEQ ID NO:770) |
| Thr Ser Asp Met Lys Pro His Trp; | (SEQ ID NO:771) |
| Thr Ser Ser Tyr Leu Ala Leu Trp; | (SEQ ID NO:772) |
| Asn Leu Tyr Gly Pro His Asp Trp; | (SEQ ID NO:773) |
| Leu Glu Thr Tyr Thr Ala Ser Trp; | (SEQ ID NO:774) |
| Ala Tyr Lys Ser Leu Thr Gln Trp; | (SEQ ID NO:775) |
| Ser Thr Ser Val Tyr Ser Ser Trp; | (SEQ ID NO:776) |
| Glu Gly Pro Leu Arg Ser Pro Trp; | (SEQ ID NO:777) |
| Thr Thr Tyr His Ala Leu Gly Trp; | (SEQ ID NO:778) |
| Val Ser Ile Gly His Pro Ser Trp; | (SEQ ID NO:779) |
| Thr His Ser His Arg Pro Ser Trp; | (SEQ ID NO:780) |
| Ile Thr Asn Pro Leu Thr Thr Trp; | (SEQ ID NO:781) |
| Ser Ile Gln Ala His His Ser Trp; | (SEQ ID NO:782) |
| Leu Asn Trp Pro Arg Val Leu Trp; | (SEQ ID NO:783) |
| Tyr Tyr Tyr Ala Pro Pro Pro Trp; | (SEQ ID NO:784) |
| Ser Leu Trp Thr Arg Leu Pro Trp; | (SEQ ID NO:785) |
| Asn Val Tyr His Ser Ser Leu Trp; | (SEQ ID NO:786) |
| Asn Ser Pro His Pro Pro Thr Trp; | (SEQ ID NO:787) |
| Val Pro Ala Lys Pro Arg His Trp; | (SEQ ID NO:788) |
| His Asn Leu His Pro Asn Arg Trp; | (SEQ ID NO:789) |
| Tyr Thr Thr His Arg Trp Leu Trp; | (SEQ ID NO:790) |
| Ala Val Thr Ala Ala Ile Val Trp; | (SEQ ID NO:791) |
| Thr Leu Met His Asp Arg Val Trp; | (SEQ ID NO:792) |
| Thr Pro Leu Lys Val Pro Tyr Trp; | (SEQ ID NO:793) |

| | |
|---|---|
| Phe Thr Asn Gln Gln Tyr His Trp; | (SEQ ID NO:794) |
| Ser His Val Pro Ser Met Ala Trp; | (SEQ ID NO:795) |
| His Thr Thr Val Tyr Gly Ala Trp; | (SEQ ID NO:796) |
| Thr Glu Thr Pro Tyr Pro Thr Trp; | (SEQ ID NO:797) |
| Leu Thr Thr Pro Phe Ser Ser Trp; | (SEQ ID NO:798) |
| Gly Val Pro Leu Thr Met Asp Trp; | (SEQ ID NO:799) |
| Lys Leu Pro Thr Val Leu Arg Trp; | (SEQ ID NO:800) |
| Cys Arg Phe His Gly Asn Arg Trp; | (SEQ ID NO:801) |
| Tyr Thr Arg Asp Phe Glu Ala Trp; | (SEQ ID NO:802) |
| Ser Ser Ala Ala Gly Pro Arg Trp; | (SEQ ID NO:803) |
| Ser Leu Ile Gln Tyr Ser Arg Trp; | (SEQ ID NO:804) |
| Asp Ala Leu Met Trp Pro XAA Trp; | (SEQ ID NO:805) |
| Ser Ser XAA Ser Leu Tyr Ile Trp; | (SEQ ID NO:806) |
| Phe Asn Thr Ser Thr Arg Thr Trp; | (SEQ ID NO:807) |
| Thr Val Gln His Val Ala Phe Trp; | (SEQ ID NO:808) |
| Asp Tyr Ser Phe Pro Pro Leu Trp; | (SEQ ID NO:809) |
| Val Gly Ser Met Glu Ser Leu Trp; | (SEQ ID NO:810) |
| Phe XAA Pro Met Ile XAA Ser Trp; | (SEQ ID NO:811) |
| Ala Pro Pro Arg Val Thr Met Trp; | (SEQ ID NO:812) |
| Ile Ala Thr Lys Thr Pro Lys Trp; | (SEQ ID NO:813) |
| Lys Pro Pro Leu Phe Gln Ile Trp; | (SEQ ID NO:814) |
| Tyr His Thr Ala His Asn Met Trp; | (SEQ ID NO:815) |
| Ser Tyr Ile Gln Ala Thr His Trp; | (SEQ ID NO:816) |
| Ser Ser Phe Ala Thr Phe Leu Trp; | (SEQ ID NO:817) |
| Thr Thr Pro Pro Asn Phe Ala Trp; | (SEQ ID NO:818) |
| Ile Ser Leu Asp Pro Arg Met Trp; | (SEQ ID NO:819) |
| Ser Leu Pro Leu Phe Gly Ala Trp; | (SEQ ID NO:820) |
| Asn Leu Leu Lys Thr Thr Leu Trp; | (SEQ ID NO:821) |
| Asp Gln Asn Leu Pro Arg Arg Trp; | (SEQ ID NO:822) |
| Ser His Phe Glu Gln Leu Leu Trp; | (SEQ ID NO:823) |
| Thr Pro Gln Leu His His Gly Trp; | (SEQ ID NO:824) |
| Ala Pro Leu Asp Arg Ile Thr Trp; | (SEQ ID NO:825) |
| Phe Ala Pro Leu Ile Ala His Trp; | (SEQ ID NO:826) |
| Ser Trp Ile Gln Thr Phe Met Trp; | (SEQ ID NO:827) |
| Asn Thr Trp Pro His Met Tyr Trp; | (SEQ ID NO:828) |
| Glu Pro Leu Pro Thr Thr Leu Trp; | (SEQ ID NO:829) |
| His Gly Pro His Leu Phe Asn Trp; | (SEQ ID NO:830) |
| Tyr Leu Asn Ser Thr Leu Ala Trp; | (SEQ ID NO:831) |
| His Leu His Ser Pro Ser Gly Trp; | (SEQ ID NO:832) |
| Thr Leu Pro His Arg Leu Asn Trp; | (SEQ ID NO:833) |
| Ser Ser Pro Arg Glu Val His Trp; | (SEQ ID NO:834) |
| Asn Gln Val Asp Thr Ala Arg Trp; | (SEQ ID NO:835) |
| Tyr Pro Thr Pro Leu Leu Thr Trp; | (SEQ ID NO:836) |
| His Pro Ala Ala Phe Pro Trp Trp; | (SEQ ID NO:837) |
| Leu Leu Pro His Ser Ser Ala Trp; | (SEQ ID NO:838) |
| Leu Glu Thr Tyr Thr Ala Ser Trp; | (SEQ ID NO:839) |
| Lys Tyr Val Pro Leu Pro Pro Trp; | (SEQ ID NO:840) |
| Ala Pro Leu Ala Leu His Ala Trp; | (SEQ ID NO:841) |
| Tyr Glu Ser Leu Leu Thr Lys Trp; | (SEQ ID NO:842) |
| Ser His Ala Ala Ser Gly Thr Trp; | (SEQ ID NO:843) |
| Gly Leu Ala Thr Val Lys Ser Trp; | (SEQ ID NO:844) |
| Gly Ala Thr Ser Phe Gly Leu Trp; | (SEQ ID NO:845) |
| Lys Pro Pro Gly Pro Val Ser Trp; | (SEQ ID NO:846) |
| Thr Leu Tyr Val Ser Gly Asn Trp; | (SEQ ID NO:847) |
| His Ala Pro Phe Lys Ser Gln Trp; | (SEQ ID NO:848) |
| Val Ala Phe Thr Arg Leu Pro Trp; | (SEQ ID NO:849) |
| Leu Pro Thr Arg Thr Pro Ala Trp; | (SEQ ID NO:850) |
| Ala Ser Phe Asp Leu Leu Ile Trp; | (SEQ ID NO:851) |
| Arg Met Asn Thr Glu Pro Pro Trp; | (SEQ ID NO:852) |
| Lys Met Thr Pro Leu Thr Thr Trp; | (SEQ ID NO:853) |
| Ala Asn Ala Thr Pro Leu Leu Trp; | (SEQ ID NO:854) |
| Thr Ile Trp Pro Pro Pro Val Trp; | (SEQ ID NO:855) |
| Gln Thr Lys Val Met Thr Thr Trp; | (SEQ ID NO:856) |
| Asn His Ala Val Phe Ala Ser Trp; | (SEQ ID NO:857) |
| Leu His Ala Ala Xaa Thr Ser Trp; | (SEQ ID NO:858) |
| Thr Trp Gln Pro Tyr Phe His Trp; | (SEQ ID NO:859) |
| Ala Pro Leu Ala Leu His Ala Trp; | (SEQ ID NO:860) |
| Thr Ala His Asp Leu Thr Val Trp; | (SEQ ID NO:861) |
| Asn Met Thr Asn Met Leu Thr Trp; | (SEQ ID NO:862) |
| Gly Ser Gly Leu Ser Gln Asp Trp; | (SEQ ID NO:863) |
| Thr Pro Ile Lys Thr Ile Tyr Trp; | (SEQ ID NO:864) |
| Ser His Leu Tyr Arg Ser Ser Trp; and | (SEQ ID NO:865) |
| His Gly Gln Ala Trp Gln Phe Trp; | (SEQ ID NO:866). |

Among all of the foregoing heat shock protein binding peptides, the heat shock protein binding domain Asn Leu Leu Arg Leu Thr Gly Trp (SEQ ID NO:867) is most preferred in the hybrid antigens of the invention. However, the aforementioned heat shock protein binding domains are merely exemplary of various moieties, among peptide and non-peptide heat shock protein binding molecules, that may be used in the practice of the present invention.

The hybrid antigen of the invention incorporates at least one antigenic (immunogenic) domain and at least one one heat shock protein-binding domain, separated by at least one peptide linker as described herein. The hybrid antigen of the invention may be synthesized using chemical peptide synthesis methods or it can be synthesized by expression of a nucleic acid construct containing linked sequences encoding the antigenic and heat shock protein binding domains. One suitable technique utilizes initial separate PCR amplification reactions to produce separate DNA segments encoding the two domains, each with a linker segment attached to one end, followed by fusion of the two amplified products in a further PCR step. This technique is referred to as linker tailing. Suitable restriction sites may also be engineered into regions of interest, after which restriction digestion and ligation is used to produce the desired hybrid antigen-encoding sequence.

As noted herein, the nucleic acid encoding a hybrid antigen of the invention is also suitable for therapeutic use by administration to the subject, where expression in vivo yields the hybrid antigen with the ability of inducing an immune response.

Heat Shock Proteins

The term "heat shock protein," as used herein, refers to any protein which exhibits increased expression in a cell when the cell is subjected to a stress. In preferred non-limiting embodiments, the heat shock protein is originally derived from a eukaryotic cell; in more preferred embodiments, the heat shock protein is originally derived from a mammalian cell. For example, but not by way of limitation, heat shock proteins which may be used according to the invention include BiP (also referred to as grp78), hsp70, hsc70, gp96 (grp94), hsp60, hsp40, and hsp90, and members of the families thereof. Especially preferred heat shock proteins are BiP, gp96, and hsp70, as exemplified below. Most preferred is a member of the hsp70family. Naturally occurring or recombinantly derived mutants of heat shock proteins may also be used according to the invention. For example, but not by way of limitation, the present invention provides for the use of heat shock proteins mutated so as to facilitate their secretion from the cell (for example having mutation or deletion of an element which facilitates endoplasmic reticulum recapture, such as KDEL (SEQ ID NO:266) or its homologues; such mutants are described in PCT Application No. PCT/US96/13233 (WO 97/06685), which is incorporated herein by reference).

For embodiments of the invention wherein heat shock protein and hybrid antigen are directly administered to the subject in the form of a protein/peptide complex, the heat shock protein may be prepared, using standard techniques, from natural sources, for example as described in Flynn et al., Science 245:385-390 (1989), or using recombinant techniques such as expression of a heat shock encoding vector in a suitable host cell such as a bacterial, yeast or mammalian cell. If pre-loading of the heat shock protein with peptides from the host organism is a concern, the heat shock protein can be incubated with ATP and then repurified. Non-limiting examples of methods for preparing recombinant heat shock proteins are set forth below.

A nucleic acid encoding a heat shock protein may be operatively linked to elements necessary or desirable for expression and then used to express the desired heat shock protein as either a means to produce heat shock protein for use in a protein vaccine or, alternatively, in a nucleic acid vaccine. Elements necessary or desirable for expression include, but are not limited to, promoter/enhancer elements, transcriptional start and stop sequences, polyadenylation signals, translational start and stop sequences, ribosome binding sites, signal sequences and the like. For example, but not by way of limitation, genes for various heat shock proteins have been cloned and sequenced, including, but not limited to, gp96 (human: Genebank Accession No. X15187; Maki et al., Proc. Natl. Acad. Sci. U.S.A. 87:5658-5562 (1990); mouse: Genebank Accession No. M16370; Srivastava et al., Proc. Natl. Acad. Sci. U.S.A. 84:3807-3811 (1987)), BiP (mouse: Genebank Accession No. U16277; Haas et al., Proc. Natl. Acad. Sci. U.S.A. 85:2250-2254 (1988); human: Genebank Accession No. M19645; Ting et al., DNA 7:275-286 (1988)), hsp70(mouse: Genebank Accession No. M35021; Hunt et al., Gene 87:199-204 (1990); human: Genebank Accession No. M24743; Hunt et al, Proc. Natl. Acad. Sci. U.S.A. 82:6455-6489 (1995)), and hsp40 (human: Genebank Accession No. D49547; Ohtsuka K., Biochem. Biophys. Res. Commun. 197:235-240 (1993)).

Methods of Administration

The hybrid antigens of the invention or complexes of hybrid antigens and heat shock proteins may be administered to a subject using either a peptide-based, protein-based or nucleic acid vaccine, so as to produce, in the subject, an amount of complex which is effective in inducing a therapeutic immune response in the subject.

The subject may be a human or nonhuman subject.

The term "therapeutic immune response," as used herein, refers to an increase in humoral and/or cellular immunity, as measured by standard techniques, which is directed toward the hybrid antigen. Preferably, but not by way of limitation, the induced level of humoral immunity directed toward hybrid antigen is at least four-fold, and preferably at least 16-fold greater than the levels of the humoral immunity directed toward the antigen prior to the administration of the compositions of this invention to the subject. The immune response may also be measured qualitatively, by means of a suitable in vitro or in vivo assay, wherein an arrest in progression or a remission of neoplastic or infectious disease in the subject is considered to indicate the induction of a therapeutic immune response.

Specific amounts of heat shock protein/hybrid antigen administered may depend on numerous factors including the immunogenicity of the particular vaccine composition, the immunocompetence of the subject, the size of the subject and the route of administration. Determining a suitable amount of any given composition for administration is a matter of routine screening.

Furthermore, significant immunological efficacy was identified in studies in which the hybrid antigen was administered alone, i.e., without heat shock protein. While Applicants have no duty to disclose the theory by which the invention operates, and are not bound thereto, the results of these studies suggest that the hybrid antigens, upon injection into the subject, bind to endogenous heat shock proteins, and thus do not require the concomitant administration of heat shock protein for effectiveness. The present invention extends to such utilities of the hybrid antigens of the invention, and moreover, to concomitant therapies or treatments that increase endogenous heat shock protein levels systemically or at the intended site of administration of the hybrid antigens of the invention. Such concomitant therapies or treatments include but are not limited to local application of heat or local or systemic pharmaceutical agents that increase the expression of heat shock protein in the local tissue. Such agents and methods are known in the art.

Hybrid antigens that are administered in the absence of co-administration of a heat shock protein (i.e., administered not in a complex with a heat shock protein) that comprise at least one antigenic domain and at least one heat shock protein binding domain comprise one of the peptide linkers mentioned hereinabove.

In specific non-limiting embodiments of the invention, it may be desirable to include more than one species of heat shock protein, and/or more than one hybrid antigen, in order to optimize the immune response. Such an approach may be particularly advantageous in the treatment of cancer or in the treatment of infections characterized by the rapid development of mutations that result in evasion of the immune response. Moreover, a hybrid antigen of the invention may include more than one immunogenic domain or more than one epitope.

Compositions comprising hybrid antigen/heat shock protein or hybrid antigen alone as set forth above are referred to herein as "vaccines." The term vaccine is used to indicate that the compositions of the invention may be used to induce a prophylactic or therapeutic immune response. A vaccine of the invention may comprise a hybrid antigen with a single antigenic domain or epitope, or a hybrid antigen with a plurality of antigenic domains or epitopes. Further, a vaccine may comprise an admixture of hybrid antigens with single or pluralities of antigenic domains or epitopes, or any combination of the foregoing. As noted above, the hybrid antigens or admixtures thereof may be complexed with one or more heat shock proteins before administration, or may be administered without heat shock protein.

A vaccine composition comprising one or more hybrid antigens optionally complexed to one or more heat shock proteins in accordance with the invention may be administered cutaneously, subcutaneously, intradermally, intravenously, intramuscularly, parenterally, intrapulmonarily, intravaginally, intrarectally, nasally or topically. The vaccine composition may be delivered by injection, particle bombardment, orally or by aerosol.

Incubation of heat shock proteins in solution with the hybrid antigen is sufficient to achieve loading of the antigen onto the heat shock protein in most cases. It may be desirable in some cases, however, to add agents which can assist in the loading of the antigen.

Incubation with heating of the heat shock protein with the hybrid antigen will in general lead to loading of the antigen onto the heat shock protein. In some cases, however, it may be desirable to add additional agents to assist in the loading. For example, hsp40can facilitate loading of peptides onto hsp70. Minami et al., *J. Biol. Chem.* 271:19617-19624 (1996). Denaturants such as guanidinium HCl or urea can be employed to partially and reversibly destabilize the heat shock protein to make the peptide binding pocket more accessible to the antigen.

In particular, a vaccine of the invention comprising a heat shock protein preferably also includes adenosine diphosphate (ADP), to promote the association between the heat shock protein and the heat shock protein binding domain prior to the complex reaching its destination. Other compounds with similar capabilities may used, alone or in combination with ADP.

Vaccine compositions in accordance with the invention may further include various additional materials, such as a pharmaceutically acceptable carrier. Suitable carriers include any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

The vaccine composition of the invention may also include suitable diluents, preservatives, solubilizers, emulsifiers, adjuvants and/or carriers. Such compositions may be in the form of liquid or lyophilized or otherwise dried formulations and may include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g. glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexing with metal ions, or incorporation of the material into or onto particulate preparations of polymeric compounds such as polylactic acid, polyglycolic acid, hydrogels, etc. or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. The choice of compositions will depend on the physical and chemical properties of the vaccine. For example, a product derived from a membrane-bound form of a protein may require a formulation containing detergent. Controlled or sustained release compositions include formulation in lipophilic depots (e.g. fatty acids, waxes, oils). Also comprehended by the invention are particulate compositions coated with polymers (e.g. poloxamers or poloxamines) and coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including intramuscular, parenteral, pulmonary, nasal and oral.

As an alternative to direct administration of the hybrid antigen optionally complexed with heat shock protein, one or more polynucleotide constructs may be administered which encode the hybrid antigen, optionally with heat shock protein, in expressible form. The expressible polynucleotide constructs are introduced into cells in the subject using ex vivo or in vivo methods. Suitable methods include injection directly into tissue and tumors, transfecting using liposomes (Fraley et al., *Nature* 370:111-117 (1980)), receptor-mediated endocytosis (Zatloukal et al., *Ann. NY Acad. Sci.* 660:136-153 (1992)), particle bombardment-mediated gene transfer (Eisenbraun et al., *DNA & Cell Biol.* 12:792-797 (1993)) and transfection using peptide presenting bacteriophage (Barry et al, *Nature Medicine* 2:299-305 (1996).

The polynucleotide vaccine may also be introduced into suitable cells in vitro which are then introduced into the subject.

To construct an expressible polynucleotide, a region encoding the heat shock protein and/or hybrid antigen is prepared as discussed above and inserted into a mammalian expression vector operatively linked to a suitable promoter such as the SV40 promoter, the cytomegalovirus (CMV) promoter or the Rous sarcoma virus (RSV) promoter. The resulting construct may then be used as a vaccine for genetic immunization. The nucleic acid polymer(s) could also be cloned into a viral vector. Suitable vectors include but are not limited to retroviral vectors, adenovirus vectors, vaccinia virus vectors, pox virus vectors and adenovirus-associated vectors. Specific vectors which are suitable for use in the present invention are pCDNA3 (InVitrogen), plasmid AH5 (which contains the SV40 origin and the adenovirus major late promoter), pRC/CMV (InVitrogen), pCMU II (Paabo et al., EMBO J. 5:1921-1927 (1986)), pZip-Neo SV (Cepko et al., Cell 37:1053-1062 (1984)) and pSRα (DNAX, Palo Alto, Calif.).

Various methods for preparation of heat shock proteins and hybrid antigens are disclosed in WO9706821 and WO9922761, which are incorporated herein by reference in their entireties.

In the following examples, and throughout the application amino acids may be represented using their single-letter codes, as follows:

A alanine
C cysteine
D aspartic acid
E glutamic acid
F phenylalanine
G glycine
H histidine
I isoleucine
K lysine
L leucine
M methionine
N asparagine
P proline
Q glutamine
R arginine
S serine
T threonine
V valine
W tryptophan
Y tyrosine The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

A variety of hybrid antigens were prepared, each comprising a heat shock protein binding domain and a cancer antigen epitope or the model Class I H2-$K^b$ epitope from ovalbumin, SIINFEKL (SEQ ID NO:868). A peptide linker was included between the two domains. The heat shock protein binding domains used in these experiments were among the following: HWDFAWPW (SEQ ID NO:869), NLLRLTGW (SEQ ID NO:870), FYQLALTW (SEQ ID NO:871) and RKLFFNLRW (SEQ ID NO:872). Linkers were among those described hereinabove.

The cancer and model epitopes were among the following:

| Source Protein | Source Tumor | Amino Acids | Trivial Name (Amino acid sequence) |
|---|---|---|---|
| Prostate Specific Membrane Antigen | Prostate cancer | 771–779 | PSMA P2 (ALFDIESKV; SEQ ID NO:873) |
| Gp100 | Melanoma | 209–217 | IMD (210M) (IMDQVPFSV; SEQ ID NO:874) |
| Tyrosinase | Melanoma | 368–376 | YMD (370D) (YMDGTMSQV; SEQ ID NO:875) |
| Human Papillomavirus (HPV) Strain 16 E7 | Cervical cancer | 86–93 | HPV16 E7 86–93 (TLGIVCPI; SEQ ID NO:876) |
| HPV Strain 16 E7 | Cervical cancer | 11–20 | HPV16 E711–20 (YMLDLQPETT; SEQ ID NO:877) |
| Ovalbumin | Model Tumor Antigen | 257–264 | Ova (SIINFEKL; SEQ ID NO:868) |

Using standard solid phase peptide synthesis using F-moc chemistry, hybrid antigens comprising a heat shock protein binding domain, a cancer epitope, and a linker there between, were synthesized, in various orientations.

EXAMPLE 2

Binding affinities between recombinant human or murine heat shock protein 70 (hsp70) and the various heat shock protein binding domains and antigenic peptides mentioned above, as well as between the hybrid antigens comprising an antigenic peptide and a heat shock protein binding domain described above, were determined by a binding inhibition assays (Hill plots) relative to the binding affinity of a reference, labeled hybrid antigen (tritiated or fluoresceinated ALFDIESKVGSGHWDFAWPW; SEQ ID NO:878) to hsp70 as determined by Scatchard analysis (Kds of 22.64 µM and 10.75 µM, respectively). Binding studies were performed in 39% PBS; 20 mM THAM, pH 8; 37 mM NaCl, 5 mM $MgCl_2$; and 1 mM ADP.

EXAMPLE 3

For immunological studies in mice, a murine MHC H2-K(b) epitope from ovalbumin, SIINFEKL (amino acids 257-264; SEQ ID NO:868), and a H2-K(b) peptide from the nucleoprotein of vesicular stomatitis virus (VSV), RGYVYQGL (amino acids 52-59; SEQ ID NO:879) were used for the preparation of hybrid antigens. The following table sets forth the sequences and the affinities for hsp70of the epitopes alone and in hybrid antigens.

EXAMPLE 4

Mice were immunized s.c. at the base of the tail with hsp70alone, hsp70 complexed with SIINFEKL (SEQ ID NO:868), and hybrid SLINFEKL (SEQ ID NO:868) peptide with or without HSP70. The doses were adjusted such that each immunization contained the same amount of SIINFEKL (SEQ ID NO:868), except for hsp70 alone. Seven days later, spleens were harvested and enriched for CD8+T cells, which were put into an ex vivo IFN-γ ELISPOT assay. Responses after pulsing with SIINFEKL (SEQ ID NO:868; "SIINFEKL") were recorded in the following table, which includes the doses, and the number of spots (mean±standard error) per $4 \times 10^5$ CD8 T cells, of≧four experiments with at least three mice per group. Controls included medium alone ("medium control"), unpulsed T cells ("unpulsed control"), T cells pulsed with a non-immunized peptide derived from VSV, RGYVYQGL (SEQ ID NO:879; "VSV control"), and exposure to concanavalin A as a positive control ("Con A positive control").

In the same experiment, a $^{51}$Cr-release assay as described above was done using SIINFEKL (SEQ ID NO:868)-pulsed target cells. At an effector to target cell ratio of 200:1, the percent killing results obtained are shown in the far right column of the following table.

(200-10)

| Mouse Epitope | Epitope alone | | Hybrid antigen comprising epitope | |
|---|---|---|---|---|
| | Epitope sequence | Affinity for hsp70 (µM) | Hybrid antigen sequence | Affinity for hsp70 (µM) |
| Ovalbumin: amino acids 257-264 | SIINFEKL (SEQ ID NO:868) | 235 | NLLRLTGWGSGSIINFEKL (SEQ ID NO:880) | 1.6 |
| | | | NLLRLTGWFFRKSIINFEKL (SEQ ID NO:881) | 2.2 |
| | | | NLLRLTGWRKSIINFEKL (SEQ ID NO:882) | 0.8 |
| VSV nucleoprotein: amino acids 52-59 | RGYVYQGL (SEQ ID NO:879) | 82 | NLLRLTGWGSGRGYVYQGL (SEQ ID NO:883) | 1.4 |
| | | | NLLRLTGWFFRKRGYVYQGL (SEQ ID NO:884) | 1.0 |
| | | | NLLRLTGWRKRGYVYQGL (SEQ ID NO:885) | 0.6 |

| Immunogen | Number of Spots per 400,000 cells | | | | | CTL assay: % killing at 200:1 E/T |
| --- | --- | --- | --- | --- | --- | --- |
| | SIINFEKL (SEQ ID NO:868) | Medium control | Unpulsed control | VSV control | Con A positive control | |
| 4.4 µg Hsp70 | 0.00 ± 0.00 | 1.50 ± 2.12 | 0.67 ± 0.58 | 0.33 ± 0.58 | 834 ± 28.3 | 0% |
| 4.4 µg Hsp70 + 0.9 µg SIINFEKL (SEQ ID NO:868) | 33.7 ± 7.09 | 0.00 ± 0.00 | 0.33 ± 0.58 | 0.00 ± 0.00 | 1000 ± 33.7 | 19% |
| 4.4 µg Hsp70 + 2.0 µg NLLRLTGWGSGSIINFEKL (SEQ ID NO:880) | 80.0 ± 17.0 | 0.00 ± 0.00 | 1.50 ± 0.71 | 1.50 ± 0.71 | 1170 ± 56.5 | 38% |
| 4.4 µg Hsp70 + 2.4 µg NLLRLTGWFFRKSIINFEKL (SEQ ID NO:881) | 222 ± 17.7 | 0.00 ± 0.00 | 0.67 ± 0.58 | 1.33 ± 1.53 | 1010 ± 56.5 | 52% |

EXAMPLE 5

An experiment similar to that described above was carried out, which also included hybrid antigen without hsp70.

(200-11)

| Immunogen | Number of Spots per $4 \times 10^5$ CD8 T cells | | | | |
| --- | --- | --- | --- | --- | --- |
| | SIINFEKL (SEQ ID NO:868) | Medium control | Unpulsed control | VSV control | Con A Positive control |
| 4.4 µg Hsp70 | 0.33 ± 0.58 | 1.00 ± 1.73 | 1.67 ± 1.15 | 4.00 ± 1.00 | 965 ± 62.6 |
| 4.4 µg Hsp70 + 0.9 µg SIINFEKL (SEQ ID NO:868) | 1.67 ± 0.58 | 1.00 ± 1.00 | 2.00 ± 0.00 | 2.67 ± 2.08 | 591 ± 48.1 |
| 4.4 µg Hsp70 + 2.0 µg NLLRLTGWGSGSIINFEKL (SEQ ID NO:880) | 12.0 ± 5.2 | 2.67 ± 0.58 | 1.67 ± 1.15 | 2.00 ± 2.65 | 748 ± 58.6 |
| 4.4 µg Hsp70 +2.4 µg NLLRLTGWFFRKSIINFEKL (SEQ ID NO:881) | 770 ± 80.6 | 3.33 ± 1.53 | 3.67 ± 1.53 | 4.33 ± 1.53 | 742 ± 72.6 |
| 2.4 µg NLLRLTGWFFRKSIINFEKL (SEQ ID NO:881) (no hsp70) | 151 ± 20.7 | 1.00 ± 1.00 | 1.67 ± 0.58 | 0.00 ± 0.00 | 459 ± 149 |

EXAMPLE 6

A further experiment was carried out similar to that described above.

(200-12)

| Immunogen | Number of Spots per 300,000 CD8 T cells | | | | | CTL assay: % killing at 200:1 E/T |
| --- | --- | --- | --- | --- | --- | --- |
| | SIINFEKL (SEQ ID NO:868) | Medium control | Unpulsed control | VSV control | Con A positive control | |
| 4.4 µg Hsp70 | 0.67 ± 0.58 | 0.00 ± 0.00 | 0.50 ± 0.71 | 1.00 ± 1.41 | 552 ± 24.0 | 8.45 ± 41.3 |
| 4.4 µg Hsp70 + 0.9 µg SIINFEKL (SEQ ID NO:868) | 3.33 ± 2.52 | 0.00 ± 0.00 | 0.33 ± 0.58 | 0.33 ± 0.58 | 450 ± 69.0 | 43.0 ± 21.2 |

-continued

|  | Number of Spots per 300,000 CD8 T cells | | | | | |
|---|---|---|---|---|---|---|
| Immunogen | SIINFEKL (SEQ ID NO:868) | Medium control | Unpulsed control | VSV control | Con A positive control | CTL assay: % killing at 200:1 E/T |
| 4.4 µg Hsp70 + 2.00 µg NLLRLTGWGSG-SIINFEKL (SEQ ID NO:880) | 134 ± 4.16 | 1.33 ± 1.53 | 0.67 ± 1.15 | 1.00 ± 1.00 | 865 ± 93.0 | 31.9 ± 5.41 |
| 4.4 µg Hsp70 + 2.4 µg NLLRLTGWFFRK-SIINFEKL (SEQ ID NO:881) | 680 ± 23.0 | 0.00 ± 0.00 | 0.00 ± 0.00 | 1.67 ± 0.58 | 801 ± 56.6 | 84.6 ± 1.70 |
| 2.4 µg NLLRLTGWFFRK-SIINFEKL (SEQ ID NO:881) | 211 ± 17.0 | 0.00 ± 0.00 | 0.50 ± 0.71 | 1.00 ± 0.00 | 688 ± 41.7 | 9.91 ± 5.57 |

EXAMPLE 7

As in the prior in vivo experiments, B6 mice were immunized s.c. to evaluate complexes of hsp70 with hybrid antigens made using other short peptide linkers, including (using one-letter amino-acid codes) FFRK (SEQ ID NO:699), RK, AKVL (SEQ ID NO:700), QLK and FR, and at different doses. An ex vivo IFN-γ ELISPOT assay was performed as described above. The results including the control values are as follows.

(200-13)

|  | Number of Spots per 300,000 cells | | | |
|---|---|---|---|---|
| Immunogen | SIINFEKL | Medium control | Unpulsed control | VSV control |
| 4.4 µg Hsp70 + 2.4 µg NLLRLTGWFFRKSIINFEKL (SEQ ID NO:881) | 114 ± 21 | 1.0 ± 1.2 | 1.0 ± 0 | 0.67 ± 0.41 |
| 4.4 µg Hsp70 + 2.4 µg NLLRLTGWRKSIINFEKL (SEQ ID NO:882) | 70 ± 8.5 | 1.3 ± 1.1 | 0.67 ± 0.82 | 2.7 ± 1.1 |
| 0.9 µg Hsp70 + 0.48 µg NLLRLTGWFFRKSIINFEKL (SEQ ID NO:881) | 98 ± 0.41 | .67 ± 0.82 | 1.3 ± 1.1 | 4.3 ± 2.3 |
| 0.9 µg Hsp70 + 0.48 µg NLLRLTGWRKSIINFEKL (SEQ ID NO:882) | 29 ± 2.2 | 0 ± 0 | 1 ± 0 | 0 ± 0 |
| 2.4 µg NLLRLTGWFFRKSIINFEKL (SEQ ID NO:881) | 11 ± 1.8 | 0.67 ± 0.82 | 0 ± 0 | 0.67 ± 0.82 |

200-21

|  | Number of Spots per 400,000 cells | | | |
|---|---|---|---|---|
| Immunogen | SIINFEKL (SEQ ID NO:868) | Medium control | Unpulsed control | VSV control |
| 4.4 µg Hsp70 + 2.4 µg NLLRLTGWFFRKSIINFEKL (SEQ ID NO:881) | 124 ± 8.8 | 0.33 ± 0.41 | 0.67 ± 0.82 | 2.67 ± 2.68 |

-continued

| Immunogen | Number of Spots per 400,000 cells | | | |
|---|---|---|---|---|
| | SIINFEKL (SEQ ID NO:868) | Medium control | Unpulsed control | VSV control |
| 4.4 μg Hsp70 + 2.4 μg NLLRLTGWAKVLSIINFEKL (SEQ ID NO:886) | 95 ± 12 | 1.33 ± 0.82 | 1.0 ± 1.2 | 0.67 ± 0.41 |

200-23

| Immunogen | Number of Spots per 400,000 cells | | | |
|---|---|---|---|---|
| | SIINFEKL (SEQ ID NO:868) | Medium control | Unpulsed control | VSV control |
| 4.4 μg Hsp70 + 2.4 μg NLLRLTGWFFRKSIINFEKL (SEQ ID NO:881) | 318 ± 17 | 0.67 ± 0.51 | 0.67 ± 0.58 | 0.67 ± 0.58 |
| 4.4 μg Hsp70 + 2.4 μg NLLRLTGWQLKSIINFEKL (SEQ ID NO:887) | 174 ± 18 | 0.0 ± 0.0 | 0.0 ± 0.0 | 3.7 ± 2.5 |
| 4.4 μg Hsp70 + 2.4 μg NLLRLTGWFRSIINFEKL (SEQ ID NO:888) | 53 ± 2.9 | 0.0 ± 0.0 | 0.67 ± 0.58 | 1.0 ± 1.0 |
| 2.4 μg NLLRLTGWFRSIINFEKL (SEQ ID NO:888) | 31 ± 5.7 | 1.0 ± 1.7 | 0.0 ± 0.0 | 0.67 ± 0.58 |

EXAMPLE 8

Similar in vivo studies in B6 mice as those described above were performed using formulations without added hsp70. The results are as follows.

(200-17)

| Immunogen | Number of Spots per 400,000 cells | | | | |
|---|---|---|---|---|---|
| | SIINFEKL (SEQ ID NO:868) | Medium control | Unpulsed control | VSV control | Con A positive control |
| 10 μg SIINFEKL (SEQ ID NO:868) | 2.33 ± 0.41 | 0.33 ± 0.41 | 1.33 ± 0.82 | 1.7 ± 0.41 | 928 ± 72 |
| 0.5 μg NLLRLTGWFFRKSIINFEKL (SEQ ID NO:881) | 22 ± 7.2 | 1.33 ± 0.41 | 1.67 ± 1.1 | 1.0 ± 0.71 | 906 ± 17 |
| 2.5 μg NLLRLTGWFFRKSIINFEKL (SEQ ID NO:881) | 28 ± 2.7 | 1.0 ± 1.7 | 0.33 ± 0.41 | 2.0 ± 1.2 | 930 ± 23 |
| 25 μg NLLRLTGWFFRKSIINFEKL (SEQ ID NO:881) | 46 ± 4.3 | 2.0 ± 0.41 | 1.33 ± 1.1 | 3.0 ± 0.71 | 1007 ± 17 |

EXAMPLE 9

Similar in vivo studies in B6 mice as those described above were performed using formulations with or without hsp70. In addition, one study was carried out in which hybrid antigen was co-administered with free heat shock protein-binding domain peptide (NLLRLTGW) (SEQ ID NO:870). The results are as follows.

(VSV-72-02)

|  | Number of spots per 400,000 cells | | | | | CTL % killing |
|---|---|---|---|---|---|---|
| Immunogen | SIINFEKL (SEQ ID NO:868) | Medium control | Unpulsed control | VSV control | Con A positive control | at 200:1 E/T |
| 4 µg Hsp70 + 2.0 µg NLLRLTGWFFRKSIINFEKL (SEQ ID NO:881) | 48 ± 11 | 0.0 ± 1.0 | 0.0 ± 1.0 | 4.0 ± 2.0 | 588 ± 151 | 32% |
| 2.0 µg NLLRLTGWRKSIINFEKL (SEQ ID NO:882) | 24 ± 1 | 1.0 ± 1.0 | 1.0 ± 1.0 | 5.0 ± 3.0 | 842 ± 73 | 24% |
| 2.0 µg NLLRLTGWFFRKSIINFEKL (SEQ ID NO:881) + 50-fold excess NLLRLTGW (SEQ ID NO:867) | 2.0 ± 1.0 | 1.0 ± 1.0 | 0.0 ± 1.0 | 1.0 ± 1.0 | 422 ± 54 | 18% |
| SIINFEKL (SEQ ID NO:868) | 1.0 ± 1.0 | 0.0 ± 0.0 | 0.0 ± 1.0 | 1.0 ± 1.0 | 478 ± 67 | 6% |

EXAMPLE 10

The VSV epitope used as a control in many of the foregoing experiments, RGYVYQGL (SEQ ID NO:879), was used as the epitope in preparing further hybrid antigens of the invention, and evaluated for induction of an immune response in similar experiments as described above.

(VSV-72-02)

|  | Number of Spots per 400,000 cells | | | |
|---|---|---|---|---|
| Immunogen | SIINFEKL (SEQ ID NO:868) | Medium control | Unpulsed control | VSV (RGYVYQGL) (SEQ ID NO:867) |
| 4 µg HSP plus 2 µg NLLRLTGWFFRKSIINFEKL (SEQ ID NO:881) | 48 ± 11 | 1.0 ± 1.0 | 0.0 ± 1.0 | 4.0 ± 2.0 |
| 4 µg HSP plus 2 µg NLLRLTGWFFRKRGYVYQGL (SEQ ID NO:884) | 1.0 ± 1.0 | 1.0 ± 1.0 | 4.0 ± 2.0 | 20 ± 1.0 |
| 4 µg HSP plus 6 µg NLLRLTGWFFRKRGYVYQGL (SEQ ID NO:884) | 6.0 ± 3.0 | 2.0 ± 2.0 | 12 ± 3.0 | 104 ± 13 |

EXAMPLE 11

In order to evaluate the efficacy of the aforementioned hybrid antigens and complexes with hsp70 on the treatment of disease, a model was utilized in which 20,000 E7 tumor cells modified to express ovalbumin (designated E.G7) were subcutaneously implanted in B6 mice. Ten mice were used per treatment group. This model is described, for example, in Moroi et al., 2000, *Proc. Nat. Acad. Sci. USA* 97:3485-3490. The results in number of mice with tumors over time are shown in FIG. 1. After 31 days, none of 10 mice immunized with hsp70:NLLRLTG FFRKSIINFEKL (SEQ ID NO:881) developed tumors, nor did mice immunized with SIINFEKL (SEQ ID NO:868) emulsified in Titermax adjuvant. Three of 10 mice vaccinated with NLLRLTGW-FFRKSIINFEKL (SEQ ID NO:881) alone (no hsp70) had tumors. Five of 10 mice vaccinated with hsp70: SIINFEKL (SEQ ID NO:868) had tumors, and 9 of 10 mice immunized with Titermax and buffer alone had tumors.

EXAMPLE 12

The in-vitro antigen presentation assay described above was utilized further in order to evaluate the formulations of the invention. To demonstrate the requirement of the hybrid antigens of the invention for hsp70, whether supplied in the formulation or endogenously available, for entry of the hybrid antigen and more specifically its antigen into the antigen presentation pathway, the assay was performed with the following formulations, with the results indicated.

(200-MF-41)

| Formulation | Pg/ml IL-2 produced by B3Z cells |
|---|---|
| 0.5 ng SIINFEKL (SEQ ID NO:868) | 2690 ± 369 |
| 5 ng NLLRLTGWFFRKSIINFEKL (SEQ ID NO:881) | 46 ± 11 |
| 5 ng NLLRLTGWFFRKSIINFEKL (SEQ ID NO:881) plus 1.4 ug hsp70 | 3920 ± 344 |
| 1.4 ug Hsp70 | 0.0 ± 0.0 |

EXAMPLE 13

The HHD II mouse model bearing a human HLA-A2 complex described by Firat et al., 1999, "H-2 class I knockout, HLA-A2. 1-transgenic mice: a versatile animal model for preclinical evaluation of antitumor immunotherapeutic strategies," *Eur J Immunol*. 29:3112-21, was used in the following experiments to evaluate human HLA-A2 epitopes in hybrid antigens of the invention. The "IMED" peptide epitope IMDQVPFSV (SEQ ID NO:874) from the human melanoma antigen gp100 was evaluated in a hybrid antigen of the invention at low and high dose in the HHD II model. Similar methods to those described above were used for the ELISPOT assay, with test peptides being the IMD peptide and, as a control, a peptide from the melanoma antigen tyrosinase, YMDGTMSQV (SEQ ID NO:875) ("YMD"). The results are shown on the following table.

(HHD II 200-72-02)

| | Number of Spots per 400,000 cells | | | |
|---|---|---|---|---|
| Immunogen | IMD | Medium control | Unpulsed control | YMD control |
| 4 µg hsp70 and 5 µg NLLRLTGWFFRKIMDQVPFSV (SEQ ID NO:889) | 139 ± 11 | 0.67 ± 0.58 | 1.0 ± 1.0 | 3.7 ± 0.58 |
| 4 µg hsp70 and 10 µg NLLRLTGWFFRKIMDQVPFSV (SEQ ID NO:889) | 217 ± 3.2 | 0.67 ± 0.58 | 4.0 ± 6.0 | 2.7 ± 1.5 |
| 2 µg NLLRLTGWFFRKIMDQVPFSV (SEQ ID NO:889) | 27 ± 5.1 | 0.0 ± 0.0 | 0.0 ± 0.0 | 2.0 ± 2.0 |

A similar experiment in HHD II mice carried out using YMD as the epitope in the hybrid antigen, in a complex with hsp70, as follows.

(200-72-01)

| | Number of Spots per 400,000 cells | | | |
|---|---|---|---|---|
| Immunogen | YMD | Medium control | Unpulsed control | IMD control |
| 4 µg hsp70 and 5 µg NLLRLTGWFFRKYMDGTMSQV (SEQ ID NO:890) | 33 ± 7.8 | 1.0 ± 0.0 | 1.0 ± 0.0 | 1.0 ± 1.4 |

-continued

| Immunogen | Number of Spots per 400,000 cells | | | |
|---|---|---|---|---|
| | YMD | Medium control | Unpulsed control | IMD control |
| 4 µg hsp70 and 10 µg NLLRLTGWFFRKYMDGTMSQV (SEQ ID NO:890) | 323 ± 44 | 0.0 ± 0.0 | 1.5 ± 0.71 | 1.5 ± 0.71 |

EXAMPLE 14

An epitope from Sendai virus (SdV), FAPGNYPAL (SEQ ID NO:891), was evaluated in hybrid antigens of the invention in B6 mice, similar to the above. The results are as follows.

(200-18)

| Immunogen | Number of Spots per 400,000 cells | | |
|---|---|---|---|
| | SdV | Medium control | SIINFEKL (SEQ ID NO:868) control |
| 4 µg hsp70 and 2 µg NLLRLTGWFFRKSIINFEKL (SEQ ID NO:881) | 1.3 ± 1.2 | 1.0 ± 1.0 | 197 ± 27 |
| 2 µg NLLRLTGWFFRKRGYVYQGL (SEQ ID NO:884) | 0.33 ± 0.58 | 0.0 ± 0.0 | 87 ± 20 |
| 4 µg hsp70 and 2 µg NLLRLTGWFFRKFAPGNYPAL (SEQ ID NO:892) | 38 ± 17 | 0.33 ± 0.58 | 1.0 ± 1.0 |
| 13 µg hsp70 and 7 µg NLLRLTGWFFRKFAPGNYPAL (SEQ ID NO:892) | 169 ± 32 | 4.3 ± 1.5 | 7.0 ± 3.5 |

EXAMPLE 15

In-vivo experiments on co-administration of two hybrid antigens of the invention with hsp70 to B6 mice was performed. Hybrid antigens containing SIINFEKL (SEQ ID NO:868) from ovalbumin and RGYVYQGL (SEQ ID NO:879) from VSV were admixed and immunized with hsp70. The results are as follow.

(OVA-VSV-72-01)

| Immunogen | Number of Spots per 400,000 cells | | | |
|---|---|---|---|---|
| | VSV | Medium control | Unpulsed control | OVA |
| 2 µg hsp70 2 µg NLLRLTGWFFRKSIINFEKL (SEQ ID NO:881) 2 µg NLLRLTGWFFRKRGYVYQGL (SEQ ID NO:884) | 77 ± 19 | 2.0 ± 1.0 | 2.0 ± 1.0 | 366 ± 19 |
| 2 µg hsp70 6 µg NLLRLTGWFFRKSIINFEKL (SEQ ID NO:881) 6 µg NLLRLTGWFFRKRGYVYQGL (SEQ ID NO:884) | 185 ± 9 | 1.0 ± 1.0 | 4.0 ± 2.0 | 349 ± 10 |

EXAMPLE 16

As noted above, in one aspect of the invention, formulations containing a plurality of hybrid antigens comprising different antigenic epitopes may be formulated with one or more heat shock proteins for immunization in humans in order to elicit an effective immune response to treat or prevent a disease. For example, for treating human melanoma, a formulation comprising 8 different melanoma epitopes may be prepared as hybrid antigens, and formulated, for example, with hsp70. In this particular formulation, the heat shock protein binding domain NLLRLTGW (SEQ ID NO:870) at the N-terminus is used for all epitopes, linked to the epitope at the C-terminus using the peptide linker FFRK (SEQ ID NO:699). Other binding domains and linkers are embraced herein. This particular formulation is useful for treating patients with the HLA-A2 haplotype. A formulation comprises the following hybrid antigens with hsp70:

| Source and amino acid sequence of antigen | Hybrid antigen sequence |
|---|---|
| gp 100: amino acids 209–217 (modified 210M) | NLLRLTGWFFRKIMDQVPFSV (SEQ ID NO:889) |
| tyrosinase: amino acids 368–376 (modified 370D) | NLLRLTGWFFRKYMDGTMSQV (SEQ ID NO:890) |
| Melan-A: amino acids 26–35 (modified 27L) | NLLRLTGWFFRKELAGIGILTV (SEQ ID NO: 893) |
| NY-ESO-1: amino acids 157–165 (modified 165V) | NLLRLTGWFFRKSLLMWITQV (SEQ ID NO:894) |
| TRP-2: amino acids 180–188 | NLLRLTGWFFRKSVYDFFVWL (SEQ ID NO:895) |
| MAGE-10: amino acids 254–262 | GLYDGMEHLGSGNLLRLTGW (SEQ ID NO:896) |
| gp100: amino acids 280–288 (288V) | YLEPGPVTVGSGNLLRLTGW (SEQ ID NO:897) |
| SSX-2: amino acids 41–49 | KASEKIFYVGSGNLLRLTGW (SEQ ID NO: 898) |

In one embodiment, approximately equal amounts of the foregoing 8 hybrid antigens may be complexed with hsp70, and administered in saline. In another embodiment, a formulation comprises the first five hybrid antigens listed. The aforementioned formulations containing heat shock protein in saline optionally may contain ADP to stabilize the complexes, as well as other components, such as excipients, diluents and carriers, as mentioned above. In another embodiment, an admixture of the foregoing 8 hybrid antigens, or the first 5 listed, is formulated in saline for administration without a heat shock protein.

EXAMPLE 17

Prime-boost protocols were valuated in this experiment. Using the NLLRLTGWFFRKSIINFEKL (SEQ ID NO:881) hybrid antigen, or without co-administered hsp70, the following 5 protocols were followed: 1) administer at day 0, analyze at day 7; 2) administer at days 0 and 7, analyze at day 21; 3) administer at day 0, analyze at day 21; 4) administer at days 0 and 14, analyze at day 28; and 5) administer at day 0 and analyze at day 28. The results in number of spots per 400,000 cells, were as follows.

(200-28-72-01a, -01b, -01c)

| Protocol day(s) immunized | 0 | 0, 7 | 0 | 0, 14 | 0 |
|---|---|---|---|---|---|
| Protocol day analyzed | 7 | 21 | 21 | 28 | 28 |
| SIINFEKL (SEQ ID NO:868) | 3.0 ± 2.0 | 2.0 ± 1.0 | 0.0 ± 1.0 | 1.0 ± 1.0 | 1.0 ± 1.0 |
| 2 μg hsp70, 4 μg SIINFEKL (SEQ ID NO:868) | 3.0 ± 1.0 | 6.0 ± 1.0 | 22 ± 8.0 | 3.0 ± 2.0 | 20 ± 5.0 |
| 2 μg NLLRLTGWFFRKSIINFEKL (SEQ ID NO:881) | 72 ± 5.0 | 24 ± 6.0 | 42 ± 7.0 | 25 ± 9.0 | 82 ± 11 |
| 2 μg hsp70 and 4 μg NLLRLTGWFFRKSIINFEKL (SEQ ID NO:881) | 99 ± 12 | 98 ± 11 | 141 ± 14 | 398 ± 18 | 27 ± 2.0 |
| 2 μg hsp70 | 5.0 ± 6.0 | 3.0 ± 2.0 | 3.0 ± 0.0 | 1.0 ± 1.0 | 4.0 ± 3.0 |

EXAMPLE 18

Further experiments were performed with mixtures of hybrid antigens to demonstrate eliciting of an immune response to the component antigens, as above. In this experiment, hybrid antigens containing SIINFEKL (SEQ ID NO:868) and the VSV peptide RGYVYQGL (SEQ ID NO:879) were used.

(VSV/OVA-72-02)

| Immunogen | Number of Spots per 300,000 cells | | | |
|---|---|---|---|---|
| | SIINFEKL | Medium control | Unpulsed control | VSV (RGYVYQGL) (SEQ ID NO:879) |
| 3.7 µg hsp70<br>2 µg<br>NLLRLTGWFFRKSIINFEKL<br>(SEQ ID NO:881) | 238 ± 27 | 0.0 ± 0.0 | 1.0 ± 1.0 | 5.0 ± 2.0 |
| 11.2 µg hsp70<br>6 µg<br>NLLRLTGWFFRKSIINFEKL<br>(SEQ ID NO:881) | 330 ± 45 | 1.0 ± 1.0 | 0.0 ± 0.0 | 4.0 ± 1.0 |
| 3.7 µg hsp70<br>2 µg<br>NLLRLTGWFFRKRGYVYQGL<br>(SEQ ID NO:884) | 1.0 ± 1.0 | 1.0 ± 1.0 | 0.0 ± 0.0 | 61 ± 11 |
| 11.2 µg hsp70<br>6 µg<br>NLLRLTGWFFRKRGYVYQGL<br>(SEQ ID NO:884) | 2.0 ± 2.0 | 2.0 ± 1.0 | 2.0 ± 0.0 | 147 ± 20 |
| 3.7 µg hsp70<br>2 µg<br>NLLRLTGWFFRKSIINFEKL<br>(SEQ ID NO:881)<br>2 µg<br>NLLRLTGWFFRKRGYVYQGL<br>(SEQ ID NO:884) | 179 ± 4.0 | 2.0 ± 2.0 | 1.0 ± 1.0 | 165 ± 11 |
| 11.2 µg hsp70<br>6 µg<br>NLLRLTGWFFRKSIINFEKL<br>(SEQ ID NO:881)<br>6 µg<br>NLLRLTGWFFRKRGYVYQGL<br>(SEQ ID NO:884) | 310 ± 13 | 1.0 ± 1.0 | 1.0 ± 1.0 | 242 ± 52 |

EXAMPLE 19

The binding affinity for hybrid antigens comprising heat shock protein binding domain NLLRLTGW (SEQ ID NO:870), antigenic domain SIINFEKL (SEQ ID NO:868) (from ovalbumin) or RGYVYQGL (SEQ ID NO:879) (from VSV protein) and various linkers set forth in Example 32 were carried out as described in Example 17. The antigenic domains alone had a Kd for hsp70binding of 235 µM and 82 µM, respectively. The results are shown below.

| Hybrid antigen | Kd for binding to HSP70 |
|---|---|
| NLLRLTGWGSGSIINFEKL (SEQ ID NO:880) | 1.6 µM |
| NLLRLTGWFFRKSIINFEKL (SEQ ID NO:881) | 2.2 µM |
| NLLRLTGWRKSIINFEKL (SEQ ID NO:882) | 0.8 µM |
| NLLRLTGWAKVLSIINFEKL (SEQ ID NO:886) | 2.0 µM |
| NLLRLTGWQLKSIINFEKL (SEQ ID NO:887) | 0.4 µM |
| NLLRLTGWFRSIINFEKL (SEQ ID NO:888) | 1.5 µM |
| NLLRLTGWGSGRGYVYQGL (SEQ ID NO:883) | 1.4 µM |

-continued

| Hybrid antigen | Kd for binding to HSP70 |
|---|---|
| NLLRLTGWFFRKRGYVYQGL (SEQ ID NO:884) | 1.0 µM |
| NLLRLTGWRKRGYVYQGL (SEQ ID NO:885) | 0.6 µM |

EXAMPLE 20

Further studies were carried out to evaluate the immunogenicity of hybrid antigens when administered alone to B6 mice, without co-administration of hsp70. The methods for evaluation using IFN-γ ELISPOT are as described above.

(Control 200-24 and 200-30)

| | Number of Spots per 300,000 cells | | | |
|---|---|---|---|---|
| Immunogen | SIINFEKL (SEQ ID NO:868) | SWDFITV (SEQ ID NO:814) | Medium | Unpulsed Splenocytes |
| 25 µg NLLRLTGWFFRKSIINFEKL (SEQ ID NO:881) | 109 ± 14 | NT | 0 ± 0 | 3.0 ± 2.0 |
| 24.9 µg NLLRLTGWFFRKSSWDFITV (SEQ ID NO:899) | NT | 26 ± 5 | 0.67 ± 0.58 | 0.33 ± 0.58 |
| 2.1 µg NLLRLTGWFRSIINFEKL (SEQ ID NO:888) | 12 ± 2 | NT | 0.67 ± 0.58 | 0.67 ± 0.58 |

NT not tested

EXAMPLE 21

Hybrid antigens were prepared comprising two antigens, separated by a linker as described above, such that the hybrid antigen has the following general structure:

(Heat shock protein binding domain)—(linker)—(Antigen 1)—(linker)—(Antigen 2).

While in this example the heat shock protein binding domain is at the N-terminal portion of the hybrid antigen, this is not necessarily the case and hybrid antigens with the heat shock protein binding domain at the C-terminus, or in-between the two antigenic domains, is embraced by the present invention. Furthermore, although in the examples below the same linker peptide is used between the antigenic domains and between the antigenic domain proximal to the heat shock protein binding domain, this is not necessarily the case and different linker peptides may be used. Moreover, the presence of the linker in one or both positions is optional. And furthermore, three or more antigenic peptides may be used. For simplicity, such hybrid antigens with two or more antigenic domains is termed a tandem hybrid antigen. Such tandem hybrid antigen compositions, complexes of one or more tandem hybrid antigens and a heat shock protein, and methods of eliciting an immune response or preventing or treating a disease by administering one or more tandem hybrid antigens or complexes of at least one heat shock protein and at least one tandem hybrid antigen are fully embraced herein.

The following experiments compare the immunogenicity of the admixture of two hybrid antigens and a tandem hybrid antigen comprising the same antigens, and a dose response study. In one experiment, a peptide comprising two linkers and epitopes but no heat shock protein binding domain was included.

(Control-200-72-01)

|  | Number of Spots per 300,000 cells | | | |
| --- | --- | --- | --- | --- |
| Immunogen | SIINFEKL (SEQ ID NO:868) | Medium control | Unpulsed control | RGYVYQGL (SEQ ID NO:879) |
| 19.2 µg NLLRLTGWFFRKSIINFEKLFFRKRGYVYGL (SEQ ID NO:900) | 390 ± 56 | 1.7 ± 1.1 | 3.0 ± 1.9 | 146 ± 13 |
| 19.2 µg NLLRLTGWFFRKRGYVYQGLFFRKSIINFEKL (SEQ ID NO:901) | 180 ± 11 | 1.3 ± 1.1 | 2.7 ± 1.1 | 321 ± 5.8 |

(S200-72-02)

|  | Number of Spots per 300,000 cells | | |
| --- | --- | --- | --- |
| Immunogen | SIINFEKL (SEQ ID NO:868) | Medium control | RGYVYQGL (SEQ ID NO:879) |
| 7.3 µg FFRKSIINFEKLFFRKRGYVYQGL (SEQ ID NO:883) | 8.3 ± 1.1 | 1.7 ± 0.4 | 31 ± 5.5 |
| 9.6 µg NLLRLTGWFFRKSIINFEKLFFRKRGYVYQG (SEQ ID NO:902)L | 713 ± 13 | 9.0 ± 1.2 | 207 ± 8.2 |
| 9.6 µg NLLRLTGWFFRKRGYVYQGLFFRKSIINFEKL (SEQ ID NO:903) | 69 ± 12 | 0.7 ± 0.4 | 460 ± 14 |

(S200-72-12)

|  | Number of Spots per 300,000 cells | | |
| --- | --- | --- | --- |
| Immunogen | SIINFEKL (SEQ ID NO:868) | Medium control | RGYVYQGL (SEQ ID NO:879) |
| 20 µg NLLRLTGWFFRKSIINFEKLFFRKRGYVYQGL (SEQ ID NO:900) | 410 ± 49 | 0.3 ± 0.4 | 250 ± 11 |
| 10 µg NLLRLTGWFFRKSIINFEKLFFRKRGYVYQGL (SEQ ID NO:900) | 360 ± 13 | 0.3 ± 0.4 | 100 ± 10 |
| 5 µg NLLRLTGWFFRKSIINFEKLFFRKRGYVYQGL (SEQ ID NO:900) | 130 ± 3.3 | 0 ± 0 | 35 ± 6.6 |
| 20 µg NLLRLTGWFFRKRGYVYQGLFFRKSIINFEKL (SEQ ID NO:901) | 150 ± 6 | 0 ± 0 | 380 ± 12 |
| 10 µg NLLRLTGWFFRKRGYVYQGLFFRKSIINFEKL (SEQ ID NO:901) | 30 ± 3 | 0 ± 0 | 83 ± 5 |

In this and other experiments, the epitope proximal to the heat shock protein binding domain exhibited the strongest immune response, and thus the positioning of the selected epitopes selected for the vaccine formulations of the invention may be positioned to contribute maximally to the overall immunogenicity of the formulation, whether administered in the absence of heat shock proteins or administered as complexes with heat shock proteins.

EXAMPLE 22

In the following experiments, admixtures of tandem hybrid antigens were evaluated for immunogenicity. In addition to the H2-K$^b$ Class I peptides from ovalbumin (SIINFEKL) (SEQ ID NO:868) and from VSV (RGYVYQGL) (SEQ ID NO:879), the H2-K$^b$ β-casein peptide IAYFYPEL (SEQ ID NO:904) and the Sendai virus peptide FAPGNYPAL (SEQ ID NO:891) were also used. In another experiment, two tandem hybrid antigens with the same antigenic peptides in alternate configurations were admixed. Strong immune responses to four epitopes were elicited.

All of the formulations herein included 1 mM ADP. In one experiment described below, ADP was omitted.

(200-72-04)

| Immunogen | Number of Spots per 300,000 cells ||||
|---|---|---|---|---|
| | SIINFEKL (SEQ ID NO:868) | RGYVYQGL (SEQ ID NO:879) | IAYFYPEL (SEQ ID NO:904) | FAPGNYPAL (SEQ ID NO:891) |
| 9.6 µg NLLRLTGWFFRKSIINFEKLFFRKRGYVYQGL (SEQ ID NO:900) | 537 ± 16 | 150 ± 10 | 4.7 ± 0.8 | 5.7 ± 2.5 |
| 9.7 µg NLLRLTGWFFRKIAYFYPELFFRKFAPGNYPAL (SEQ ID NO:905) | 1.7 ± 1.1 | 1.7 ± 0.8 | 128 ± 9.2 | 136 ± 6.6 |
| 9.6 µg NLLRLTGWFFRKSIINFEKLFFRKRGYVYQGL (SEQ ID NO:900) plus 9.7 µg NLLRLTGWFFRKIAYFYPELFFRKFAPGNYPAL (SEQ ID NO:950) | 363 ± 31 | 256 ± 5.3 | 127 ± 7.9 | 155 ± 28 |

S200-72-13

| Immunogen | Number of Spots per 300,000 cells ||||
|---|---|---|---|---|
| | SIINFEKL (SEQ ID NO:868) | RGYVYQGL (SEQ ID NO:879) | IAYFYPEL (SEQ ID NO:904) | FAPGNYPAL (SEQ ID NO:891) |
| 9.6 µg NLLRLTGWFFRKIAYFYPELFFRKFAPGNYPAL (SEQ ID NO:905) plus 9.6 µg NLLRLTGWFFRKSIINFEKLFFRKRGYVYQGL (SEQ ID NO:900) | 388 ± 6.8 | 72 ± 5.0 | 402 ± 17 | 379 ± 30 |
| 9.6 µg NLLRLTGWFFRKRGYVYQGLFFRKSIINFEKL (SEQ ID NO:903) Plus 9.6 µg NLLRLTGWFFRKIAYFYPELFFRKFAPGNYPAL (SEQ ID NO:905) | 76 ± 1.9 | 159 ± 8.3 | 115 ± 20 | 172 ± 5.9 |

S200-72-13

| Immunogen | Number of Spots per 300,000 cells | | | |
|---|---|---|---|---|
| | SIINFEKL (SEQ ID NO:868) | RGYVYQGL (SEQ ID NO:879) | IAYFYPEL (SEQ ID NO:904) | Medium |
| 9.6 µg NLLRLTGWFFRKSIINFEKLFFRKRGYVYQGL (SEQ ID NO:900) | 450 ± 10 | 273 ± 12 | 3.0 ± 1.4 | 0.33 ± 0.41 |
| 9.6 µg NLLRLTGWFFRKRGYVYQGLFFRKSIINFEKL (SEQ ID NO:903) | 82 ± 4 | 445 ± 30 | 1.3 ± 0.41 | 0 ± 0 |
| 9.6 µg NLLRLTGWFFRKSIINFEKLFFRKRGYVYQGL (SEQ ID NO:900) plus 9.6 µg NLLRLTGWFFRKRGYVYQGLFFRKSIINFEKL (SEQ ID NO:903) | 202 ± 7.6 | 188 ± 24 | 1.0 ± 0.7 | 0.67 ± 0.41 |

S200-72-13, no ADP

| Immunogen | Number of Spots per 300,000 cells | | | |
|---|---|---|---|---|
| | SIINFEKL (SEQ ID NO:868) | RGYVYQGL (SEQ ID NO:879) | IAYFYPEL (SEQ ID NO:904) | Medium |
| 9.6 µg NLLRLTGWFFRKSIINFEKLFFRKRGYVYQGL (SEQ ID NO:900) | 228 ± 2.5 | 126 ± 2.9 | 1.7 ± 0.4 | 0 ± 0 |
| 9.6 µg NLLRLTGWFFRKRGYVYQGLFFRKSIINFEKL (SEQ ID NO:903) | 83 ± 9 | 189 ± 19 | 13 ± 15 | 0.33 ± 0.41 |
| 9.6 µg NLLRLTGWFFRKSIINFEKLFFRKRGYVYQGL (SEQ ID NO:900) plus 9.6 µg NLLRLTGWFFRKRGYVYQGLFFRKSIINFEKL (SEQ ID NO:903) | 115 ± 7.8 | 86 ± 11 | 0.33 ± 0.41 | 0 ± 0 |

EXAMPLE 23

In the following experiment, up to five antigenic peptides are delivered and induce immunogenicity without co-administered HSP70, when administered as an admixture of two tandem hybrid antigens and a single hybrid antigen to B6 mice. The tandem hybrid antigens included VSV and ovalbumin peptides in one, and β-casein and Sendai virus peptides in the other. The single hybrid antigen contained NS2-114 influenza peptide (RTFSFQLI) (SEQ ID NO:906).

S200-72-15

| Immunogen | Number of Spots per 300,000 cells | | | | |
|---|---|---|---|---|---|
| | SIINFEKL (SEQ ID NO:868) | RGYVYQGL (SEQ ID NO:879) | IAYFYPEL (SEQ ID NO:904) | FAPGNYPAL (SEQ ID NO:891) | RTFSFQLI (SEQ ID NO:906) |
| 9.6 µg NLLRLTGWFFRKRGYVYQGL FFRKSIINFEKL (SEQ ID NO:903) plus | 67 ± 6.1 | 205 ± 20 | 229 ± 28 | 266 ± 33 | 0 ± 0 |

-continued

| Immunogen | Number of Spots per 300,000 cells | | | | |
|---|---|---|---|---|---|
| | SIINFEKL (SEQ ID NO:868) | RGYVYQGL (SEQ ID NO:879) | IAYFYPEL (SEQ ID NO:904) | FAPGNYPAL (SEQ ID NO:891) | RTFSFQLI (SEQ ID NO:906) |
| 19 µg NLLRLTGWFFRKIAYFYPELF FRKFAPGNYPAL (SEQ ID NO:905) | | | | | |
| 9.6 µg NLLRLTGWFFRKRGYVYQGL FFRKSIINFEKL (SEQ ID NO:903) plus 19 µg NLLRLTGWFFRKIAYFYPELF FRKFAPGNYPAL (SEQ ID NO:905) plus 12.2 µg NLLRLTGWFFRKRTFSFQLI (SEQ ID NO:907) | 156 ± 3.3 | 299 ± 18 | 175 ± 12 | 125 ± 3.3 | 33 ± 4.7 |

EXAMPLE 24

The immunogenicity of the foregoing single hybrid antigens administered without heat shock protein were evaluated in combination with helper T cell epitopes present in a hybrid antigen. In most experiments, a H2-K$^b$ Class II epitope from ovalbumin, amino acids 323-339, TEWTSSNVMEERKIKV (SEQ ID NO:908), was used (i.e., the hybrid antigen had a sequence of NLLRLTGWFFRK-TEWTSSNVMEERKIKV) (SEQ ID NO:909). Inclusion of the Class II peptide-containing hybrid antigen increased the response to the Class I epitope on the average of about seven fold.

(250-72-08)

| Class I hybrid peptide-containing immunogen | Number of Spots per 300,000 cells | | | |
|---|---|---|---|---|
| | Response to Class I epitope when Class I hybrid antigen administered | Response to Class I epitope when Class I and Class II hybrid antigen admixture is administered | Medium | Splenocytes |
| 24.2 µg NLLRLTGWFFRKDAPIYTNV (SEQ ID NO:910) | 2 ± 1.9 | 13 ± 3.9 | 0.7 ± 0.4 | 0 ± 0 |
| 24.9 µg NLLRLTGWFFRKSSWDFITV (SEQ ID NO:911) | 18 ± 0.7 | 98 ± 5.8 | 0.7 ± 0.8 | 0.7 ± 0.4 |
| 25.4 µg NLLRLTGWFFRKRTFSFQLI (SEQ ID NO:912) | 5.3 ± 1.5 | 43 ± 7.6 | 0.3 ± 0.4 | 0 ± 0 |
| 25.5 µg NLLRLTGWFFRKIAYFYPEL (SEQ ID NO:913) | 11 ± 3 | 73 ± 9.8 | 0 ± 0 | 0 ± 0 |

EXAMPLE 25

The effect on immunogenicity of hybrid antigens co-administered with various hybrid antigens containing H2-Kb Class II peptides, in the absence of heat shock protein, were evaluated. The Class I peptides were either SSWDFITV (SEQ ID NO:914) or DAPIYTNV (SEQ ID NO:915); Class II peptides included the ovalbumin peptide mentioned above, a Class II peptide from tetanus toxoid NNFFVSFWLRVPKVSASHL (SEQ ID NO:916) (i.e., the hybrid antigen has a sequence of NLLRLTGWFFRKNN-FTVSFWLRVPKVSASHL (SEQ ID NO:917)), or a HBVc (amino acids 128-140) peptide, TPPAYRPPNAPIL (SEQ ID NO:918).

250-72-13

| Immunogen | Number of Spots per 300,000 cells | |
|---|---|---|
| | Medium | SSWDFITV (SEQ ID NO:914) |
| 24.9 µg NLLRLTGWFFRKSSWDFITV (SEQ ID NO:911) | 3.9 ± 0.7 | 78 ± 3.9 |
| 24.9 µg NLLRLTGWFFRKSSWDFITV (SEQ ID NO:911) plus 27.4 µg NLLRLTGWFFRKTPPAYRPPNAPIL (SEQ ID NO:925) | 8.0 ± 3.1 | 84 ± 7.1 |
| 24.9 µg NLLRLTGWFFRKSSWDFITV (SEQ ID NO:911) plus 33.6 µg NNFTVSFWLRVPKVSASHLGSGNLLRLTGW (SEQ ID NO:926) | 3.7 ± 1.1 | 315 ± 15 |
| 24.9 µg NLLRLTGWFFRKSSWDFITV (SEQ ID NO:911) plus 36.4 µg HWDFAWPWNGSGNNFTVSFWLRVPKVSASHL (SEQ ID NO:919) | 2.7 ± 2.0 | 135 ± 5.7 |
| 24.9 µg NLLRLTGWFFRKSSWDFITV (SEQ ID NO:911) plus 34.7 µg NLLRLTGWFFRKTEWTSSNVMEERKIKV (SEQ ID NO:909) | 1.7 ± 0.4 | 229 ± 12 |

Thus, a helper T cell epitope may be included in a hybrid antigen as the only epitope, and administered as an admixture with other hybrid antigens containing Class I epitope(s), or the helper T cell epitope can be included in a tandem hybrid antigen as one of the epitopes. These are merely exemplary of the numerous variations upon the hybrid antigen compositions of the invention.

EXAMPLE 26

In a similar fashion to the previous example, the immunogenicity of a tandem hybrid antigen was evaluated with and without co-administration of a hybrid antigen containing the ovalbumin Class II peptide.

S250-72-12

| Immunogen | Number of Spots per 300,000 cells | | |
|---|---|---|---|
| | IAYFYPEL (SEQ ID NO:904) | FAPGNYPAL (SEQ ID NO:906) | Medium |
| 19 µg MLLRLTGWFFRKIAYFYPELFFRKFAPGNYPAL (SEQ ID NO:905) | 9.3 ± 4.7 | 17 ± 9 | 0.7 ± 0.6 |
| 19 µg NLLRLTGWFFRKIAYFYPELFFRKFAPGNYPAL (SEQ ID NO:905) Plus 20.8 µg NLLRLTGWFFRKTEWTSSNVMEERKIKV (SEQ ID NO:909) | 44 ± 5.1 | 58 ± 5.2 | 0.7 ± 0.6 |

| Immunogen | Number of Spots per 300,000 cells TAYFYPEL (SEQ ID NO:904) |
|---|---|
| 25.5 µg NLLRLTGWFFRKIAYFYPEL (SEQ ID NO:9 13) | 3.7 ± 3.1 |
| 25.5 µg NLLRLTGWFFRKIAYFYPEL (SEQ ID NO:913) plus 34.7 µg NLLRLTGWFFRKTEWTSSNVMEERKIKV (SEQ ID NO:909) | 133 ± 11 |
| 25.5 µg NLLRLTGWFFRKIAYFYPEL (SEQ ID NO:913) plus 25 Mg NLLRLTGWFFRKSIINFEKL (SEQ ID NO:881) | 88 ± 9.9 |

EXAMPLE 27

Similar experiments with hybrid antigens comprising a helper T cell epitope co-administered with at least one tandem hybrid antigen, in the absence of co-administration of a heat shock protein, were also carried out.

EXAMPLE 28

An immunization study using hybrid antigens containing human Class I (HLA-A2) epitopes was performed in HHD II mice as described above. Animals were immunized with a complex made from 5 µg hsp70 and 33 µg NLLRLTGWFFRKYMDGTMSQV (SEQ ID NO:890). The ELISPOT results in cells per 300,000 were: Medium, 1.33±0.58; splenocytes 1±0; splenocytes plus YMDGTMSQV (SEQ ID NO:875) 123±13; and splenocytes plus IMDQVPFSV (SEQ ID NO:874) 4±1.

EXAMPLE 29

In another experiment using HHDII mice, an immunogenic HLA-A2 epitope from Trp-2 was used (SVYDFFVWL) (SEQ ID NO:920). Because this epitope is also a H2-Kb epitope, and the HHDII mice are on a B6 mouse (H2-Kb) background, an immune response induced against the Trp-2 peptide represents a breaking of tolerance to a self-epitope in the mouse model. The results of this experiment demonstrated that tolerance to this self-epitope was broken, and the present invention is further directed to methods of breaking tolerance by administering the hybrid antigens and complexes of the invention.

| Immunogen | Number of Spots per 300,000 cells | | | | |
|---|---|---|---|---|---|
| | Medium | SIINFEKL (SEQ ID NO:868) | RGYVYQGL (SEQ ID NO:879) | IAYFYPEL (SEQ ID NO:904) | FAPGNYPAL (SEQ ID NO:906) |
| 24 µg NLLRLTGWFFRKIAYFYPELF FRKFAPGNYPAL (SEQ ID NO:905) | 0.7 ± 0.6 | NT | NT | 9.3 ± 4.7 | 17 ± 8.7 |
| 24 µg NLLRLTGWFFRKIAYFYPELF FRKFAPGNYPAL (SEQ ID NO:905) plus 21 µg NLLRLTGWFFRKTEWTSSNV MEERKIKV (SEQ ID NO:909) | 0.7 ± 0.6 | NT | NT | 44 ± 5.1 | 67 ± 5.5 |
| 15 µg NLLRLTGWFFRKFAPGNYPAL (SEQ ID NO:892) plus 15 µg NLLRLTGWFFRKFAPGNYPAL (SEQ ID NO:892) plus 21 µg NLLRLTGWFFRKTEWTSSNV MEERKIKV (SEQ ID NO:909) | 0 ± 0 | NT | NT | 0.3 ± 0.6 | 4.3 ± 3.2 |
| | 0 ± 0 | NT | NT | 2.3 ± 2.1 | 58 ± 5.2 |

|  | Number of Spots per 300,000 cells | | | |
|---|---|---|---|---|
| Immunogen | Medium | SVYDFFVWL (SEQ ID NO:920) | IMDQVPFSV (SEQ ID NO:874) | YMDGTMSQV (SEQ ID NO:875) |
| 4.33 µg NLLRLTGWFFRKSVYDFFVWL (SEQ ID NO:895) plus 25 µg hsp70 | 0.5 ± 0.71 | 166 ± 25 | 2.0 ± 1.4 | 3.5 ± 0.71 |
| 8.66 µg NLLRLTGWFFRKSVYDFFVWL (SEQ ID NO:895) plus 25 µg hsp70 | 3.5 ± 0.71 | 114 ± 11 | 7.7 ± 2.1 | 11 ± 3.1 |
| 4.1 µg NLLRLTGWFFRKYMDGTMSQV (SEQ ID NO:890) plus 25 µg hsp70 | 3.0 | 1.0 | 2.0 ± 1.4 | 74 ± 2.8 |
| 4.1 µg NLLRLTGWFFRKIMDQVPQV (SEQ ID NO:890) plus 25 µg hsp70 | 1.0 ± 1.4 | 2.0 ± 2.0 | 984 ± 26 | 2.3 ± 1.5 |

EXAMPLE 30

HHDII mice were used to evaluate the immunogenicity of complexes of hsp70 and three hybrid antigens comprising certain of the HIV viral component epitopes set forth in Example 27.

HHDII-200-72-07

|  | Number of Spots per 300,000 cells | | | |
|---|---|---|---|---|
| Immunogen | Medium | ILKEPVHGV (SEQ ID NO:98) | VIYQYMDDL (SEQ ID NO:921) | SLYNTVATL (SEQ ID NO:131) |
| 36 µg NLLRLTGWFFR KILKEPVHGV (SEQ ID NO:922) + 25 µg hsp70 | 1.0 ± 1.0 | 34 ± 12 | 0 ± 0 | NT |
| 36 µg NLLRLTGWFFR KVIYQYMDDL (SEQ ID NO:923) + 25 µg hsp70 | 0 ± 0 | 0.67 ± 0.58 | 24 ± 6.1 | NT |
| 36 µg NLLRLTGWFFR KSLYNTVATL (SEQ ID NO:924) + 25 µg hsp70 | 0.67 ± 0.58 | NT | NT | 140 ± 6.7 |

NT = not tested

EXAMPLE 31

Admixtures of hybrid antigens containing H2-Kb epitopes complexed with hsp70 were evaluated for immunogenicity in B6 mice as described above.

OBS-72-01

| | Number of Spots per 300,000 cells | | | | |
|---|---|---|---|---|---|
| Immunogen | Medium | Splenocytes | SIINFEKL (SEQ ID NO:868) | FAPGNYPAL (SEQ ID NO:906) | IAYFYPEL (SEQ ID NO:904) |
| 2 µg NLLRLTGWFFRKSIINFEKL (SEQ ID NO:881) + 13.7 µg hsp70 | 1 | 2 ± 1 | 148 ± 11 | 7 ± 2 | 3 ± 2 |
| 10 µg NLLRLTGWFFRKIAYFYPEL (SEQ ID NO:913) + 13.7 µg hsp70 | 0 | 2 ± 2 | 3 ± 1 | 8 ± 2 | 47 ± 13 |
| 10 µg NLLRLTGWFFRKFAPGNYPAL (SEQ ID NO:892) + 13.7 µg hsp70 | 3 | 3 ± 3 | 3 ± 2 | 83 ± 6 | 6 ± 1 |
| 2 µg NLLRLTGWFFRKSIINFEKL (SEQ ID NO:881) + 10 µg NLLRLTGWFFRKIAYFYPEL (SEQ ID NO:913) + 27.4 µg hsp70 | 2 | 4 ± 2 | 94 ± 4 | 9 ± 3 | 29 ± 4 |
| 2 µg NLLRLTGWFFRKSIINFEKL (SEQ ID NO:881) + 10 µg NLLRLTGWFFRKFAPGNYPAL (SEQ ID NO:892) + 27.4 µg hsp70 | 3 | 3 ± 0 | 169 ± 7 | 157 ± 27 | 4 ± 2 |
| 10 µg NLLRLTGWFFRKIAYFYPEL (SEQ ID NO:8913) + 10 µg NLLRLTGWFFRKFAPGNYPAL (SEQ ID NO:892) + 27.4 µg hsp70 | 3 | 3 ± 3 | 4 ± 3 | 46 ± 8 | 39 ± 2 |
| 2 µg NLLRLTGWFFRKSIINFEKL (SEQ ID NO:881) + 10 µg NLLRLTGWFFRKIAYFYPEL (SEQ ID NO:913) + 10 µg NLLRLTGWFFRJKFAPGNYPAL (SEQ ID NO:892) + 41 µg hsp70 | 1 | 5 ± 2 | 149 ± 19 | 61 ± 5 | 60 ± 7 |

EXAMPLE 32

The immunogenicity of tandem hybrid antigens complexed with hsp70 was studied in B6 mice.

S200-72-01

| | Number of Spots per 300,000 cells | | | |
|---|---|---|---|---|
| Immunogen | Medium control | Unpulsed control | SIINFEKL (SEQ ID NO:868) | RGYVYQGL (SEQ ID NO:879) |
| 5.6 µg hsp70 + 3 µg NLLRLTGWFFRKSIINFEKL (SEQ ID NO:881) | 0.33 ± 0.41 | 0.67 ± 0.41 | 43 ± 9.2 | 1 ± 0 |

-continued

| Immunogen | Number of Spots per 300,000 cells | | | |
|---|---|---|---|---|
| | Medium control | Unpulsed control | SIINFEKL (SEQ ID NO:868) | RGYVYQGL (SEQ ID NO:879) |
| 11.2 μg hsp70 +<br>5.9 μg NLLRLTGWFFRKRGYVYQGL<br>(SEQ ID NO:901) | 0.33 ± 0.41 | 0.33 ± 0.41 | 1 ± 0.71 | 102 ± 16 |
| 11.2 μg hsp70 +<br>3 μg NLLRLTGWFFRKSIINFEKL<br>(SEQ ID NO:881) +<br>5.9 μg NLLRLTGWFFRKRGYVYQGL<br>(SEQ ID NO:901) | 0.67 ± 0.82 | 1.7 ± 0.41 | 182 ± 11 | 113 ± 10 |
| 5.6 μg hsp70 +<br>4.8 μg NLLRLTGWFFRKSIINFEKLFFRKRGYVYQGL<br>(SEQ ID NO:902) | 0 ± 0 | 4 ± 1.4 | 456 ± 19 | 113 ± 1.1 |
| 11.2 μg hsp70 +<br>9.6 μg NLLRLTGWFFRKSIINFEKLFFRKRGYVYQGL<br>(SEQ ID NO:902) | 0 ± 0 | 10 ± 3.3 | 505 ± 57 | 90 ± 11 |
| 22.4 μg hsp70 +<br>19.2 μg NLLRLTGWFFRKSIINFEKLFFRKRGYVYQGL<br>(SEQ ID NO:902) | 0.67 ± 0.82 | 1.7 ± 0.41 | 289 ± 26 | 130 ± 12 |
| 5.6 μg hsp70 +<br>4.8 μg NIIRLTGWFFRKRGYVYQGLFFRKSHNFEKL<br>(SEQ ID NO:903) | 0.33 ± 0.41 | 2.3 ± 0.41 | 72 ± 9.5 | 98 ± 9.2 |
| 11.2 μg hsp70 +<br>9.6 μg NLLRLTGWFFRKRGYVYQGLFFRKSIINFEKL<br>(SEQ ID NO:903) | 2 ± 0 | 2.3 ± 1.5 | 370 ± 16 | 617 ± 23 |
| 22.4 μg hsp70 +<br>19.3 μg NLLRLTGWFFRKRGYVYQGLFFRKSIINFEKL<br>(SEQ ID NO:903) | 0.67 ± 0.41 | 4.0 ± 2.1 | 336 ± 7.8 | 728 ± 12 |

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the contents of which are incorporated herein by reference in their entireties.

What is claimed is:

1. A hybrid antigen comprising at least one antigenic domain of an infectious agent or tumor antigen, at least one binding domain that non-covalently binds to a heat shock protein, and at least one peptide linker there between consisting of Phe Phe Arg Lys (SEQ ID NO:699).

2. A composition comprising at least one hybrid antigen of claim 1 and a pharmaceutically acceptable carrier.

3. A composition comprising a non-covalent complex of at least one hybrid antigen of claim 1 and at least one said heat shock protein; and a pharmaceutically acceptable carrier.

4. The composition of claim 3 wherein the at least one said heat shock protein is a hsp70 family member.

5. A method for inducing an immune response in a subject to an infectious agent comprising administering to the subject at least one hybrid antigen of claim 1, wherein said at least one hybrid antigen comprises at least one antigenic domain of said infectious agent.

6. A method for inducing an immune response in a subject to an infectious agent comprising administering to the subject a complex of:
  (a) at least one hybrid antigen of claim 1, wherein said at least one hybrid antigen comprises at least one antigenic domain of said infectious agent; and
  (b) at least one said heat shock protein;
wherein the hybrid antigen and the at least one said heat shock protein are non-covalently bound.

7. The method of claim 6 wherein the at least one said heat shock protein is a hsp70 family member.

8. A method for treating an infectious disease comprising administering to a subject having an infectious disease at least one hybrid antigen of claim 1, which said at least one hybrid antigen comprises at least one antigenic domain of an infectious agent, and wherein said infectious agent causes said infectious disease.

9. A method for treating an infectious disease comprising administering to a subject having an infectious disease a complex of:
  (a) at least one hybrid antigen of claim 1, wherein said at least one hybrid antigen comprises at least one antigenic domain of an infectious agent, and wherein said infectious agent causes said infectious disease; and
  (b) at least one said heat shock protein;
wherein the hybrid antigen and the at least one said heat shock protein are non-covalently bound.

10. The method of claim 9 wherein the at least one said heat shock protein is a hsp70 family member.

11. A hybrid antigen consisting essentially of at least one antigenic domain of an infectious agent or tumor antigen, at least one binding domain that non-covalently binds to a heat shock protein, and at least one peptide linker there between, wherein said peptide linker consists of Phe Phe Arg Lys (SEQ ID NO:699).

12. A composition comprising at least one hybrid antigen of claim 11, and a pharmaceutically acceptable carrier.

13. A composition comprising a complex of at least one hybrid antigen of claim 11 and at least one said heat shock protein; and a pharmaceutically acceptable carrier.

14. The composition of claim 13 wherein the at least one said heat shock protein is a hsp70 family member.

15. A method for inducing an immune response in a subject to an infectious agent comprising administering to the subject at least one hybrid antigen of claim 11, wherein said at least one hybrid antigen comprises at least one antigenic domain of said infectious agent.

16. A method for inducing an immune response in a subject to an infectious agent comprising administering to the subject a complex of:
  (a) at least one hybrid antigen of claim 11, wherein said at least one hybrid antigen comprises at least one antigenic domain of said infectious agent; and
  (b) at least one said heat shock protein;
wherein the hybrid antigen and the at least one said heat shock protein are non-covalently bound.

17. The method of claim 16 wherein the at least one said heat shock protein is a hsp70 family member.

18. A method for treating an infectious disease comprising administering to a subject having an infectious disease at least one hybrid antigen of claim 11, wherein said at least one hybrid antigen comprises at least one antigenic domain of an infectious agent, and wherein said infectious agent causes said infectious disease.

19. A method for treating an infectious disease comprising administering to a subject having an infectious disease a complex of:
  (a) at least one hybrid antigen of claim 11, wherein said at least one hybrid antigen comprises at least one antigenic domain of an infectious agent, and wherein said infectious agent causes said infectious disease; and
  (b) at least one said heat shock protein;
wherein the hybrid antigen and the at least one said heat shock protein are non-covalently bound.

20. The method of claim 19 wherein the at least one said heat shock protein is a hsp70 family member.

21. A method for inducing an immune response in a subject to a tumor antigen comprising administering to the subject at least one hybrid antigen of claim 1 or 11, wherein said at least one hybrid antigen comprises at least one antigenic domain of said tumor antigen.

22. A method for inducing an immune response in a subject to a tumor antigen comprising administering to a subject a complex of:
(a) at least one hybrid antigen of claim 1 or 11, wherein said at least one hybrid antigen comprises at least one antigenic domain of said tumor antigen; and
(b) at least one said heat shock protein;
wherein the hybrid antigen and the at least one said heat shock protein are non-covalently bound.

23. The method of claim 22 wherein the at least one said heat shock protein is a hsp70 family member.

24. The hybrid antigen of claim 1 or 11, wherein said hybrid antigen is in the range of 10-500 amino acids.

25. The hybrid antigen of claim 1 or 11, wherein said antigenic domain is of an infectious agent.

26. The hybrid antigen of claim 1 or 11, wherein said antigenic domain is of a tumor antigen associated with a cancer.

27. The hybrid antigen of claim 26, wherein the cancer is selected from the group consisting of sarcoma, lymphoma, leukemia, melanoma, carcinoma of the breast, carcinoma of the prostate, ovarian carcinoma, carcinoma of the cervix, uterine carcinoma, colon carcinoma, carcinoma of the lung, glioblastoma, and astrocytoma.

28. The hybrid antigen of claim 25, wherein the infectious agent is selected from the group consisting of a bacterium, a virus, a protozoan, a mycoplasma, a fungus, a yeast, a parasite, and a prion.

29. The hybrid antigen of claim 28, wherein the infectious agent is a bacterium.

30. The hybrid antigen of claim 29, wherein the bacterium is selected from the group consisting of *Salmonella, Staphylococcus, Streptococcus, Enterococcus, Clostridium, Escherichia, Kiebsiella, Vibrio, Mycobacterium*, and *Mycoplasma pneumoniae*.

31. The hybrid antigen of claim 28, wherein the infectious agent is a virus.

32. The hybrid antigen of claim 31, wherein the virus is selected from the group consisting of a human papilloma virus, herpes virus, retrovirus, hepatitis virus, influenza virus, rhinovirus, respiratory syncytial virus, cytomegalovirus, adenovirus, herpes simplex virus, herpes zoster virus, human immunodeficiency virus 1, and human immunodeficiency virus 2.

33. The hybrid antigen of claim 28, wherein the infectious agent is a protozoan.

34. The hybrid antigen of claim 33, wherein the protozoan is selected from the group consisting of an amoeba, a malarial parasite, and *Trypanosoma cruzi*.

35. The composition of claim 4 or 14, wherein the hsp70 family member is BiP, hsp70 or hsc70.

36. The composition of claim 3 or 13 further comprising one or more adjuvants.

37. The composition of claim 4 or 14 further comprising one or more adjuvants.

38. A composition comprising a plurality of the hybrid antigen of claim 1 or 11.

39. The composition of claim 38 further comprising a plurality of heat shock proteins non-covalently complexed to the hybrid antigens.

40. The method of claim 5, 6, 15 or 16 wherein the subject is a human.

41. The method of claim 21 wherein the subject is a human.

42. The method of claim 22 wherein the subject is a human.

43. The composition of claim 3 or 13, wherein the at least one said heat shock protein is gp96, hsp60, hsp40 or hsp90.

44. The hybrid antigen of claim 1 or 11, which comprises at least two antigenic domains, wherein each of said at least two antigenic domains is separated by a second peptide linker, and wherein each said second peptide linker is independently selected from the group consisting of Phe Phe Arg Lys (SEQ ID NO:699); Phe Arg Lys; Phe Arg Lys Asn (SEQ ID NO:701); Arg Lys Asn; Phe Phe Arg Lys Asn (SEQ ID NO:702); Phe Arg; Gln Leu Lys; Gln Leu Glu; Lys Asn; Arg Lys; and $AA_1$-$AA_2$-$AA_3$-leucine (SEQ ID NO:9), wherein $AA_1$ is Ala, Ser, Val, Glu, Gly, Leu, or Lys, $AA_2$ is Lys, Val, or Glu, and $AA_3$ is Val, Ser, Phe, Lys, Ala, Glu, or Thr.

45. The hybrid antigen of claim 1 or 11, which comprises two antigenic domains separated by a second peptide linker, wherein said second peptide linker is selected from the group consisting of Phe Phe Arg Lys (SEQ ID NO:699); Phe Arg Lys; Phe Arg Lys Asn (SEQ ID NO:701); Arg Lys Asn; Phe Phe Arg Lys Asn (SEQ ID NO:702); Phe Arg; Gln Leu Lys; Gln Leu Glu; Lys Asn; Mg Lys; and $AA_1$-$AA_2$-$AA_3$-leucine (SEQ ID NO:9), wherein $AA_1$ is Ala, Ser, Val, Glu, Gly, Leu, or Lys, $AA_2$ is Lys, Val, or Glu, and $AA_3$ is Val, Ser, Phe, Lys, Ala, Glu, or Thr.

46. The hybrid antigen of claim 44, wherein at least one of the second peptide linkers is Phe Phe Arg Lys (SEQ ID NO:699).

47. The hybrid antigen of claim 45, wherein the second peptide linker is Phe Phe Arg Lys (SEQ ID NO:699).

\* \* \* \* \*

SEQUENCE LISTING

```
<160> NUMBER OF SEQ ID NOS: 926

<210> SEQ ID NO 1
<211> LENGTH: 4
<212> TYPE: PRT
<213> ORGANISM: Malaria

<400> SEQUENCE: 1

Asn Ala Asn Pro
 1

<210> SEQ ID NO 2
<211> LENGTH: 9
<212> TYPE: PRT
<213> ORGANISM: Unknown
<220> FEATURE:
<223> OTHER INFORMATION: HLA-A2 peptide binding motif
<220> FEATURE:
<221> NAME/KEY: VARIANT
<222> LOCATION: 2
```

```
<223> OTHER INFORMATION: Xaa = Leu or Met
<220> FEATURE:
<221> NAME/KEY: VARIANT
<222> LOCATION: 6
<223> OTHER INFORMATION: Xaa = Val or Ile or Leu or Thr
<220> FEATURE:
<221> NAME/KEY: VARIANT
<222> LOCATION: 9
<223> OTHER INFORMATION: Xaa = Val or Leu
<220> FEATURE:
<221> NAME/KEY: VARIANT
<222> LOCATION: 1,3 , 4, 5, 7, 8
<223> OTHER INFORMATION: Xaa = any amino acid

<400> SEQUENCE: 2

Xaa Xaa Xaa Xaa Xaa Xaa Xaa Xaa Xaa
 1               5

<210> SEQ ID NO 3
<211> LENGTH: 9
<212> TYPE: PRT
<213> ORGANISM: Unknown
<220> FEATURE:
<223> OTHER INFORMATION: HLA-A2 peptide binding motif
<220> FEATURE:
<221> NAME/KEY: VARIANT
<222> LOCATION: 2
<223> OTHER INFORMATION: Xaa = Leu or Met
<220> FEATURE:
<221> NAME/KEY: VARIANT
<222> LOCATION: 1, 3, 4, 5, 6, 7, 8
<223> OTHER INFORMATION: Xaa = any amino acid

<400> SEQUENCE: 3

Xaa Xaa Xaa Xaa Xaa Xaa Xaa Xaa Val
 1               5

<210> SEQ ID NO 4
<211> LENGTH: 8
<212> TYPE: PRT
<213> ORGANISM: Unknown
<220> FEATURE:
<223> OTHER INFORMATION: HLA-A2 peptide binding motif
<220> FEATURE:
<221> NAME/KEY: VARIANT
<222> LOCATION: 2
<223> OTHER INFORMATION: Xaa = Val or Gln
<220> FEATURE:
<221> NAME/KEY: VARIANT
<222> LOCATION: 1, 3, 4, 5, 6, 7
<223> OTHER INFORMATION: Xaa = any amino acid

<400> SEQUENCE: 4

Xaa Xaa Xaa Xaa Xaa Xaa Xaa Leu
 1               5

<210> SEQ ID NO 5
<211> LENGTH: 5
<212> TYPE: PRT
<213> ORGANISM: Unknown
<220> FEATURE:
<223> OTHER INFORMATION: HLA-DR peptide binding motif

<400> SEQUENCE: 5

Gln Lys Arg Ala Ala
 1               5

<210> SEQ ID NO 6
<211> LENGTH: 5
<212> TYPE: PRT
<213> ORGANISM: Unknown
```

```
<220> FEATURE:
<223> OTHER INFORMATION: HLA-DR peptide binding motif

<400> SEQUENCE: 6

Arg Arg Arg Ala Ala
 1               5

<210> SEQ ID NO 7
<211> LENGTH: 7
<212> TYPE: PRT
<213> ORGANISM: Unknown
<220> FEATURE:
<223> OTHER INFORMATION: motif in heptamiric region  recognized by heat
      shock protein
<220> FEATURE:
<221> NAME/KEY: VARIANT
<222> LOCATION: 2
<223> OTHER INFORMATION: Xaa = Trp or any amino acid
<220> FEATURE:
<221> NAME/KEY: VARIANT
<222> LOCATION: 1, 3, 5, 7
<223> OTHER INFORMATION: Xaa = hydrophobic amino acid residues
<220> FEATURE:
<221> NAME/KEY: VARIANT
<222> LOCATION: 4, 6
<223> OTHER INFORMATION: Xaa = any amino acid

<400> SEQUENCE: 7

Xaa Xaa Xaa Xaa Xaa Xaa Xaa
 1               5

<210> SEQ ID NO 8
<211> LENGTH: 7
<212> TYPE: PRT
<213> ORGANISM: Unknown
<220> FEATURE:
<223> OTHER INFORMATION: motif in heptamiric region  recognized by heat
      shock protein
<220> FEATURE:
<221> NAME/KEY: VARIANT
<222> LOCATION: 2
<223> OTHER INFORMATION: Xaa = Trp or any amino acid
<220> FEATURE:
<221> NAME/KEY: VARIANT
<222> LOCATION: 1, 3, 5, 7,
<223> OTHER INFORMATION: Xaa = hydrophobic amino acid residue,
      particularly tryptophan, leucine or phenylalanine
<220> FEATURE:
<221> NAME/KEY: VARIANT
<222> LOCATION: 4, 6
<223> OTHER INFORMATION: Xaa = any amino acid

<400> SEQUENCE: 8

Xaa Xaa Xaa Xaa Xaa Xaa Xaa
 1               5

<210> SEQ ID NO 9
<211> LENGTH: 4
<212> TYPE: PRT
<213> ORGANISM: Artificial Sequence
<220> FEATURE:
<223> OTHER INFORMATION: peptide linker in between antigenic domain and
      heat shock binding domain of hybrid antigen
<220> FEATURE:
<221> NAME/KEY: VARIANT
<222> LOCATION: 1
<223> OTHER INFORMATION: Xaa = Ala/Ser/Val/Lys/Glu/Gly/Leu
<220> FEATURE:
<223> OTHER INFORMATION: In the order of preference, with Ala the most
      preferred
<220> FEATURE:
<221> NAME/KEY: VARIANT
<222> LOCATION: 2
```

```
<223> OTHER INFORMATION: Xaa = Lys/Val/Glu
<220> FEATURE:
<223> OTHER INFORMATION: In the order of preference, with Lys the most
      preferred
<220> FEATURE:
<221> NAME/KEY: VARIANT
<222> LOCATION: 3
<223> OTHER INFORMATION: Xaa = Val/Ser/Phe/Thr/Lys/Ala/Glu
<220> FEATURE:
<223> OTHER INFORMATION: In the order of preference, with Val the most
      preferred

<400> SEQUENCE: 9

Xaa Xaa Xaa Leu
 1

<210> SEQ ID NO 10
<211> LENGTH: 10
<212> TYPE: PRT
<213> ORGANISM: Adeno Virus

<400> SEQUENCE: 10

Ser Gly Pro Ser Asn Thr Pro Pro Glu Ile
 1               5                  10

<210> SEQ ID NO 11
<211> LENGTH: 11
<212> TYPE: PRT
<213> ORGANISM: Lymphocytic Choriomeningitis Virus (LCMV)

<400> SEQUENCE: 11

Ser Gly Val Glu Asn Pro Gly Gly Tyr Cys Leu
 1               5                  10

<210> SEQ ID NO 12
<211> LENGTH: 10
<212> TYPE: PRT
<213> ORGANISM: Lymphocytic Choriomeningitis Virus (LCMV)

<400> SEQUENCE: 12

Lys Ala Val Tyr Asn Phe Ala Thr Cys Gly
 1               5                  10

<210> SEQ ID NO 13
<211> LENGTH: 9
<212> TYPE: PRT
<213> ORGANISM: Lymphocytic Choriomeningitis Virus (LCMV)

<400> SEQUENCE: 13

Arg Pro Gln Ala Ser Gly Val Tyr Met
 1               5

<210> SEQ ID NO 14
<211> LENGTH: 9
<212> TYPE: PRT
<213> ORGANISM: Lymphocytic Choriomeningitis Virus (LCMV)

<400> SEQUENCE: 14

Phe Gln Pro Gln Asn Gly Gln Phe Ile
 1               5

<210> SEQ ID NO 15
<211> LENGTH: 9
<212> TYPE: PRT
<213> ORGANISM: Influenza Virus

<400> SEQUENCE: 15
```

```
Ile Glu Gly Gly Trp Thr Gly Met Ile
1               5
```

<210> SEQ ID NO 16
<211> LENGTH: 10
<212> TYPE: PRT
<213> ORGANISM: Influenza Virus

<400> SEQUENCE: 16

```
Thr Tyr Val Ser Val Ser Thr Ser Thr Leu
1               5                   10
```

<210> SEQ ID NO 17
<211> LENGTH: 8
<212> TYPE: PRT
<213> ORGANISM: Influenza Virus

<400> SEQUENCE: 17

```
Phe Glu Ala Asn Gly Asn Leu Ile
1               5
```

<210> SEQ ID NO 18
<211> LENGTH: 9
<212> TYPE: PRT
<213> ORGANISM: Influenza Virus

<400> SEQUENCE: 18

```
Ile Tyr Ser Thr Val Ala Ser Ser Leu
1               5
```

<210> SEQ ID NO 19
<211> LENGTH: 9
<212> TYPE: PRT
<213> ORGANISM: Influenza Virus

<400> SEQUENCE: 19

```
Thr Tyr Gln Arg Thr Arg Ala Leu Val
1               5
```

<210> SEQ ID NO 20
<211> LENGTH: 9
<212> TYPE: PRT
<213> ORGANISM: Influenza Virus

<400> SEQUENCE: 20

```
Cys Thr Glu Leu Lys Leu Ser Asp Tyr
1               5
```

<210> SEQ ID NO 21
<211> LENGTH: 8
<212> TYPE: PRT
<213> ORGANISM: Influenza Virus

<400> SEQUENCE: 21

```
Ser Asp Tyr Glu Gly Arg Leu Ile
1               5
```

<210> SEQ ID NO 22
<211> LENGTH: 9
<212> TYPE: PRT
<213> ORGANISM: Influenza Virus

<400> SEQUENCE: 22

Glu Glu Gly Ala Ile Val Gly Glu Ile

-continued

```
<210> SEQ ID NO 23
<211> LENGTH: 9
<212> TYPE: PRT
<213> ORGANISM: Influenza Virus

<400> SEQUENCE: 23

Val Ser Asp Gly Gly Pro Asn Leu Tyr
1               5

<210> SEQ ID NO 24
<211> LENGTH: 9
<212> TYPE: PRT
<213> ORGANISM: Influenza Virus

<400> SEQUENCE: 24

Ala Ser Asn Glu Asn Met Glu Thr Met
1               5

<210> SEQ ID NO 25
<211> LENGTH: 9
<212> TYPE: PRT
<213> ORGANISM: Influenza Virus

<400> SEQUENCE: 25

Ala Ser Asn Glu Asn Met Asp Ala Met
1               5

<210> SEQ ID NO 26
<211> LENGTH: 10
<212> TYPE: PRT
<213> ORGANISM: Influenza Virus

<400> SEQUENCE: 26

Lys Leu Gly Glu Phe Tyr Asn Gln Met Met
1               5                   10

<210> SEQ ID NO 27
<211> LENGTH: 9
<212> TYPE: PRT
<213> ORGANISM: Influenza Virus

<400> SEQUENCE: 27

Leu Tyr Gln Asn Val Gly Thr Tyr Val
1               5

<210> SEQ ID NO 28
<211> LENGTH: 10
<212> TYPE: PRT
<213> ORGANISM: Influenza Virus

<400> SEQUENCE: 28

Thr Tyr Val Ser Val Gly Thr Ser Thr Leu
1               5                   10

<210> SEQ ID NO 29
<211> LENGTH: 8
<212> TYPE: PRT
<213> ORGANISM: Influenza Virus

<400> SEQUENCE: 29

Phe Glu Ser Thr Gly Asn Leu Ile
1               5
```

-continued

<210> SEQ ID NO 30
<211> LENGTH: 9
<212> TYPE: PRT
<213> ORGANISM: Influenza Virus

<400> SEQUENCE: 30

Val Tyr Gln Ile Leu Ala Ile Tyr Ala
1               5

<210> SEQ ID NO 31
<211> LENGTH: 9
<212> TYPE: PRT
<213> ORGANISM: Influenza Virus

<400> SEQUENCE: 31

Ile Tyr Ala Thr Val Ala Gly Ser Leu
1               5

<210> SEQ ID NO 32
<211> LENGTH: 9
<212> TYPE: PRT
<213> ORGANISM: Influenza Virus

<400> SEQUENCE: 32

Gly Ile Leu Gly Phe Val Phe Thr Leu
1               5

<210> SEQ ID NO 33
<211> LENGTH: 10
<212> TYPE: PRT
<213> ORGANISM: Influenza Virus

<400> SEQUENCE: 33

Ile Leu Gly Phe Val Phe Thr Leu Thr Val
1               5                   10

<210> SEQ ID NO 34
<211> LENGTH: 9
<212> TYPE: PRT
<213> ORGANISM: Influenza Virus

<400> SEQUENCE: 34

Ile Leu Arg Gly Ser Val Ala His Lys
1               5

<210> SEQ ID NO 35
<211> LENGTH: 9
<212> TYPE: PRT
<213> ORGANISM: Influenza Virus

<400> SEQUENCE: 35

Glu Asp Leu Arg Val Leu Ser Phe Ile
1               5

<210> SEQ ID NO 36
<211> LENGTH: 9
<212> TYPE: PRT
<213> ORGANISM: Influenza Virus

<400> SEQUENCE: 36

Glu Leu Arg Ser Arg Tyr Trp Ala Ile
1               5

<210> SEQ ID NO 37

```
<211> LENGTH: 9
<212> TYPE: PRT
<213> ORGANISM: Influenza Virus

<400> SEQUENCE: 37

Ser Arg Tyr Trp Ala Ile Arg Thr Arg
 1               5

<210> SEQ ID NO 38
<211> LENGTH: 9
<212> TYPE: PRT
<213> ORGANISM: Influenza Virus

<400> SEQUENCE: 38

Lys Thr Gly Gly Pro Ile Tyr Lys Arg
 1               5

<210> SEQ ID NO 39
<211> LENGTH: 9
<212> TYPE: PRT
<213> ORGANISM: Sendai Virus

<400> SEQUENCE: 39

Phe Ala Pro Gly Asn Tyr Pro Ala Leu
 1               5

<210> SEQ ID NO 40
<211> LENGTH: 9
<212> TYPE: PRT
<213> ORGANISM: Measles Virus

<400> SEQUENCE: 40

Arg Arg Tyr Pro Asp Ala Val Tyr Leu
 1               5

<210> SEQ ID NO 41
<211> LENGTH: 9
<212> TYPE: PRT
<213> ORGANISM: Measles Virus

<400> SEQUENCE: 41

Asp Pro Val Ile Asp Arg Leu Tyr Leu
 1               5

<210> SEQ ID NO 42
<211> LENGTH: 9
<212> TYPE: PRT
<213> ORGANISM: Measles Virus

<400> SEQUENCE: 42

Ser Pro Gly Arg Ser Phe Ser Tyr Phe
 1               5

<210> SEQ ID NO 43
<211> LENGTH: 9
<212> TYPE: PRT
<213> ORGANISM: Measles Virus

<400> SEQUENCE: 43

Tyr Pro Ala Leu Gly Leu His Glu Phe
 1               5

<210> SEQ ID NO 44
<211> LENGTH: 8
<212> TYPE: PRT
```

-continued

<213> ORGANISM: Polio Virus

<400> SEQUENCE: 44

Thr Tyr Lys Asp Thr Val Gln Leu
1 5

<210> SEQ ID NO 45
<211> LENGTH: 10
<212> TYPE: PRT
<213> ORGANISM: Polio Virus

<400> SEQUENCE: 45

Phe Tyr Asp Gly Phe Ser Lys Val Pro Leu
1 5 10

<210> SEQ ID NO 46
<211> LENGTH: 11
<212> TYPE: PRT
<213> ORGANISM: Human Cytomegalovirus (HCMV)

<400> SEQUENCE: 46

Phe Ile Ala Gly Asn Ser Ala Tyr Glu Tyr Val
1 5 10

<210> SEQ ID NO 47
<211> LENGTH: 9
<212> TYPE: PRT
<213> ORGANISM: Mouse Cytomegalovirus (MCMV)

<400> SEQUENCE: 47

Tyr Pro His Phe Met Pro Thr Asn Leu
1 5

<210> SEQ ID NO 48
<211> LENGTH: 9
<212> TYPE: PRT
<213> ORGANISM: Coronavirus

<400> SEQUENCE: 48

Ala Pro Thr Ala Gly Ala Phe Phe Phe
1 5

<210> SEQ ID NO 49
<211> LENGTH: 11
<212> TYPE: PRT
<213> ORGANISM: Hepatitis B Virus

<400> SEQUENCE: 49

Ser Thr Leu Pro Glu Thr Thr Val Val Arg Arg
1 5 10

<210> SEQ ID NO 50
<211> LENGTH: 10
<212> TYPE: PRT
<213> ORGANISM: Hepatitis B Virus

<400> SEQUENCE: 50

Phe Leu Pro Ser Asp Phe Phe Pro Ser Val
1 5 10

<210> SEQ ID NO 51
<211> LENGTH: 9
<212> TYPE: PRT
<213> ORGANISM: Hepatitis B Virus

```
<400> SEQUENCE: 51

Trp Leu Ser Leu Val Pro Phe Val
1               5

<210> SEQ ID NO 52
<211> LENGTH: 10
<212> TYPE: PRT
<213> ORGANISM: Hepatitis B Virus

<400> SEQUENCE: 52

Gly Leu Ser Pro Thr Val Trp Leu Ser Val
1               5                   10

<210> SEQ ID NO 53
<211> LENGTH: 9
<212> TYPE: PRT
<213> ORGANISM: Hepatitis C Virus

<400> SEQUENCE: 53

Asp Leu Met Gly Tyr Ile Pro Leu Val
1               5

<210> SEQ ID NO 54
<211> LENGTH: 10
<212> TYPE: PRT
<213> ORGANISM: Hepatitis C Virus

<400> SEQUENCE: 54

Leu Met Gly Tyr Ile Pro Leu Val Gly Ala
1               5                   10

<210> SEQ ID NO 55
<211> LENGTH: 8
<212> TYPE: PRT
<213> ORGANISM: Hepatitis C Virus

<400> SEQUENCE: 55

Ala Ser Arg Cys Trp Val Ala Met
1               5

<210> SEQ ID NO 56
<211> LENGTH: 10
<212> TYPE: PRT
<213> ORGANISM: Hepatitis C Virus

<400> SEQUENCE: 56

Lys Leu Val Ala Leu Gly Ile Asn Ala Val
1               5                   10

<210> SEQ ID NO 57
<211> LENGTH: 9
<212> TYPE: PRT
<213> ORGANISM: Epstein Barr Virus

<400> SEQUENCE: 57

Phe Leu Arg Gly Arg Ala Tyr Gly Leu
1               5

<210> SEQ ID NO 58
<211> LENGTH: 9
<212> TYPE: PRT
<213> ORGANISM: Epstein Barr Virus

<400> SEQUENCE: 58
```

Arg Arg Ile Tyr Asp Leu Ile Glu Leu
1               5

<210> SEQ ID NO 59
<211> LENGTH: 9
<212> TYPE: PRT
<213> ORGANISM: Epstein Barr Virus

<400> SEQUENCE: 59

Ile Val Thr Asp Phe Ser Val Ile Lys
1               5

<210> SEQ ID NO 60
<211> LENGTH: 9
<212> TYPE: PRT
<213> ORGANISM: Epstein Barr Virus

<400> SEQUENCE: 60

Arg Arg Arg Trp Arg Arg Leu Thr Val
1               5

<210> SEQ ID NO 61
<211> LENGTH: 10
<212> TYPE: PRT
<213> ORGANISM: Epstein Barr Virus

<400> SEQUENCE: 61

Glu Glu Asn Leu Leu Asp Phe Val Arg Phe
1               5                   10

<210> SEQ ID NO 62
<211> LENGTH: 9
<212> TYPE: PRT
<213> ORGANISM: Epstein Barr Virus

<400> SEQUENCE: 62

Cys Leu Gly Gly Leu Leu Thr Met Val
1               5

<210> SEQ ID NO 63
<211> LENGTH: 8
<212> TYPE: PRT
<213> ORGANISM: Herpes Simplex Virus

<400> SEQUENCE: 63

Ser Ser Ile Glu Phe Ala Arg Leu
1               5

<210> SEQ ID NO 64
<211> LENGTH: 11
<212> TYPE: PRT
<213> ORGANISM: Herpes Simplex Virus

<400> SEQUENCE: 64

Leu Tyr Arg Thr Phe Ala Gly Asn Pro Arg Ala
1               5                   10

<210> SEQ ID NO 65
<211> LENGTH: 9
<212> TYPE: PRT
<213> ORGANISM: Herpes Simplex Virus

<400> SEQUENCE: 65

Asp Tyr Ala Thr Leu Gly Val Gly Val
1               5

<210> SEQ ID NO 66
<211> LENGTH: 9
<212> TYPE: PRT
<213> ORGANISM: Human Papilloma Virus

<400> SEQUENCE: 66

Leu Leu Leu Gly Thr Leu Asn Ile Val
 1               5

<210> SEQ ID NO 67
<211> LENGTH: 9
<212> TYPE: PRT
<213> ORGANISM: Human Papilloma Virus

<400> SEQUENCE: 67

Leu Leu Met Gly Thr Leu Gly Ile Val
 1               5

<210> SEQ ID NO 68
<211> LENGTH: 9
<212> TYPE: PRT
<213> ORGANISM: Human Papilloma Virus

<400> SEQUENCE: 68

Thr Leu Gln Asp Ile Val Leu His Leu
 1               5

<210> SEQ ID NO 69
<211> LENGTH: 9
<212> TYPE: PRT
<213> ORGANISM: Human Papilloma Virus

<400> SEQUENCE: 69

Gly Leu His Cys Tyr Glu Gln Leu Val
 1               5

<210> SEQ ID NO 70
<211> LENGTH: 9
<212> TYPE: PRT
<213> ORGANISM: Human Papilloma Virus

<400> SEQUENCE: 70

Pro Leu Lys Gln His Phe Gln Ile Val
 1               5

<210> SEQ ID NO 71
<211> LENGTH: 9
<212> TYPE: PRT
<213> ORGANISM: Human Papilloma Virus

<400> SEQUENCE: 71

Arg Leu Val Thr Leu Lys Asp Ile Val
 1               5

<210> SEQ ID NO 72
<211> LENGTH: 9
<212> TYPE: PRT
<213> ORGANISM: Human Papilloma Virus

<400> SEQUENCE: 72

Arg Ala His Tyr Asn Ile Val Thr Phe
 1               5

-continued

```
<210> SEQ ID NO 73
<211> LENGTH: 9
<212> TYPE: PRT
<213> ORGANISM: Human T-cell Leukemia Virus

<400> SEQUENCE: 73

Leu Leu Phe Gly Tyr Pro Val Tyr Val
1               5

<210> SEQ ID NO 74
<211> LENGTH: 10
<212> TYPE: PRT
<213> ORGANISM: Simian Virus 40

<400> SEQUENCE: 74

Ser Ala Ile Asn Asn Tyr Ala Gln Lys Leu
1               5                   10

<210> SEQ ID NO 75
<211> LENGTH: 9
<212> TYPE: PRT
<213> ORGANISM: Human Immunodeficiency Virus

<400> SEQUENCE: 75

His Gln Ala Ile Ser Pro Arg Thr Leu
1               5

<210> SEQ ID NO 76
<211> LENGTH: 12
<212> TYPE: PRT
<213> ORGANISM: Human Immunodeficiency Virus

<400> SEQUENCE: 76

Gln Met Val His Gln Ala Ile Ser Pro Arg Thr Leu
1               5                   10

<210> SEQ ID NO 77
<211> LENGTH: 9
<212> TYPE: PRT
<213> ORGANISM: Simian Virus 40

<400> SEQUENCE: 77

Cys Lys Gly Val Asn Lys Glu Tyr Leu
1               5

<210> SEQ ID NO 78
<211> LENGTH: 9
<212> TYPE: PRT
<213> ORGANISM: Simian Virus 40

<400> SEQUENCE: 78

Gln Gly Ile Asn Asn Leu Asp Asn Leu
1               5

<210> SEQ ID NO 79
<211> LENGTH: 9
<212> TYPE: PRT
<213> ORGANISM: Simian Virus 40

<400> SEQUENCE: 79

Asn Asn Leu Asp Asn Leu Arg Asp Tyr
1               5

<210> SEQ ID NO 80
<211> LENGTH: 9
```

```
<212> TYPE: PRT
<213> ORGANISM: Simian Virus 40

<400> SEQUENCE: 80

Ser Glu Phe Leu Leu Glu Lys Arg Ile
1               5

<210> SEQ ID NO 81
<211> LENGTH: 9
<212> TYPE: PRT
<213> ORGANISM: Raspiratory Syncytial Virus

<400> SEQUENCE: 81

Ser Tyr Ile Gly Ser Ile Asn Asn Ile
1               5

<210> SEQ ID NO 82
<211> LENGTH: 10
<212> TYPE: PRT
<213> ORGANISM: Human Immunodeficiency Virus

<400> SEQUENCE: 82

Ile Leu Gly Asn Lys Ile Val Arg Met Tyr
1               5                   10

<210> SEQ ID NO 83
<211> LENGTH: 9
<212> TYPE: PRT
<213> ORGANISM: Human Immunodeficiency Virus

<400> SEQUENCE: 83

Arg Leu Arg Pro Gly Gly Lys Lys Lys
1               5

<210> SEQ ID NO 84
<211> LENGTH: 9
<212> TYPE: PRT
<213> ORGANISM: Human Immunodeficiency Virus

<400> SEQUENCE: 84

Glu Ile Lys Asp Thr Lys Glu Ala Leu
1               5

<210> SEQ ID NO 85
<211> LENGTH: 9
<212> TYPE: PRT
<213> ORGANISM: Human Immunodeficiency Virus

<400> SEQUENCE: 85

Gly Glu Ile Tyr Lys Arg Trp Ile Ile
1               5

<210> SEQ ID NO 86
<211> LENGTH: 9
<212> TYPE: PRT
<213> ORGANISM: Human Immunodeficiency Virus

<400> SEQUENCE: 86

Glu Ile Tyr Lys Arg Trp Ile Ile Leu
1               5

<210> SEQ ID NO 87
<211> LENGTH: 9
<212> TYPE: PRT
<213> ORGANISM: Human Immunodeficiency Virus
```

```
<400> SEQUENCE: 87

Arg Tyr Leu Lys Asp Gln Gln Leu Leu
1               5

<210> SEQ ID NO 88
<211> LENGTH: 10
<212> TYPE: PRT
<213> ORGANISM: Human Immunodeficiency Virus

<400> SEQUENCE: 88

Arg Gly Pro Gly Arg Ala Phe Val Thr Ile
1               5                   10

<210> SEQ ID NO 89
<211> LENGTH: 9
<212> TYPE: PRT
<213> ORGANISM: Human Immunodeficiency Virus

<400> SEQUENCE: 89

Ile Val Gly Leu Asn Lys Ile Val Arg
1               5

<210> SEQ ID NO 90
<211> LENGTH: 10
<212> TYPE: PRT
<213> ORGANISM: Human Immunodeficiency Virus

<400> SEQUENCE: 90

Thr Val Tyr Tyr Gly Val Pro Val Trp Lys
1               5                   10

<210> SEQ ID NO 91
<211> LENGTH: 11
<212> TYPE: PRT
<213> ORGANISM: Human Immunodeficiency Virus

<400> SEQUENCE: 91

Arg Leu Arg Asp Leu Leu Leu Ile Val Thr Arg
1               5                   10

<210> SEQ ID NO 92
<211> LENGTH: 10
<212> TYPE: PRT
<213> ORGANISM: Human Immunodeficiency Virus

<400> SEQUENCE: 92

Lys Arg Trp Ile Ile Leu Gly Leu Asn Lys
1               5                   10

<210> SEQ ID NO 93
<211> LENGTH: 9
<212> TYPE: PRT
<213> ORGANISM: Human Immunodeficiency Virus

<400> SEQUENCE: 93

Ser Phe Asn Cys Gly Gly Glu Phe Phe
1               5

<210> SEQ ID NO 94
<211> LENGTH: 9
<212> TYPE: PRT
<213> ORGANISM: Human Immunodeficiency Virus

<400> SEQUENCE: 94
```

```
Gly Arg Ala Phe Val Thr Ile Gly Lys
 1               5
```

<210> SEQ ID NO 95
<211> LENGTH: 10
<212> TYPE: PRT
<213> ORGANISM: Human Immunodeficiency Virus

<400> SEQUENCE: 95

```
Thr Pro Gly Pro Gly Val Arg Tyr Pro Leu
 1               5                  10
```

<210> SEQ ID NO 96
<211> LENGTH: 10
<212> TYPE: PRT
<213> ORGANISM: Human Immunodeficiency Virus

<400> SEQUENCE: 96

```
Gln Val Pro Leu Arg Pro Met Thr Tyr Lys
 1               5                  10
```

<210> SEQ ID NO 97
<211> LENGTH: 9
<212> TYPE: PRT
<213> ORGANISM: Human Immunodeficiency Virus

<400> SEQUENCE: 97

```
Thr Glu Met Glu Lys Glu Gly Lys Ile
 1               5
```

<210> SEQ ID NO 98
<211> LENGTH: 9
<212> TYPE: PRT
<213> ORGANISM: Human Immunodeficiency Virus

<400> SEQUENCE: 98

```
Ile Leu Lys Glu Pro Val His Gly Val
 1               5
```

<210> SEQ ID NO 99
<211> LENGTH: 9
<212> TYPE: PRT
<213> ORGANISM: Rabies Virus

<400> SEQUENCE: 99

```
Val Glu Ala Glu Ile Ala His Gln Ile
 1               5
```

<210> SEQ ID NO 100
<211> LENGTH: 8
<212> TYPE: PRT
<213> ORGANISM: Vesicular Stomatitis Virus

<400> SEQUENCE: 100

```
Arg Gly Tyr Val Tyr Gln Gly Leu
 1               5
```

<210> SEQ ID NO 101
<211> LENGTH: 9
<212> TYPE: PRT
<213> ORGANISM: Rotavirus

<400> SEQUENCE: 101

Tyr Ser Gly Tyr Ile Phe Arg Asp Leu

<210> SEQ ID NO 102
<211> LENGTH: 9
<212> TYPE: PRT
<213> ORGANISM: Rotavirus

<400> SEQUENCE: 102

Val Gly Pro Val Phe Pro Pro Gly Met
1               5

<210> SEQ ID NO 103
<211> LENGTH: 8
<212> TYPE: PRT
<213> ORGANISM: Rotavirus

<400> SEQUENCE: 103

Ile Ile Tyr Arg Phe Leu Leu Ile
1               5

<210> SEQ ID NO 104
<211> LENGTH: 9
<212> TYPE: PRT
<213> ORGANISM: Listeria innocua

<400> SEQUENCE: 104

Lys Tyr Gly Val Ser Val Gln Asp Ile
1               5

<210> SEQ ID NO 105
<211> LENGTH: 9
<212> TYPE: PRT
<213> ORGANISM: Yersinia pseudotuberculosis

<400> SEQUENCE: 105

Ile Gln Val Gly Asn Thr Arg Thr Ile
1               5

<210> SEQ ID NO 106
<211> LENGTH: 9
<212> TYPE: PRT
<213> ORGANISM: E.coli

<400> SEQUENCE: 106

Thr Pro His Pro Ala Arg Ile Gly Leu
1               5

<210> SEQ ID NO 107
<211> LENGTH: 9
<212> TYPE: PRT
<213> ORGANISM: P. falciparum

<400> SEQUENCE: 107

Ser Tyr Ile Pro Ser Ala Glu Lys Ile
1               5

<210> SEQ ID NO 108
<211> LENGTH: 8
<212> TYPE: PRT
<213> ORGANISM: P. falciparum

<400> SEQUENCE: 108

Lys Pro Lys Asp Glu Leu Asp Tyr
1               5

```
<210> SEQ ID NO 109
<211> LENGTH: 8
<212> TYPE: PRT
<213> ORGANISM: P. falciparum

<400> SEQUENCE: 109

Lys Ser Lys Asp Glu Leu Asp Tyr
 1               5

<210> SEQ ID NO 110
<211> LENGTH: 8
<212> TYPE: PRT
<213> ORGANISM: P. falciparum

<400> SEQUENCE: 110

Lys Pro Asn Asp Lys Ser Leu Tyr
 1               5

<210> SEQ ID NO 111
<211> LENGTH: 10
<212> TYPE: PRT
<213> ORGANISM: P. falciparum

<400> SEQUENCE: 111

Lys Tyr Leu Lys Lys Ile Lys Asn Ser Leu
 1               5                  10

<210> SEQ ID NO 112
<211> LENGTH: 9
<212> TYPE: PRT
<213> ORGANISM: P. falciparum

<400> SEQUENCE: 112

Tyr Glu Asn Asp Ile Glu Lys Lys Ile
 1               5

<210> SEQ ID NO 113
<211> LENGTH: 9
<212> TYPE: PRT
<213> ORGANISM: P. falciparum

<400> SEQUENCE: 113

Asn Tyr Asp Asn Ala Gly Thr Asn Leu
 1               5

<210> SEQ ID NO 114
<211> LENGTH: 9
<212> TYPE: PRT
<213> ORGANISM: P. falciparum

<400> SEQUENCE: 114

Asp Glu Leu Asp Tyr Glu Asn Asp Ile
 1               5

<210> SEQ ID NO 115
<211> LENGTH: 9
<212> TYPE: PRT
<213> ORGANISM: P. yoelii

<400> SEQUENCE: 115

Ser Tyr Val Pro Ser Ala Glu Gln Ile
 1               5

<210> SEQ ID NO 116
```

```
<211> LENGTH: 8
<212> TYPE: PRT
<213> ORGANISM: Homo sapiens

<400> SEQUENCE: 116

Phe Glu Gln Asn Thr Ala Gln Pro
 1               5

<210> SEQ ID NO 117
<211> LENGTH: 8
<212> TYPE: PRT
<213> ORGANISM: Homo sapiens

<400> SEQUENCE: 117

Phe Glu Gln Asn Thr Ala Gln Ala
 1               5

<210> SEQ ID NO 118
<211> LENGTH: 9
<212> TYPE: PRT
<213> ORGANISM: Homo sapiens

<400> SEQUENCE: 118

Glu Ala Asp Pro Thr Gly His Ser Tyr
 1               5

<210> SEQ ID NO 119
<211> LENGTH: 9
<212> TYPE: PRT
<213> ORGANISM: Homo sapiens

<400> SEQUENCE: 119

Glu Val Asp Pro Ile Gly His Leu Tyr
 1               5

<210> SEQ ID NO 120
<211> LENGTH: 9
<212> TYPE: PRT
<213> ORGANISM: Homo sapiens

<400> SEQUENCE: 120

Ala Ala Gly Ile Gly Ile Leu Thr Val
 1               5

<210> SEQ ID NO 121
<211> LENGTH: 9
<212> TYPE: PRT
<213> ORGANISM: Homo sapiens

<400> SEQUENCE: 121

Tyr Leu Glu Pro Gly Pro Val Thr Ala
 1               5

<210> SEQ ID NO 122
<211> LENGTH: 10
<212> TYPE: PRT
<213> ORGANISM: Homo sapiens

<400> SEQUENCE: 122

Ile Leu Asp Gly Thr Ala Thr Leu Arg Leu
 1               5                  10

<210> SEQ ID NO 123
<211> LENGTH: 9
<212> TYPE: PRT
```

<213> ORGANISM: Homo sapiens

<400> SEQUENCE: 123

Met Leu Leu Ala Leu Leu Tyr Cys Leu
1               5

<210> SEQ ID NO 124
<211> LENGTH: 9
<212> TYPE: PRT
<213> ORGANISM: Homo sapiens

<400> SEQUENCE: 124

Tyr Met Asn Gly Thr Met Ser Gln Val
1               5

<210> SEQ ID NO 125
<211> LENGTH: 9
<212> TYPE: PRT
<213> ORGANISM: Homo sapiens

<400> SEQUENCE: 125

Leu Pro Tyr Leu Gly Trp Leu Val Phe
1               5

<210> SEQ ID NO 126
<211> LENGTH: 9
<212> TYPE: PRT
<213> ORGANISM: Homo sapiens

<400> SEQUENCE: 126

Phe Gly Pro Tyr Lys Leu Asn Arg Leu
1               5

<210> SEQ ID NO 127
<211> LENGTH: 8
<212> TYPE: PRT
<213> ORGANISM: Homo sapiens

<400> SEQUENCE: 127

Lys Ser Pro Trp Phe Thr Thr Leu
1               5

<210> SEQ ID NO 128
<211> LENGTH: 10
<212> TYPE: PRT
<213> ORGANISM: Homo sapiens

<400> SEQUENCE: 128

Gly Pro Pro His Ser Asn Asn Phe Gly Tyr
1               5                   10

<210> SEQ ID NO 129
<211> LENGTH: 9
<212> TYPE: PRT
<213> ORGANISM: Homo sapiens

<400> SEQUENCE: 129

Ile Ser Thr Gln Asn His Arg Ala Leu
1               5

<210> SEQ ID NO 130
<211> LENGTH: 10
<212> TYPE: PRT
<213> ORGANISM: Infleuenza Virus -continued

```
<400> SEQUENCE: 130

Tyr Gly Ile Leu Gly Lys Val Phe Thr Leu
 1               5                  10

<210> SEQ ID NO 131
<211> LENGTH: 9
<212> TYPE: PRT
<213> ORGANISM: Human Immunodeficiency Virus

<400> SEQUENCE: 131

Ser Leu Tyr Asn Thr Val Ala Thr Leu
 1               5

<210> SEQ ID NO 132
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 132

Leu Phe Trp Pro Phe Glu Trp Ile
 1               5

<210> SEQ ID NO 133
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 133

Asp Gly Val Gly Ser Phe Ile Gly
 1               5

<210> SEQ ID NO 134
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 134

Glu Ser Leu Trp Asn Pro Gln Cys
 1               5

<210> SEQ ID NO 135
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 135

Leu His Phe Asp Val Leu Trp Arg
 1               5

<210> SEQ ID NO 136
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 136

Cys His Leu Lys Met Val Pro Trp
```

<210> SEQ ID NO 137
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 137

Asn Ser Val Leu Val Cys Glu Leu
 1               5

<210> SEQ ID NO 138
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 138

Asp Arg Gly His Ser Thr Tyr Ser
 1               5

<210> SEQ ID NO 139
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 139

Asp Val Trp Gly Trp Val Thr Trp
 1               5

<210> SEQ ID NO 140
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 140

Ile Gln Phe Arg Val Glu Leu Phe
 1               5

<210> SEQ ID NO 141
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 141

Leu Trp Leu Glu Leu Ser Leu Ser
 1               5

<210> SEQ ID NO 142
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 142

Val Gly Ile Cys Ala Leu Phe Gly
 1               5

```
<210> SEQ ID NO 143
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 143

Pro Tyr Pro Ser Gly Leu Asp Ser
1               5

<210> SEQ ID NO 144
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 144

Phe Trp Gly Val Leu Pro Tyr Pro
1               5

<210> SEQ ID NO 145
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 145

Phe Thr His Gly Ile Ser Leu Tyr
1               5

<210> SEQ ID NO 146
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 146

Asn His Ser Phe Gly Gly Ser Thr
1               5

<210> SEQ ID NO 147
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 147

Val Asp Tyr Val Tyr Phe His His
1               5

<210> SEQ ID NO 148
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 148

Phe Leu Asp Ile Ile Gly Tyr Gly
1               5
```

```
<210> SEQ ID NO 149
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 149

Trp Asp Asp Leu Leu His Gly Arg
 1               5

<210> SEQ ID NO 150
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 150

Leu Arg Leu Leu Gly Thr Leu Asn
 1               5

<210> SEQ ID NO 151
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 151

Phe Glu Gln His Asn Gln Glu Pro
 1               5

<210> SEQ ID NO 152
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 152

Phe Val Gly Thr Val Thr Trp Ser
 1               5

<210> SEQ ID NO 153
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 153

Leu Trp Ala Leu Thr Tyr Arg Gly
 1               5

<210> SEQ ID NO 154
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 154

Ser Trp Gly Ser Asn Gly Gly Phe
 1               5
```

```
<210> SEQ ID NO 155
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 155

Asp Met Trp Arg Arg Ala Val Gln
 1               5

<210> SEQ ID NO 156
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 156

Cys Arg Val Ile Tyr His Ala Thr
 1               5

<210> SEQ ID NO 157
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 157

Met Val Val Ala Arg Cys Gly His
 1               5

<210> SEQ ID NO 158
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 158

His Met Trp Ile Asn Trp Val Gln
 1               5

<210> SEQ ID NO 159
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 159

Cys Ala Gly Arg Cys Phe Gly Tyr
 1               5

<210> SEQ ID NO 160
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 160

Cys Thr His Val Leu Ala Tyr Ser
 1               5

<210> SEQ ID NO 161
```

```
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 161

Ser Trp Met Pro Trp Leu Thr Met
1               5

<210> SEQ ID NO 162
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 162

Leu Glu Trp Cys Ile Trp Arg Tyr
1               5

<210> SEQ ID NO 163
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 163

Cys Leu Ala Cys Ile Ile His Ser
1               5

<210> SEQ ID NO 164
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 164

Phe Trp Phe Pro Trp Asp Arg Ser
1               5

<210> SEQ ID NO 165
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 165

Trp Arg Thr Gly Val Phe His Gly
1               5

<210> SEQ ID NO 166
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 166

Met His Leu Arg Val Ala Asp Arg
1               5

<210> SEQ ID NO 167
<211> LENGTH: 8
```

```
<212> TYPE: PRT
<213> ORGANISM: Artificial Sequence
<220> FEATURE:
<223> OTHER INFORMATION: Heat shock protein binding domain

<400> SEQUENCE: 167

Ala Leu Asp Leu Tyr Leu Tyr Val
 1               5

<210> SEQ ID NO 168
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 168

Phe Phe Trp Phe Thr Leu Lys Glu
 1               5

<210> SEQ ID NO 169
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 169

Leu Ser Phe Ala Gly Trp Gly Val
 1               5

<210> SEQ ID NO 170
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 170

Met Met Met Leu Gly Arg Ala Pro
 1               5

<210> SEQ ID NO 171
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 171

Trp Ser Phe Tyr Thr Trp Leu Asn
 1               5

<210> SEQ ID NO 172
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 172

Phe Val Trp Met Arg Trp Ile Asp
 1               5

<210> SEQ ID NO 173
<211> LENGTH: 8
<212> TYPE: PRT
```

```
<213> ORGANISM: Artificial Sequence
<220> FEATURE:
<223> OTHER INFORMATION: Heat shock protein binding domain

<400> SEQUENCE: 173

Met Gln Val Asn Thr Pro Asp Asn
 1               5

<210> SEQ ID NO 174
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 174

Phe Trp Gly Trp Leu Ile Pro Trp
 1               5

<210> SEQ ID NO 175
<211> LENGTH: 7
<212> TYPE: PRT
<213> ORGANISM: Artificial Sequence
<220> FEATURE:
<223> OTHER INFORMATION: Heat shock protein binding domain

<400> SEQUENCE: 175

Trp Gly Trp Val Trp Trp Asp
 1               5

<210> SEQ ID NO 176
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 176

Trp Ile Phe Pro Trp Ile Gln Leu
 1               5

<210> SEQ ID NO 177
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 177

Trp Met Phe Asn Trp Pro Trp Tyr
 1               5

<210> SEQ ID NO 178
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 178

Met Asn Met Ile Val Leu Asp Lys
 1               5

<210> SEQ ID NO 179
<211> LENGTH: 8
<212> TYPE: PRT
<213> ORGANISM: Artificial Sequence
```

```
<220> FEATURE:
<223> OTHER INFORMATION: Heat shock protein binding domain

<400> SEQUENCE: 179

Phe Trp Gly Trp Pro Gly Trp Ser
1               5

<210> SEQ ID NO 180
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 180

Trp Leu Ile Arg Val Gly Thr Ala
1               5

<210> SEQ ID NO 181
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 181

Gly Leu Leu Thr His Leu Ile Trp
1               5

<210> SEQ ID NO 182
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 182

Leu Trp Trp Leu Asn Val His Gly
1               5

<210> SEQ ID NO 183
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 183

Trp Trp Trp Ile Asn Asp Glu Ser
1               5

<210> SEQ ID NO 184
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 184

Ala Asn Pro Ser Leu Ala Thr Tyr
1               5

<210> SEQ ID NO 185
<211> LENGTH: 8
<212> TYPE: PRT
<213> ORGANISM: Artificial Sequence
<220> FEATURE:
```

-continued

<223> OTHER INFORMATION: Heat shock protein binding domain

<400> SEQUENCE: 185

Trp Leu Gln Gly Trp Trp Gly Trp
1               5

<210> SEQ ID NO 186
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 186

Met Met Pro Val Thr Ser Phe Arg
1               5

<210> SEQ ID NO 187
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 187

Gly Trp Met Asp Trp Trp Tyr Tyr
1               5

<210> SEQ ID NO 188
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 188

Leu Ala Ser Met Arg Asn Ser Met
1               5

<210> SEQ ID NO 189
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 189

Asp Leu Met Arg Trp Leu Gly Leu
1               5

<210> SEQ ID NO 190
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 190

Tyr Phe Tyr Ala Trp Trp Leu Asp
1               5

<210> SEQ ID NO 191
<211> LENGTH: 8
<212> TYPE: PRT
<213> ORGANISM: Artificial Sequence
<220> FEATURE:
<223> OTHER INFORMATION: Heat shock protein binding domain

```
<400> SEQUENCE: 191

Leu Gly His Leu Trp Thr Gln Val
1               5

<210> SEQ ID NO 192
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 192

Leu Trp Trp Arg Asp Val Met Ala
1               5

<210> SEQ ID NO 193
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 193

Phe Ile Trp Trp Ala Pro Leu Ala
1               5

<210> SEQ ID NO 194
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 194

Gly Ser Val Gly Gly Gly Val Val
1               5

<210> SEQ ID NO 195
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 195

Asp Ser His Asp Asp Trp Arg Met
1               5

<210> SEQ ID NO 196
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 196

Phe Trp Arg Phe Asp Tyr Tyr Phe
1               5

<210> SEQ ID NO 197
<211> LENGTH: 8
<212> TYPE: PRT
<213> ORGANISM: Artificial Sequence
<220> FEATURE:
<223> OTHER INFORMATION: Heat shock protein binding domain
```

```
<400> SEQUENCE: 197

Trp Thr Trp Trp Glu Trp Leu Ala
 1               5

<210> SEQ ID NO 198
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 198

Trp Leu Trp Asp Trp Ile Val Val
 1               5

<210> SEQ ID NO 199
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 199

Gly Trp Thr Trp Phe Phe Asp Met
 1               5

<210> SEQ ID NO 200
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 200

Ala Trp Trp Gln His Phe Ile Val
 1               5

<210> SEQ ID NO 201
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 201

Leu Trp Trp Asp Ile Ile Thr Gly
 1               5

<210> SEQ ID NO 202
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 202

Phe Thr Tyr Gly Ser Arg Trp Leu
 1               5

<210> SEQ ID NO 203
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 203
```

```
Phe Ser Leu Trp Pro Leu Ala Trp
 1               5

<210> SEQ ID NO 204
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 204

Gly Ile Ile Leu Gly Tyr Asn Val
 1               5

<210> SEQ ID NO 205
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 205

Ser Trp Met Thr Trp Ile Glu His
 1               5

<210> SEQ ID NO 206
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 206

Gly Trp Trp Val Thr Trp Pro Trp
 1               5

<210> SEQ ID NO 207
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 207

Val Val Ser Pro Trp Trp Leu Gly
 1               5

<210> SEQ ID NO 208
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 208

Asn Val Leu Ser Arg Gly Phe Ser
 1               5

<210> SEQ ID NO 209
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 209
```

-continued

Ser Phe Glu Ser Leu Gly Gly Leu
1               5

<210> SEQ ID NO 210
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 210

Ile Thr Lys Gly Ser Ser Phe Pro
1               5

<210> SEQ ID NO 211
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 211

Leu Asp Trp Ala Arg Lys Leu Arg
1               5

<210> SEQ ID NO 212
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 212

Thr Ala Trp Asn Leu Leu Gly Tyr
1               5

<210> SEQ ID NO 213
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 213

Phe Gly Gln Gly Ile Lys His Val
1               5

<210> SEQ ID NO 214
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 214

Asp Val Val Trp Gln Arg Leu Leu
1               5

<210> SEQ ID NO 215
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 215

Tyr Val Asp Arg Phe Ile Gly Trp

```
<210> SEQ ID NO 216
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 216

Lys Met Ala Arg Pro Glu Gly Asn
1               5

<210> SEQ ID NO 217
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 217

Leu Gly Arg Trp Gly His Glu Ser
1               5

<210> SEQ ID NO 218
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 218

Ser Ile Trp Ser Leu Leu Val Leu
1               5

<210> SEQ ID NO 219
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 219

Val Trp Leu Asp Leu Leu Leu Ser
1               5

<210> SEQ ID NO 220
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 220

Tyr Leu Thr Asp Ser Leu Phe Gly
1               5

<210> SEQ ID NO 221
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 221

Thr Trp Trp Pro Ser Ile Thr Trp
1               5
```

```
<210> SEQ ID NO 222
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 222

Tyr Gly Leu Trp Trp Phe Pro Trp
 1               5

<210> SEQ ID NO 223
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 223

Phe Ser Pro Ala Asp Thr Arg Tyr
 1               5

<210> SEQ ID NO 224
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 224

Cys Asn Arg Leu Gln Ile Asp Cys
 1               5

<210> SEQ ID NO 225
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 225

Ser Leu Val Ala Ala Arg Asn Leu
 1               5

<210> SEQ ID NO 226
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 226

Phe Thr Ile His Asn Val Ala Val
 1               5

<210> SEQ ID NO 227
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 227

Met Gly Pro Leu Gly Pro Leu Leu
 1               5
```

```
<210> SEQ ID NO 228
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 228

Arg Gln Leu Ser Glu Leu Phe Val
 1               5

<210> SEQ ID NO 229
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 229

Arg Val Val Cys Gln Ala Leu Leu
 1               5

<210> SEQ ID NO 230
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 230

Trp Pro His Leu Trp Trp Leu Asp
 1               5

<210> SEQ ID NO 231
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 231

Trp Met Asp Trp Val Trp His Thr
 1               5

<210> SEQ ID NO 232
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 232

Trp Trp Gly Tyr Leu Ile Cys Gln
 1               5

<210> SEQ ID NO 233
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 233

Phe Arg Gly Leu Ser Glu Gly Pro
 1               5
```

```
<210> SEQ ID NO 234
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 234

Ser Trp Phe Asp Trp Leu Val Ala
 1               5

<210> SEQ ID NO 235
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 235

Val Val Met Trp Tyr Ser Val Asp
 1               5

<210> SEQ ID NO 236
<211> LENGTH: 7
<212> TYPE: PRT
<213> ORGANISM: Artificial Sequence
<220> FEATURE:
<223> OTHER INFORMATION: Heat shock protein binding domain

<400> SEQUENCE: 236

Trp Gly Trp Ser Leu Ala Thr
 1               5

<210> SEQ ID NO 237
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 237

Leu Gly Trp Phe Asp Arg Phe Phe
 1               5

<210> SEQ ID NO 238
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 238

Ala Trp Trp Trp Pro Thr Tyr Val
 1               5

<210> SEQ ID NO 239
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 239

Gly Phe Leu Ser Ser Trp Phe Leu
 1               5

<210> SEQ ID NO 240
```

```
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 240

Gly Val Ile Asn Cys Ala Gly Thr
 1               5

<210> SEQ ID NO 241
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 241

Val Cys Ala Arg Ala Ala His Leu
 1               5

<210> SEQ ID NO 242
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 242

Gly Asn Ser Tyr Gly Asp Gly Gly
 1               5

<210> SEQ ID NO 243
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 243

Gly Phe Leu Ser Ser Trp Phe Leu
 1               5

<210> SEQ ID NO 244
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 244

Phe Asp Gln Pro Gly Arg Phe Leu
 1               5

<210> SEQ ID NO 245
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 245

Arg Ser His Ala Thr Gly Val Val
 1               5

<210> SEQ ID NO 246
<211> LENGTH: 8
```

-continued

```
<212> TYPE: PRT
<213> ORGANISM: Artificial Sequence
<220> FEATURE:
<223> OTHER INFORMATION: Heat shock protein binding domain

<400> SEQUENCE: 246

Gly Tyr Trp Ala Met Met Ser Trp
 1               5

<210> SEQ ID NO 247
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 247

Cys His Ser Met Trp Asp Gly Leu
 1               5

<210> SEQ ID NO 248
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 248

Phe Ile Trp Arg Gly Trp Pro His
 1               5

<210> SEQ ID NO 249
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 249

Leu Ser Phe Leu Gly Gly Arg Leu
 1               5

<210> SEQ ID NO 250
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 250

Phe Ser Gly Val Arg Gln Pro Asn
 1               5

<210> SEQ ID NO 251
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 251

Trp Gly Trp Met Pro Phe Tyr Tyr
 1               5

<210> SEQ ID NO 252
<211> LENGTH: 8
<212> TYPE: PRT
```

<213> ORGANISM: Artificial Sequence
<220> FEATURE:
<223> OTHER INFORMATION: Heat shock protein binding domain

<400> SEQUENCE: 252

Phe Thr Arg Pro Ala Val Val Asp
1               5

<210> SEQ ID NO 253
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 253

Asp Leu Trp Thr Trp Leu Gly Leu
1               5

<210> SEQ ID NO 254
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 254

Cys Asp Thr Ala Ala Val Ala Asp
1               5

<210> SEQ ID NO 255
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 255

Trp Trp Val Lys His His Met Leu
1               5

<210> SEQ ID NO 256
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 256

Ile Ala Phe Leu Arg Asp Asn Arg
1               5

<210> SEQ ID NO 257
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 257

Leu Ala Arg Pro Asp His Tyr Ser
1               5

<210> SEQ ID NO 258
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 258

Met Glu Ser Lys Arg Trp Thr Val
1               5

<210> SEQ ID NO 259
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 259

Met Ile Leu Lys Gly Tyr Ser Arg
1               5

<210> SEQ ID NO 260
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 260

Ala Pro Ser Asp Tyr Asp Glu Ser
1               5

<210> SEQ ID NO 261
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 261

His Trp Leu Arg Ser Lys Arg Thr
1               5

<210> SEQ ID NO 262
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 262

Gly Ala Arg Val Trp Asn Tyr Gln
1               5

<210> SEQ ID NO 263
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 263

Leu Ser Asn Trp Asn Met Arg Leu
1               5

<210> SEQ ID NO 264
<211> LENGTH: 8
<212> TYPE: PRT
<213> ORGANISM: Artificial Sequence
<220> FEATURE:

```
<223> OTHER INFORMATION: Heat shock protein binding domain

<400> SEQUENCE: 264

Cys Gly Ala Ala Gln Gln Gly Met
 1               5

<210> SEQ ID NO 265
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 265

Gly Ser Ser Met Val Val Gln Arg
 1               5

<210> SEQ ID NO 266
<211> LENGTH: 4
<212> TYPE: PRT
<213> ORGANISM: Artificial Sequence
<220> FEATURE:
<223> OTHER INFORMATION: Mutated heat shock protein binding domain

<400> SEQUENCE: 266

Lys Asp Glu Leu
 1

<210> SEQ ID NO 267
<211> LENGTH: 8
<212> TYPE: PRT
<213> ORGANISM: Artificial Sequence
<220> FEATURE:
<223> OTHER INFORMATION: pentapeptide binding motif

<400> SEQUENCE: 267

His Trp Asp Phe Ala Trp Pro Trp
 1               5

<210> SEQ ID NO 268
<211> LENGTH: 8
<212> TYPE: PRT
<213> ORGANISM: Artificial Sequence
<220> FEATURE:
<223> OTHER INFORMATION: pentapeptide binding motif

<400> SEQUENCE: 268

Phe Trp Gly Leu Trp Pro Trp Glu
 1               5

<210> SEQ ID NO 269
<211> LENGTH: 14
<212> TYPE: PRT
<213> ORGANISM: Artificial Sequence
<220> FEATURE:
<223> OTHER INFORMATION: Heat shock protein binding motif

<400> SEQUENCE: 269

Lys Arg Gln Ile Tyr Asp Leu Glu Met Asn Arg Leu Gly Lys
 1               5                  10

<210> SEQ ID NO 270
<211> LENGTH: 15
<212> TYPE: PRT
<213> ORGANISM: Artificial Sequence
<220> FEATURE:
<223> OTHER INFORMATION: Heat shock protein binding motif
```

```
<400> SEQUENCE: 270

Leu Ser Ser Leu Phe Arg Pro Lys Arg Arg Pro Ile Tyr Lys Ser
 1               5                  10                  15

<210> SEQ ID NO 271
<211> LENGTH: 13
<212> TYPE: PRT
<213> ORGANISM: Artificial Sequence
<220> FEATURE:
<223> OTHER INFORMATION: Heat shock protein binding motif

<400> SEQUENCE: 271

Lys Leu Ile Gly Val Leu Ser Ser Leu Phe Arg Pro Lys
 1               5                  10

<210> SEQ ID NO 272
<211> LENGTH: 15
<212> TYPE: PRT
<213> ORGANISM: Artificial Sequence
<220> FEATURE:
<223> OTHER INFORMATION: Heat shock protein binding motif

<400> SEQUENCE: 272

Arg Arg Pro Ile Tyr Lys Ser Asp Val Gly Met Ala His Phe Arg
 1               5                  10                  15

<210> SEQ ID NO 273
<211> LENGTH: 11
<212> TYPE: PRT
<213> ORGANISM: Artificial Sequence
<220> FEATURE:
<223> OTHER INFORMATION: Heat shock protein binding motif

<400> SEQUENCE: 273

Cys Lys Ile Gln Ser Thr Pro Val Lys Gln Ser
 1               5                  10

<210> SEQ ID NO 274
<211> LENGTH: 9
<212> TYPE: PRT
<213> ORGANISM: Artificial Sequence
<220> FEATURE:
<223> OTHER INFORMATION: Heat shock protein binding motif

<400> SEQUENCE: 274

Tyr His Cys Asp Gly Phe Gln Asn Glu
 1               5

<210> SEQ ID NO 275
<211> LENGTH: 11
<212> TYPE: PRT
<213> ORGANISM: Artificial Sequence
<220> FEATURE:
<223> OTHER INFORMATION: Heat shock protein binding motif

<400> SEQUENCE: 275

Val Gly Ile Asp Leu Gly Thr Thr Tyr Ser Cys
 1               5                  10

<210> SEQ ID NO 276
<211> LENGTH: 10
<212> TYPE: PRT
<213> ORGANISM: Artificial Sequence
<220> FEATURE:
<223> OTHER INFORMATION: Heat shock protein binding motif
```

```
<400> SEQUENCE: 276

Ser Asn Gly Ser Leu Gln Cys Arg Ile Cys
1               5                   10

<210> SEQ ID NO 277
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 277

Gly Lys Trp Val Tyr Ile
1               5

<210> SEQ ID NO 278
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 278

Ala Lys Arg Glu Thr Lys
1               5

<210> SEQ ID NO 279
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 279

Lys Trp Val His Leu Phe
1               5

<210> SEQ ID NO 280
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 280

Arg Leu Val Leu Val Leu
1               5

<210> SEQ ID NO 281
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 281

Trp Lys Trp Gly Ile Tyr
1               5

<210> SEQ ID NO 282
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 282
```

Ser Ser His Ala Ser Ala
1               5

<210> SEQ ID NO 283
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 283

Trp Gly Pro Trp Ser Phe
1               5

<210> SEQ ID NO 284
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 284

Ala Ile Pro Gly Lys Val
1               5

<210> SEQ ID NO 285
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 285

Arg Val His Asp Pro Ala
1               5

<210> SEQ ID NO 286
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 286

Arg Ser Val Ser Ser Phe
1               5

<210> SEQ ID NO 287
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 287

Leu Gly Thr Arg Lys Gly
1               5

<210> SEQ ID NO 288
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 288

Lys Asp Pro Leu Phe Asn
1               5

<210> SEQ ID NO 289
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 289

Leu Ser Gln His Thr Asn
1               5

<210> SEQ ID NO 290
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 290

Asn Arg Leu Leu Leu Thr
1               5

<210> SEQ ID NO 291
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 291

Tyr Pro Leu Trp Val Ile
1               5

<210> SEQ ID NO 292
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 292

Leu Leu Ile Ile Asp Arg
1               5

<210> SEQ ID NO 293
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 293

Arg Val Ile Ser Leu Gln
1               5

<210> SEQ ID NO 294
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 294

Glu Val Ser Arg Glu Asp

```
1               5

<210> SEQ ID NO 295
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 295

Ser Ile Leu Arg Ser Thr
1               5

<210> SEQ ID NO 296
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 296

Pro Gly Leu Val Trp Leu
1               5

<210> SEQ ID NO 297
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 297

Val Lys Lys Leu Tyr Ile
1               5

<210> SEQ ID NO 298
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 298

Asn Asn Arg Leu Leu Asp
1               5

<210> SEQ ID NO 299
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 299

Ser Lys Gly Arg Trp Gly
1               5

<210> SEQ ID NO 300
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 300

Ile Arg Pro Ser Gly Ile
1               5
```

<210> SEQ ID NO 301
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 301

Ala Ser Leu Cys Pro Thr
1               5

<210> SEQ ID NO 302
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 302

Asp Val Pro Gly Leu Arg
1               5

<210> SEQ ID NO 303
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 303

Arg His Arg Glu Val Gln
1               5

<210> SEQ ID NO 304
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 304

Leu Ala Arg Lys Arg Ser
1               5

<210> SEQ ID NO 305
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 305

Ser Val Leu Asp His Val
1               5

<210> SEQ ID NO 306
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 306

Asn Leu Leu Arg Arg Ala
1               5

```
<210> SEQ ID NO 307
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 307

Ser Gly Ile Ser Ala Trp
 1               5

<210> SEQ ID NO 308
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 308

Phe Tyr Phe Trp Val Arg
 1               5

<210> SEQ ID NO 309
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 309

Lys Leu Phe Leu Pro Leu
 1               5

<210> SEQ ID NO 310
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 310

Thr Pro Thr Leu Ser Asp
 1               5

<210> SEQ ID NO 311
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 311

Thr His Ser Leu Ile Leu
 1               5

<210> SEQ ID NO 312
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 312

Leu Leu Leu Leu Ser Arg
 1               5
```

```
<210> SEQ ID NO 313
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 313

Leu Leu Arg Val Arg Ser
 1               5

<210> SEQ ID NO 314
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 314

Glu Arg Arg Ser Arg Gly
 1               5

<210> SEQ ID NO 315
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 315

Arg Met Leu Gln Leu Ala
 1               5

<210> SEQ ID NO 316
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 316

Arg Gly Trp Ala Asn Ser
 1               5

<210> SEQ ID NO 317
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 317

Arg Pro Phe Tyr Ser Tyr
 1               5

<210> SEQ ID NO 318
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 318

Ser Ser Ser Trp Asn Ala
 1               5

<210> SEQ ID NO 319
```

```
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 319

Leu Gly His Leu Glu Glu
 1               5

<210> SEQ ID NO 320
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 320

Ser Ala Val Thr Asn Thr
 1               5

<210> SEQ ID NO 321
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 321

Leu Arg Arg Ala Ser Leu
 1               5

<210> SEQ ID NO 322
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 322

Leu Arg Arg Trp Ser Leu
 1               5

<210> SEQ ID NO 323
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 323

Lys Trp Val His Leu Phe
 1               5

<210> SEQ ID NO 324
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 324

Asn Arg Leu Leu Leu Thr
 1               5

<210> SEQ ID NO 325
<211> LENGTH: 6
```

```
<212> TYPE: PRT
<213> ORGANISM: Artificial Sequence
<220> FEATURE:
<223> OTHER INFORMATION: Heat shock protein binding motif

<400> SEQUENCE: 325

Ala Arg Leu Leu Leu Thr
 1               5

<210> SEQ ID NO 326
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 326

Asn Ala Leu Leu Leu Thr
 1               5

<210> SEQ ID NO 327
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 327

Asn Arg Leu Ala Leu Thr
 1               5

<210> SEQ ID NO 328
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 328

Asn Leu Leu Arg Leu Thr
 1               5

<210> SEQ ID NO 329
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 329

Asn Arg Leu Trp Leu Thr
 1               5

<210> SEQ ID NO 330
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 330

Asn Arg Leu Leu Leu Ala
 1               5

<210> SEQ ID NO 331
<211> LENGTH: 12
<212> TYPE: PRT
```

```
<213> ORGANISM: Artificial Sequence
<220> FEATURE:
<223> OTHER INFORMATION: Heat shock protein binding motif

<400> SEQUENCE: 331

Met Gln Glu Arg Ile Thr Leu Lys Asp Tyr Ala Met
1               5                   10

<210> SEQ ID NO 332
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 332

Leu Arg Arg Trp Ser Leu Gly
1               5

<210> SEQ ID NO 333
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 333

Lys Trp Val His Leu Phe Gly
1               5

<210> SEQ ID NO 334
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 334

Asn Arg Leu Leu Leu Thr Gly
1               5

<210> SEQ ID NO 335
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 335

Ala Arg Leu Leu Leu Thr Gly
1               5

<210> SEQ ID NO 336
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 336

Asn Ala Leu Leu Leu Thr Gly
1               5

<210> SEQ ID NO 337
<211> LENGTH: 7
<212> TYPE: PRT
<213> ORGANISM: Artificial Sequence
```

```
<220> FEATURE:
<223> OTHER INFORMATION: Heat shock protein binding motif

<400> SEQUENCE: 337

Asn Arg Leu Ala Leu Thr Gly
 1               5

<210> SEQ ID NO 338
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 338

Asn Leu Leu Arg Leu Thr Gly
 1               5

<210> SEQ ID NO 339
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 339

Asn Arg Leu Trp Leu Thr Gly
 1               5

<210> SEQ ID NO 340
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 340

Asn Arg Leu Leu Leu Ala Gly
 1               5

<210> SEQ ID NO 341
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 341

Gly Lys Trp Val Tyr Ile Gly
 1               5

<210> SEQ ID NO 342
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 342

Ala Lys Arg Glu Thr Lys Gly
 1               5

<210> SEQ ID NO 343
<211> LENGTH: 7
<212> TYPE: PRT
<213> ORGANISM: Artificial Sequence
<220> FEATURE:
```

```
<223> OTHER INFORMATION: Heat shock protein binding motif

<400> SEQUENCE: 343

Lys Trp Val His Leu Phe Gly
 1               5

<210> SEQ ID NO 344
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 344

Arg Leu Val Leu Val Leu Gly
 1               5

<210> SEQ ID NO 345
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 345

Trp Lys Trp Gly Ile Tyr
 1               5

<210> SEQ ID NO 346
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 346

Ser Ser His Ala Ser Ala
 1               5

<210> SEQ ID NO 347
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 347

Trp Gly Pro Trp Ser Phe
 1               5

<210> SEQ ID NO 348
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 348

Ala Ile Pro Gly Lys Val
 1               5

<210> SEQ ID NO 349
<211> LENGTH: 7
<212> TYPE: PRT
<213> ORGANISM: Artificial Sequence
<220> FEATURE:
<223> OTHER INFORMATION: Heat shock protein binding motif
```

```
<400> SEQUENCE: 349

Arg Val His Asp Pro Ala Gly
 1               5

<210> SEQ ID NO 350
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 350

Arg Ser Val Ser Ser Phe Gly
 1               5

<210> SEQ ID NO 351
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 351

Leu Gly Thr Arg Lys Gly Gly
 1               5

<210> SEQ ID NO 352
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 352

Lys Asp Pro Leu Phe Asn Gly
 1               5

<210> SEQ ID NO 353
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 353

Leu Ser Gln His Thr Asn Gly
 1               5

<210> SEQ ID NO 354
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 354

Asn Arg Leu Leu Leu Thr Gly
 1               5

<210> SEQ ID NO 355
<211> LENGTH: 7
<212> TYPE: PRT
<213> ORGANISM: Artificial Sequence
<220> FEATURE:
<223> OTHER INFORMATION: Heat shock protein binding motif
```

```
<400> SEQUENCE: 355

Tyr Pro Leu Trp Val Ile Gly
1               5

<210> SEQ ID NO 356
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 356

Leu Leu Ile Ile Asp Arg Gly
1               5

<210> SEQ ID NO 357
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 357

Arg Val Ile Ser Leu Gln Gly
1               5

<210> SEQ ID NO 358
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 358

Glu Val Ser Arg Glu Asp Gly
1               5

<210> SEQ ID NO 359
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 359

Ser Ile Leu Arg Ser Thr Gly
1               5

<210> SEQ ID NO 360
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 360

Pro Gly Leu Val Trp Leu Gly
1               5

<210> SEQ ID NO 361
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 361
```

```
Val Lys Lys Leu Tyr Ile Gly
1               5
```

<210> SEQ ID NO 362
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 362

```
Asn Asn Arg Leu Leu Asp Gly
1               5
```

<210> SEQ ID NO 363
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 363

```
Ser Lys Gly Arg Trp Gly Gly
1               5
```

<210> SEQ ID NO 364
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 364

```
Ile Arg Pro Ser Gly Ile Gly
1               5
```

<210> SEQ ID NO 365
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 365

```
Ala Ser Leu Cys Pro Thr Gly
1               5
```

<210> SEQ ID NO 366
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 366

```
Asp Val Pro Gly Leu Arg Gly
1               5
```

<210> SEQ ID NO 367
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 367

Arg His Arg Glu Val Gln Gly
1               5

<210> SEQ ID NO 368
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 368

Leu Ala Arg Lys Arg Ser Gly
1               5

<210> SEQ ID NO 369
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 369

Ser Val Leu Asp His Val Gly
1               5

<210> SEQ ID NO 370
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 370

Asn Leu Leu Arg Arg Ala Gly
1               5

<210> SEQ ID NO 371
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 371

Ser Gly Ile Ser Ala Trp Gly
1               5

<210> SEQ ID NO 372
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 372

Phe Tyr Phe Trp Val Arg Gly
1               5

<210> SEQ ID NO 373
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 373

Lys Leu Phe Leu Pro Leu Gly

<210> SEQ ID NO 374
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 374

Thr Pro Thr Leu Ser Asp Gly
 1               5

<210> SEQ ID NO 375
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 375

Thr His Ser Leu Ile Leu Gly
 1               5

<210> SEQ ID NO 376
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 376

Leu Leu Leu Leu Ser Arg Gly
 1               5

<210> SEQ ID NO 377
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 377

Leu Leu Arg Val Arg Ser Gly
 1               5

<210> SEQ ID NO 378
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 378

Glu Arg Arg Ser Arg Gly Gly
 1               5

<210> SEQ ID NO 379
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 379

Arg Met Leu Gln Leu Ala Gly
 1               5

```
<210> SEQ ID NO 380
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 380

Arg Gly Trp Ala Asn Ser Gly
 1               5

<210> SEQ ID NO 381
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 381

Arg Pro Phe Tyr Ser Tyr Gly
 1               5

<210> SEQ ID NO 382
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 382

Ser Ser Ser Trp Asn Ala Gly
 1               5

<210> SEQ ID NO 383
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 383

Leu Gly His Leu Glu Glu Gly
 1               5

<210> SEQ ID NO 384
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 384

Ser Ala Val Thr Asn Thr Gly
 1               5

<210> SEQ ID NO 385
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 385

Phe Tyr Gln Leu Ala Leu Thr
 1               5
```

```
<210> SEQ ID NO 386
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 386

Phe Tyr Gln Leu Ala Leu Thr Trp
 1               5

<210> SEQ ID NO 387
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 387

Arg Lys Leu Phe Phe Asn Leu Arg
 1               5

<210> SEQ ID NO 388
<211> LENGTH: 9
<212> TYPE: PRT
<213> ORGANISM: Artificial Sequence
<220> FEATURE:
<223> OTHER INFORMATION: Heat shock protein binding motif

<400> SEQUENCE: 388

Arg Lys Leu Phe Phe Asn Leu Arg Trp
 1               5

<210> SEQ ID NO 389
<211> LENGTH: 5
<212> TYPE: PRT
<213> ORGANISM: Artificial Sequence
<220> FEATURE:
<223> OTHER INFORMATION: Heat shock protein binding motif

<400> SEQUENCE: 389

Lys Phe Glu Arg Gln
 1               5

<210> SEQ ID NO 390
<211> LENGTH: 6
<212> TYPE: PRT
<213> ORGANISM: Artificial Sequence
<220> FEATURE:
<223> OTHER INFORMATION: Heat shock protein binding motif

<400> SEQUENCE: 390

Ile Val Arg Lys Lys Lys
 1               5

<210> SEQ ID NO 391
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 391

Arg Gly Tyr Val Tyr Gln Gly Leu
 1               5
```

```
<210> SEQ ID NO 392
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 392

His Thr Thr Val Tyr Gly Ala Gly
 1               5

<210> SEQ ID NO 393
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 393

Thr Glu Thr Pro Tyr Pro Thr Gly
 1               5

<210> SEQ ID NO 394
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 394

Leu Thr Thr Pro Phe Ser Ser Gly
 1               5

<210> SEQ ID NO 395
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 395

Gly Val Pro Leu Thr Met Asp Gly
 1               5

<210> SEQ ID NO 396
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 396

Lys Leu Pro Thr Val Leu Arg Gly
 1               5

<210> SEQ ID NO 397
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 397

Cys Arg Phe His Gly Asn Arg Gly
 1               5

<210> SEQ ID NO 398
```

```
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 398

Tyr Thr Arg Asp Phe Glu Ala Gly
 1               5

<210> SEQ ID NO 399
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 399

Ser Ser Ala Ala Gly Pro Arg Gly
 1               5

<210> SEQ ID NO 400
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 400

Ser Leu Ile Gln Tyr Ser Arg Gly
 1               5

<210> SEQ ID NO 401
<211> LENGTH: 8
<212> TYPE: PRT
<213> ORGANISM: Artificial Sequence
<220> FEATURE:
<223> OTHER INFORMATION: Heat shock protein binding motif
<220> FEATURE:
<221> NAME/KEY: VARIANT
<222> LOCATION: 7
<223> OTHER INFORMATION: Xaa = Any Amino Acid

<400> SEQUENCE: 401

Asp Ala Leu Met Trp Pro Xaa Gly
 1               5

<210> SEQ ID NO 402
<211> LENGTH: 8
<212> TYPE: PRT
<213> ORGANISM: Artificial Sequence
<220> FEATURE:
<223> OTHER INFORMATION: Heat shock protein binding motif
<220> FEATURE:
<221> NAME/KEY: VARIANT
<222> LOCATION: 3
<223> OTHER INFORMATION: Xaa = Any Amino Acid

<400> SEQUENCE: 402

Ser Ser Xaa Ser Leu Tyr Ile Gly
 1               5

<210> SEQ ID NO 403
<211> LENGTH: 8
<212> TYPE: PRT
<213> ORGANISM: Artificial Sequence
<220> FEATURE:
<223> OTHER INFORMATION: Heat shock protein binding motif
```

```
<400> SEQUENCE: 403

Phe Asn Thr Ser Thr Arg Thr Gly
 1               5

<210> SEQ ID NO 404
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 404

Thr Val Gln His Val Ala Phe Gly
 1               5

<210> SEQ ID NO 405
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 405

Asp Tyr Ser Phe Pro Pro Leu Gly
 1               5

<210> SEQ ID NO 406
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 406

Val Gly Ser Met Glu Ser Leu Gly
 1               5

<210> SEQ ID NO 407
<211> LENGTH: 8
<212> TYPE: PRT
<213> ORGANISM: Artificial Sequence
<220> FEATURE:
<223> OTHER INFORMATION: Heat shock protein binding motif
<220> FEATURE:
<221> NAME/KEY: VARIANT
<222> LOCATION: 2, 6
<223> OTHER INFORMATION: Xaa = Any Amino Acid

<400> SEQUENCE: 407

Phe Xaa Pro Met Ile Xaa Ser Gly
 1               5

<210> SEQ ID NO 408
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 408

Ala Pro Pro Arg Val Thr Met Gly
 1               5

<210> SEQ ID NO 409
<211> LENGTH: 8
<212> TYPE: PRT
<213> ORGANISM: Artificial Sequence
```

```
<220> FEATURE:
<223> OTHER INFORMATION: Heat shock protein binding motif

<400> SEQUENCE: 409

Ile Ala Thr Lys Thr Pro Lys Gly
 1               5

<210> SEQ ID NO 410
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 410

Lys Pro Pro Leu Phe Gln Ile Gly
 1               5

<210> SEQ ID NO 411
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 411

Tyr His Thr Ala His Asn Met Gly
 1               5

<210> SEQ ID NO 412
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 412

Ser Tyr Ile Gln Ala Thr His Gly
 1               5

<210> SEQ ID NO 413
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 413

Ser Ser Phe Ala Thr Phe Leu Gly
 1               5

<210> SEQ ID NO 414
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 414

Thr Thr Pro Pro Asn Phe Ala Gly
 1               5

<210> SEQ ID NO 415
<211> LENGTH: 8
<212> TYPE: PRT
<213> ORGANISM: Artificial Sequence
<220> FEATURE:
```

<223> OTHER INFORMATION: Heat shock protein binding motif

<400> SEQUENCE: 415

Ile Ser Leu Asp Pro Arg Met Gly
1               5

<210> SEQ ID NO 416
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 416

Ser Leu Pro Leu Phe Gly Ala Gly
1               5

<210> SEQ ID NO 417
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 417

Asn Leu Leu Lys Thr Thr Leu Gly
1               5

<210> SEQ ID NO 418
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 418

Asp Gln Asn Leu Pro Arg Arg Gly
1               5

<210> SEQ ID NO 419
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 419

Ser His Phe Glu Gln Leu Leu Gly
1               5

<210> SEQ ID NO 420
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 420

Thr Pro Gln Leu His His Gly Gly
1               5

<210> SEQ ID NO 421
<211> LENGTH: 8
<212> TYPE: PRT
<213> ORGANISM: Artificial Sequence
<220> FEATURE:
<223> OTHER INFORMATION: Heat shock protein binding motif

```
<400> SEQUENCE: 421

Ala Pro Leu Asp Arg Ile Thr Gly
 1               5

<210> SEQ ID NO 422
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 422

Phe Ala Pro Leu Ile Ala His Gly
 1               5

<210> SEQ ID NO 423
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 423

Ser Trp Ile Gln Thr Phe Met Gly
 1               5

<210> SEQ ID NO 424
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 424

Asn Thr Trp Pro His Met Tyr Gly
 1               5

<210> SEQ ID NO 425
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 425

Glu Pro Leu Pro Thr Thr Leu Gly
 1               5

<210> SEQ ID NO 426
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 426

His Gly Pro His Leu Phe Asn Gly
 1               5

<210> SEQ ID NO 427
<211> LENGTH: 8
<212> TYPE: PRT
<213> ORGANISM: Artificial Sequence
<220> FEATURE:
<223> OTHER INFORMATION: Heat shock protein binding motif
```

```
<400> SEQUENCE: 427

Tyr Leu Asn Ser Thr Leu Ala Gly
 1               5

<210> SEQ ID NO 428
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 428

His Leu His Ser Pro Ser Gly Gly
 1               5

<210> SEQ ID NO 429
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 429

Thr Leu Pro His Arg Leu Asn Gly
 1               5

<210> SEQ ID NO 430
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 430

Ser Ser Pro Arg Glu Val His Gly
 1               5

<210> SEQ ID NO 431
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 431

Asn Gln Val Asp Thr Ala Arg Gly
 1               5

<210> SEQ ID NO 432
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 432

Tyr Pro Thr Pro Leu Leu Thr Gly
 1               5

<210> SEQ ID NO 433
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 433
```

His Pro Ala Ala Phe Pro Trp Gly
1               5

<210> SEQ ID NO 434
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 434

Leu Leu Pro His Ser Ser Ala Gly
1               5

<210> SEQ ID NO 435
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 435

Leu Glu Thr Tyr Thr Ala Ser Gly
1               5

<210> SEQ ID NO 436
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 436

Lys Tyr Val Pro Leu Pro Pro Gly
1               5

<210> SEQ ID NO 437
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 437

Ala Pro Leu Ala Leu His Ala Gly
1               5

<210> SEQ ID NO 438
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 438

Tyr Glu Ser Leu Leu Thr Lys Gly
1               5

<210> SEQ ID NO 439
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 439

```
Ser His Ala Ala Ser Gly Thr Gly
 1               5

<210> SEQ ID NO 440
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 440

Gly Leu Ala Thr Val Lys Ser Gly
 1               5

<210> SEQ ID NO 441
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 441

Gly Ala Thr Ser Phe Gly Leu Gly
 1               5

<210> SEQ ID NO 442
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 442

Lys Pro Pro Gly Pro Val Ser Gly
 1               5

<210> SEQ ID NO 443
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 443

Thr Leu Tyr Val Ser Gly Asn Gly
 1               5

<210> SEQ ID NO 444
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 444

His Ala Pro Phe Lys Ser Gln Gly
 1               5

<210> SEQ ID NO 445
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 445

Val Ala Phe Thr Arg Leu Pro Gly
```

```
1               5

<210> SEQ ID NO 446
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 446

Leu Pro Thr Arg Thr Pro Ala Gly
1               5

<210> SEQ ID NO 447
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 447

Ala Ser Phe Asp Leu Leu Ile Gly
1               5

<210> SEQ ID NO 448
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 448

Arg Met Asn Thr Glu Pro Pro Gly
1               5

<210> SEQ ID NO 449
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 449

Lys Met Thr Pro Leu Thr Thr Gly
1               5

<210> SEQ ID NO 450
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 450

Ala Asn Ala Thr Pro Leu Leu Gly
1               5

<210> SEQ ID NO 451
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 451

Thr Ile Trp Pro Pro Pro Val Gly
1               5
```

<210> SEQ ID NO 452
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 452

Gln Thr Lys Val Met Thr Thr Gly
 1               5

<210> SEQ ID NO 453
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 453

Asn His Ala Val Phe Ala Ser Gly
 1               5

<210> SEQ ID NO 454
<211> LENGTH: 8
<212> TYPE: PRT
<213> ORGANISM: Artificial Sequence
<220> FEATURE:
<223> OTHER INFORMATION: Heat shock protein binding motif
<220> FEATURE:
<221> NAME/KEY: VARIANT
<222> LOCATION: 5
<223> OTHER INFORMATION: Xaa = Any Amino Acid

<400> SEQUENCE: 454

Leu His Ala Ala Xaa Thr Ser Gly
 1               5

<210> SEQ ID NO 455
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 455

Thr Trp Gln Pro Tyr Phe His Gly
 1               5

<210> SEQ ID NO 456
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 456

Ala Pro Leu Ala Leu His Ala Gly
 1               5

<210> SEQ ID NO 457
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 457

```
Thr Ala His Asp Leu Thr Val Gly
 1               5
```

<210> SEQ ID NO 458
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 458

```
Asn Met Thr Asn Met Leu Thr Gly
 1               5
```

<210> SEQ ID NO 459
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 459

```
Gly Ser Gly Leu Ser Gln Asp Gly
 1               5
```

<210> SEQ ID NO 460
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 460

```
Thr Pro Ile Lys Thr Ile Tyr Gly
 1               5
```

<210> SEQ ID NO 461
<211> LENGTH: 8
<212> TYPE: PRT
<213> ORGANISM: Artificial Sequence
<220> FEATURE:
<223> OTHER INFORMATION: Heat shock protein binding motif

<400> SEQUENCE: 461

```
Ser His Leu Tyr Arg Ser Ser Gly
 1               5
```

<210> SEQ ID NO 462
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 462

```
Tyr Thr Leu Val Gln Pro Leu
 1               5
```

<210> SEQ ID NO 463
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 463

```
Thr Pro Asp Ile Thr Pro Lys
1               5

<210> SEQ ID NO 464
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 464

Thr Tyr Pro Asp Leu Arg Tyr
1               5

<210> SEQ ID NO 465
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 465

Asp Arg Thr His Ala Thr Ser
1               5

<210> SEQ ID NO 466
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 466

Met Ser Thr Thr Phe Tyr Ser
1               5

<210> SEQ ID NO 467
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 467

Tyr Gln His Ala Val Gln Thr
1               5

<210> SEQ ID NO 468
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 468

Phe Pro Phe Ser Ala Ser Thr
1               5

<210> SEQ ID NO 469
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 469

Ser Ser Phe Pro Pro Leu Asp
```

-continued

<210> SEQ ID NO 470
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 470

Met Ala Pro Ser Pro Pro His
1               5

<210> SEQ ID NO 471
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 471

Ser Ser Phe Pro Asp Leu Leu
1               5

<210> SEQ ID NO 472
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 472

His Ser Tyr Asn Arg Leu Pro
1               5

<210> SEQ ID NO 473
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 473

His Leu Thr His Ser Gln Arg
1               5

<210> SEQ ID NO 474
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 474

Gln Ala Ala Gln Ser Arg Ser
1               5

<210> SEQ ID NO 475
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 475

Phe Ala Thr His His Ile Gly
1               5

<210> SEQ ID NO 476
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 476

Ser Met Pro Glu Pro Leu Ile
 1               5

<210> SEQ ID NO 477
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 477

Ile Pro Arg Tyr His Leu Ile
 1               5

<210> SEQ ID NO 478
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 478

Ser Ala Pro His Met Thr Ser
 1               5

<210> SEQ ID NO 479
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 479

Lys Ala Pro Val Trp Ala Ser
 1               5

<210> SEQ ID NO 480
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 480

Leu Pro His Trp Leu Leu Ile
 1               5

<210> SEQ ID NO 481
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 481

Ala Ser Ala Gly Tyr Gln Ile
 1               5

```
<210> SEQ ID NO 482
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 482

Val Thr Pro Lys Thr Gly Ser
 1               5

<210> SEQ ID NO 483
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 483

Glu His Pro Met Pro Val Leu
 1               5

<210> SEQ ID NO 484
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 484

Val Ser Ser Phe Val Thr Ser
 1               5

<210> SEQ ID NO 485
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 485

Ser Thr His Phe Thr Trp Pro
 1               5

<210> SEQ ID NO 486
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 486

Gly Gln Trp Trp Ser Pro Asp
 1               5

<210> SEQ ID NO 487
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 487

Gly Pro Pro His Gln Asp Ser
 1               5
```

<210> SEQ ID NO 488
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 488

Asn Thr Leu Pro Ser Thr Ile
 1               5

<210> SEQ ID NO 489
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 489

His Gln Pro Ser Arg Trp Val
 1               5

<210> SEQ ID NO 490
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 490

Tyr Gly Asn Pro Leu Gln Pro
 1               5

<210> SEQ ID NO 491
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 491

Phe His Trp Trp Trp Gln Pro
 1               5

<210> SEQ ID NO 492
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 492

Ile Thr Leu Lys Tyr Pro Leu
 1               5

<210> SEQ ID NO 493
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 493

Phe His Trp Pro Trp Leu Phe
 1               5

<210> SEQ ID NO 494

```
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 494

Thr Ala Gln Asp Ser Thr Gly
 1               5

<210> SEQ ID NO 495
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 495

Phe His Trp Trp Trp Gln Pro
 1               5

<210> SEQ ID NO 496
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 496

Phe His Trp Trp Asp Trp Trp
 1               5

<210> SEQ ID NO 497
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 497

Glu Pro Phe Phe Arg Met Gln
 1               5

<210> SEQ ID NO 498
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 498

Thr Trp Trp Leu Asn Tyr Arg
 1               5

<210> SEQ ID NO 499
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 499

Phe His Trp Trp Trp Gln Pro
 1               5

<210> SEQ ID NO 500
<211> LENGTH: 7
```

```
<212> TYPE: PRT
<213> ORGANISM: Artificial Sequence
<220> FEATURE:
<223> OTHER INFORMATION: Heat shock protein binding motif

<400> SEQUENCE: 500

Gln Pro Ser His Leu Arg Trp
 1               5

<210> SEQ ID NO 501
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 501

Ser Pro Ala Ser Pro Val Tyr
 1               5

<210> SEQ ID NO 502
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 502

Phe His Trp Trp Trp Gln Pro
 1               5

<210> SEQ ID NO 503
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 503

His Pro Ser Asn Gln Ala Ser
 1               5

<210> SEQ ID NO 504
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 504

Asn Ser Ala Pro Arg Pro Val
 1               5

<210> SEQ ID NO 505
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 505

Gln Leu Trp Ser Ile Tyr Pro
 1               5

<210> SEQ ID NO 506
<211> LENGTH: 7
<212> TYPE: PRT
```

```
<213> ORGANISM: Artificial Sequence
<220> FEATURE:
<223> OTHER INFORMATION: Heat shock protein binding motif

<400> SEQUENCE: 506

Ser Trp Pro Phe Phe Asp Leu
 1               5

<210> SEQ ID NO 507
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 507

Asp Thr Thr Leu Pro Leu His
 1               5

<210> SEQ ID NO 508
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 508

Trp His Trp Gln Met Leu Trp
 1               5

<210> SEQ ID NO 509
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 509

Asp Ser Phe Arg Thr Pro Val
 1               5

<210> SEQ ID NO 510
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 510

Thr Ser Pro Leu Ser Leu Leu
 1               5

<210> SEQ ID NO 511
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 511

Ala Tyr Asn Tyr Val Ser Asp
 1               5

<210> SEQ ID NO 512
<211> LENGTH: 7
<212> TYPE: PRT
<213> ORGANISM: Artificial Sequence
```

```
<220> FEATURE:
<223> OTHER INFORMATION: Heat shock protein binding motif

<400> SEQUENCE: 512

Arg Pro Leu His Asp Pro Met
 1               5

<210> SEQ ID NO 513
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 513

Trp Pro Ser Thr Thr Leu Phe
 1               5

<210> SEQ ID NO 514
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 514

Ala Thr Leu Glu Pro Val Arg
 1               5

<210> SEQ ID NO 515
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 515

Ser Met Thr Val Leu Arg Pro
 1               5

<210> SEQ ID NO 516
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 516

Gln Ile Gly Ala Pro Ser Trp
 1               5

<210> SEQ ID NO 517
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 517

Ala Pro Asp Leu Tyr Val Pro
 1               5

<210> SEQ ID NO 518
<211> LENGTH: 7
<212> TYPE: PRT
<213> ORGANISM: Artificial Sequence
<220> FEATURE:
```

-continued

<223> OTHER INFORMATION: Heat shock protein binding motif

<400> SEQUENCE: 518

Arg Met Pro Pro Leu Leu Pro
1               5

<210> SEQ ID NO 519
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 519

Ala Lys Ala Thr Pro Glu His
1               5

<210> SEQ ID NO 520
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 520

Thr Pro Pro Leu Arg Ile Asn
1               5

<210> SEQ ID NO 521
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 521

Leu Pro Ile His Ala Pro His
1               5

<210> SEQ ID NO 522
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 522

Asp Leu Asn Ala Tyr Thr His
1               5

<210> SEQ ID NO 523
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 523

Val Thr Leu Pro Asn Phe His
1               5

<210> SEQ ID NO 524
<211> LENGTH: 7
<212> TYPE: PRT
<213> ORGANISM: Artificial Sequence
<220> FEATURE:
<223> OTHER INFORMATION: Heat shock protein binding motif -continued

```
<400> SEQUENCE: 524

Asn Ser Arg Leu Pro Thr Leu
1               5

<210> SEQ ID NO 525
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 525

Tyr Pro His Pro Ser Arg Ser
1               5

<210> SEQ ID NO 526
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 526

Gly Thr Ala His Phe Met Tyr
1               5

<210> SEQ ID NO 527
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 527

Tyr Ser Leu Leu Pro Thr Arg
1               5

<210> SEQ ID NO 528
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 528

Leu Pro Arg Arg Thr Leu Leu
1               5

<210> SEQ ID NO 529
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 529

Thr Ser Thr Leu Leu Trp Lys
1               5

<210> SEQ ID NO 530
<211> LENGTH: 7
<212> TYPE: PRT
<213> ORGANISM: Artificial Sequence
<220> FEATURE:
<223> OTHER INFORMATION: Heat shock protein binding motif
```

```
<400> SEQUENCE: 530

Thr Ser Asp Met Lys Pro His
1               5

<210> SEQ ID NO 531
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 531

Thr Ser Ser Tyr Leu Ala Leu
1               5

<210> SEQ ID NO 532
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 532

Asn Leu Tyr Gly Pro His Asp
1               5

<210> SEQ ID NO 533
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 533

Leu Glu Thr Tyr Thr Ala Ser
1               5

<210> SEQ ID NO 534
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 534

Ala Tyr Lys Ser Leu Thr Gln
1               5

<210> SEQ ID NO 535
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 535

Ser Thr Ser Val Tyr Ser Ser
1               5

<210> SEQ ID NO 536
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 536
```

```
Glu Gly Pro Leu Arg Ser Pro
 1               5

<210> SEQ ID NO 537
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 537

Thr Thr Tyr His Ala Leu Gly
 1               5

<210> SEQ ID NO 538
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 538

Val Ser Ile Gly His Pro Ser
 1               5

<210> SEQ ID NO 539
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 539

Thr His Ser His Arg Pro Ser
 1               5

<210> SEQ ID NO 540
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 540

Ile Thr Asn Pro Leu Thr Thr
 1               5

<210> SEQ ID NO 541
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 541

Ser Ile Gln Ala His His Ser
 1               5

<210> SEQ ID NO 542
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 542
```

```
Leu Asn Trp Pro Arg Val Leu
 1               5

<210> SEQ ID NO 543
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 543

Tyr Tyr Tyr Ala Pro Pro Pro
 1               5

<210> SEQ ID NO 544
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 544

Ser Leu Trp Thr Arg Leu Pro
 1               5

<210> SEQ ID NO 545
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 545

Asn Val Tyr His Ser Ser Leu
 1               5

<210> SEQ ID NO 546
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 546

Asn Ser Pro His Pro Pro Thr
 1               5

<210> SEQ ID NO 547
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 547

Val Pro Ala Lys Pro Arg His
 1               5

<210> SEQ ID NO 548
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 548

His Asn Leu His Pro Asn Arg
```

```
1               5

<210> SEQ ID NO 549
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 549

Tyr Thr Thr His Arg Trp Leu
1               5

<210> SEQ ID NO 550
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 550

Ala Val Thr Ala Ala Ile Val
1               5

<210> SEQ ID NO 551
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 551

Thr Leu Met His Asp Arg Val
1               5

<210> SEQ ID NO 552
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 552

Thr Pro Leu Lys Val Pro Tyr
1               5

<210> SEQ ID NO 553
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 553

Phe Thr Asn Gln Gln Tyr His
1               5

<210> SEQ ID NO 554
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 554

Ser His Val Pro Ser Met Ala
1               5
```

```
<210> SEQ ID NO 555
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 555

His Thr Thr Val Tyr Gly Ala
 1               5

<210> SEQ ID NO 556
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 556

Thr Glu Thr Pro Tyr Pro Thr
 1               5

<210> SEQ ID NO 557
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 557

Leu Thr Thr Pro Phe Ser Ser
 1               5

<210> SEQ ID NO 558
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 558

Gly Val Pro Leu Thr Met Asp
 1               5

<210> SEQ ID NO 559
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 559

Lys Leu Pro Thr Val Leu Arg
 1               5

<210> SEQ ID NO 560
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 560

Cys Arg Phe His Gly Asn Arg
 1               5
```

```
<210> SEQ ID NO 561
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 561

Tyr Thr Arg Asp Phe Glu Ala
 1               5

<210> SEQ ID NO 562
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 562

Ser Ser Ala Ala Gly Pro Arg
 1               5

<210> SEQ ID NO 563
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 563

Ser Leu Ile Gln Tyr Ser Arg
 1               5

<210> SEQ ID NO 564
<211> LENGTH: 7
<212> TYPE: PRT
<213> ORGANISM: Artificial Sequence
<220> FEATURE:
<223> OTHER INFORMATION: Heat shock protein binding motif
<220> FEATURE:
<221> NAME/KEY: VARIANT
<222> LOCATION: 7
<223> OTHER INFORMATION: Xaa = Any Amino Acid

<400> SEQUENCE: 564

Asp Ala Leu Met Trp Pro Xaa
 1               5

<210> SEQ ID NO 565
<211> LENGTH: 7
<212> TYPE: PRT
<213> ORGANISM: Artificial Sequence
<220> FEATURE:
<223> OTHER INFORMATION: Heat shock protein binding motif
<220> FEATURE:
<221> NAME/KEY: VARIANT
<222> LOCATION: 3
<223> OTHER INFORMATION: Xaa = Any Amino Acid

<400> SEQUENCE: 565

Ser Ser Xaa Ser Leu Tyr Ile
 1               5

<210> SEQ ID NO 566
<211> LENGTH: 7
<212> TYPE: PRT
<213> ORGANISM: Artificial Sequence
<220> FEATURE:
```

```
<223> OTHER INFORMATION: Heat shock protein binding motif

<400> SEQUENCE: 566

Phe Asn Thr Ser Thr Arg Thr
1               5

<210> SEQ ID NO 567
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 567

Thr Val Gln His Val Ala Phe
1               5

<210> SEQ ID NO 568
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 568

Asp Tyr Ser Phe Pro Pro Leu
1               5

<210> SEQ ID NO 569
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 569

Val Gly Ser Met Glu Ser Leu
1               5

<210> SEQ ID NO 570
<211> LENGTH: 7
<212> TYPE: PRT
<213> ORGANISM: Artificial Sequence
<220> FEATURE:
<223> OTHER INFORMATION: Heat shock protein binding motif
<220> FEATURE:
<221> NAME/KEY: VARIANT
<222> LOCATION: 2, 6
<223> OTHER INFORMATION: Xaa = Any Amino Acid

<400> SEQUENCE: 570

Phe Xaa Pro Met Ile Xaa Ser
1               5

<210> SEQ ID NO 571
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 571

Ala Pro Pro Arg Val Thr Met
1               5

<210> SEQ ID NO 572
<211> LENGTH: 7
```

```
<212> TYPE: PRT
<213> ORGANISM: Artificial Sequence
<220> FEATURE:
<223> OTHER INFORMATION: Heat shock protein binding motif

<400> SEQUENCE: 572

Ile Ala Thr Lys Thr Pro Lys
1               5

<210> SEQ ID NO 573
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 573

Lys Pro Pro Leu Phe Gln Ile
1               5

<210> SEQ ID NO 574
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 574

Tyr His Thr Ala His Asn Met
1               5

<210> SEQ ID NO 575
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 575

Ser Tyr Ile Gln Ala Thr His
1               5

<210> SEQ ID NO 576
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 576

Ser Ser Phe Ala Thr Phe Leu
1               5

<210> SEQ ID NO 577
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 577

Thr Thr Pro Pro Asn Phe Ala
1               5

<210> SEQ ID NO 578
<211> LENGTH: 7
<212> TYPE: PRT
```

```
<213> ORGANISM: Artificial Sequence
<220> FEATURE:
<223> OTHER INFORMATION: Heat shock protein binding motif

<400> SEQUENCE: 578

Ile Ser Leu Asp Pro Arg Met
1               5

<210> SEQ ID NO 579
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 579

Ser Leu Pro Leu Phe Gly Ala
1               5

<210> SEQ ID NO 580
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 580

Asn Leu Leu Lys Thr Thr Leu
1               5

<210> SEQ ID NO 581
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 581

Asp Gln Asn Leu Pro Arg Arg
1               5

<210> SEQ ID NO 582
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 582

Ser His Phe Glu Gln Leu Leu
1               5

<210> SEQ ID NO 583
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 583

Thr Pro Gln Leu His His Gly
1               5

<210> SEQ ID NO 584
<211> LENGTH: 7
<212> TYPE: PRT
<213> ORGANISM: Artificial Sequence
```

```
<220> FEATURE:
<223> OTHER INFORMATION: Heat shock protein binding motif

<400> SEQUENCE: 584

Ala Pro Leu Asp Arg Ile Thr
 1               5

<210> SEQ ID NO 585
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 585

Phe Ala Pro Leu Ile Ala His
 1               5

<210> SEQ ID NO 586
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 586

Ser Trp Ile Gln Thr Phe Met
 1               5

<210> SEQ ID NO 587
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 587

Asn Thr Trp Pro His Met Tyr
 1               5

<210> SEQ ID NO 588
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 588

Glu Pro Leu Pro Thr Thr Leu
 1               5

<210> SEQ ID NO 589
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 589

His Gly Pro His Leu Phe Asn
 1               5

<210> SEQ ID NO 590
<211> LENGTH: 7
<212> TYPE: PRT
<213> ORGANISM: Artificial Sequence
<220> FEATURE:
```

<223> OTHER INFORMATION: Heat shock protein binding motif

<400> SEQUENCE: 590

Tyr Leu Asn Ser Thr Leu Ala
1               5

<210> SEQ ID NO 591
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 591

His Leu His Ser Pro Ser Gly
1               5

<210> SEQ ID NO 592
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 592

Thr Leu Pro His Arg Leu Asn
1               5

<210> SEQ ID NO 593
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 593

Ser Ser Pro Arg Glu Val His
1               5

<210> SEQ ID NO 594
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 594

Asn Gln Val Asp Thr Ala Arg
1               5

<210> SEQ ID NO 595
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 595

Tyr Pro Thr Pro Leu Leu Thr
1               5

<210> SEQ ID NO 596
<211> LENGTH: 7
<212> TYPE: PRT
<213> ORGANISM: Artificial Sequence
<220> FEATURE:
<223> OTHER INFORMATION: Heat shock protein binding motif

```
<400> SEQUENCE: 596

His Pro Ala Ala Phe Pro Trp
 1               5

<210> SEQ ID NO 597
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 597

Leu Leu Pro His Ser Ser Ala
 1               5

<210> SEQ ID NO 598
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 598

Leu Glu Thr Tyr Thr Ala Ser
 1               5

<210> SEQ ID NO 599
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 599

Lys Tyr Val Pro Leu Pro Pro
 1               5

<210> SEQ ID NO 600
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 600

Ala Pro Leu Ala Leu His Ala
 1               5

<210> SEQ ID NO 601
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 601

Tyr Glu Ser Leu Leu Thr Lys
 1               5

<210> SEQ ID NO 602
<211> LENGTH: 7
<212> TYPE: PRT
<213> ORGANISM: Artificial Sequence
<220> FEATURE:
<223> OTHER INFORMATION: Heat shock protein binding motif
```

```
<400> SEQUENCE: 602

Ser His Ala Ala Ser Gly Thr
1               5

<210> SEQ ID NO 603
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 603

Gly Leu Ala Thr Val Lys Ser
1               5

<210> SEQ ID NO 604
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 604

Gly Ala Thr Ser Phe Gly Leu
1               5

<210> SEQ ID NO 605
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 605

Lys Pro Pro Gly Pro Val Ser
1               5

<210> SEQ ID NO 606
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 606

Thr Leu Tyr Val Ser Gly Asn
1               5

<210> SEQ ID NO 607
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 607

His Ala Pro Phe Lys Ser Gln
1               5

<210> SEQ ID NO 608
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 608
```

Val Ala Phe Thr Arg Leu Pro
1               5

<210> SEQ ID NO 609
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 609

Leu Pro Thr Arg Thr Pro Ala
1               5

<210> SEQ ID NO 610
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 610

Ala Ser Phe Asp Leu Leu Ile
1               5

<210> SEQ ID NO 611
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 611

Arg Met Asn Thr Glu Pro Pro
1               5

<210> SEQ ID NO 612
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 612

Lys Met Thr Pro Leu Thr Thr
1               5

<210> SEQ ID NO 613
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 613

Ala Asn Ala Thr Pro Leu Leu
1               5

<210> SEQ ID NO 614
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 614

```
Thr Ile Trp Pro Pro Pro Val
1               5

<210> SEQ ID NO 615
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 615

Gln Thr Lys Val Met Thr Thr
1               5

<210> SEQ ID NO 616
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 616

Asn His Ala Val Phe Ala Ser
1               5

<210> SEQ ID NO 617
<211> LENGTH: 7
<212> TYPE: PRT
<213> ORGANISM: Artificial Sequence
<220> FEATURE:
<223> OTHER INFORMATION: Heat shock protein binding motif
<220> FEATURE:
<221> NAME/KEY: VARIANT
<222> LOCATION: 5
<223> OTHER INFORMATION: Xaa = Any Amino Acid

<400> SEQUENCE: 617

Leu His Ala Ala Xaa Thr Ser
1               5

<210> SEQ ID NO 618
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 618

Thr Trp Gln Pro Tyr Phe His
1               5

<210> SEQ ID NO 619
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 619

Ala Pro Leu Ala Leu His Ala
1               5

<210> SEQ ID NO 620
<211> LENGTH: 7
<212> TYPE: PRT
<213> ORGANISM: Artificial Sequence
<220> FEATURE:
<223> OTHER INFORMATION: Heat shock protein binding motif
```

```
<400> SEQUENCE: 620

Thr Ala His Asp Leu Thr Val
1               5

<210> SEQ ID NO 621
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 621

Asn Met Thr Asn Met Leu Thr
1               5

<210> SEQ ID NO 622
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 622

Gly Ser Gly Leu Ser Gln Asp
1               5

<210> SEQ ID NO 623
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 623

Thr Pro Ile Lys Thr Ile Tyr
1               5

<210> SEQ ID NO 624
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 624

Ser His Leu Tyr Arg Ser Ser
1               5

<210> SEQ ID NO 625
<211> LENGTH: 7
<212> TYPE: PRT
<213> ORGANISM: Artificial Sequence
<220> FEATURE:
<223> OTHER INFORMATION: Heat shock protein binding motif

<400> SEQUENCE: 625

His Gly Gln Ala Trp Gln Phe
1               5

<210> SEQ ID NO 626
<211> LENGTH: 5
<212> TYPE: PRT
<213> ORGANISM: Artificial Sequence
<220> FEATURE:
<223> OTHER INFORMATION: Heat shock protein binding motif
```

```
<400> SEQUENCE: 626

Phe His Trp Trp Trp
 1               5

<210> SEQ ID NO 627
<211> LENGTH: 24
<212> TYPE: PRT
<213> ORGANISM: Artificial Sequence
<220> FEATURE:
<223> OTHER INFORMATION: Heat shock protein binding motif

<400> SEQUENCE: 627

Ile Phe Ala Gly Ile Lys Lys Lys Ala Glu Arg Ala Asp Leu Ile Ala
 1               5                  10                  15

Tyr Leu Lys Gln Ala Thr Ala Lys
            20

<210> SEQ ID NO 628
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 628

Gly Lys Trp Val Tyr Ile Gly Trp
 1               5

<210> SEQ ID NO 629
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 629

Ala Lys Arg Glu Thr Lys Gly Trp
 1               5

<210> SEQ ID NO 630
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 630

Lys Trp Val His Leu Phe Gly Trp
 1               5

<210> SEQ ID NO 631
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 631

Arg Leu Val Leu Val Leu Gly Trp
 1               5

<210> SEQ ID NO 632
```

<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 632

Trp Lys Trp Gly Ile Tyr Gly Trp
 1               5

<210> SEQ ID NO 633
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 633

Ser Ser His Ala Ser Ala Gly Trp
 1               5

<210> SEQ ID NO 634
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 634

Trp Gly Pro Trp Ser Phe Gly Trp
 1               5

<210> SEQ ID NO 635
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 635

Ala Ile Pro Gly Lys Val Gly Trp
 1               5

<210> SEQ ID NO 636
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 636

Arg Val His Asp Pro Ala Gly Trp
 1               5

<210> SEQ ID NO 637
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 637

```
Arg Ser Val Ser Ser Phe Gly Trp
 1               5
```

<210> SEQ ID NO 638
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 638

```
Leu Gly Thr Arg Lys Gly Gly Trp
 1               5
```

<210> SEQ ID NO 639
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 639

```
Lys Asp Pro Leu Phe Asn Gly Trp
 1               5
```

<210> SEQ ID NO 640
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 640

```
Leu Ser Gln His Thr Asn Gly Trp
 1               5
```

<210> SEQ ID NO 641
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 641

```
Asn Arg Leu Leu Leu Thr Gly Trp
 1               5
```

<210> SEQ ID NO 642
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 642

```
Tyr Pro Leu Trp Val Ile Gly Trp
 1               5
```

<210> SEQ ID NO 643
<211> LENGTH: 8
<212> TYPE: PRT
<213> ORGANISM: Artificial Sequence
<220> FEATURE:

```
<223> OTHER INFORMATION: Heat shock protein binding domain with a
      terminal Trp residue

<400> SEQUENCE: 643

Leu Leu Ile Ile Asp Arg Gly Trp
 1               5

<210> SEQ ID NO 644
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 644

Arg Val Ile Ser Leu Gln Gly Trp
 1               5

<210> SEQ ID NO 645
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 645

Glu Val Ser Arg Glu Asp Gly Trp
 1               5

<210> SEQ ID NO 646
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 646

Ser Ile Leu Arg Ser Thr Gly Trp
 1               5

<210> SEQ ID NO 647
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 647

Pro Gly Leu Val Trp Leu Gly Trp
 1               5

<210> SEQ ID NO 648
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 648

Val Lys Lys Leu Tyr Ile Gly Trp
 1               5
```

```
<210> SEQ ID NO 649
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 649

Asn Asn Arg Leu Leu Asp Gly Trp
 1               5

<210> SEQ ID NO 650
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 650

Ser Lys Gly Arg Trp Gly Gly Trp
 1               5

<210> SEQ ID NO 651
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 651

Ile Arg Pro Ser Gly Ile Gly Trp
 1               5

<210> SEQ ID NO 652
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 652

Ala Ser Leu Cys Pro Thr Gly Trp
 1               5

<210> SEQ ID NO 653
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 653

Asp Val Pro Gly Leu Arg Gly Trp
 1               5

<210> SEQ ID NO 654
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 654
```

Arg His Arg Glu Val Gln Gly Trp
1               5

<210> SEQ ID NO 655
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 655

Leu Ala Arg Lys Arg Ser Gly Trp
1               5

<210> SEQ ID NO 656
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 656

Ser Val Leu Asp His Val Gly Trp
1               5

<210> SEQ ID NO 657
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 657

Asn Leu Leu Arg Arg Ala Gly Trp
1               5

<210> SEQ ID NO 658
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 658

Ser Gly Ile Ser Ala Trp Gly Trp
1               5

<210> SEQ ID NO 659
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 659

Phe Tyr Phe Trp Val Arg Gly Trp
1               5

<210> SEQ ID NO 660
<211> LENGTH: 8
<212> TYPE: PRT
<213> ORGANISM: Artificial Sequence

```
<220> FEATURE:
<223> OTHER INFORMATION: Heat shock protein binding domain with a
      terminal Trp residue

<400> SEQUENCE: 660

Lys Leu Phe Leu Pro Leu Gly Trp
 1               5

<210> SEQ ID NO 661
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 661

Thr Pro Thr Leu Ser Asp Gly Trp
 1               5

<210> SEQ ID NO 662
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 662

Thr His Ser Leu Ile Leu Gly Trp
 1               5

<210> SEQ ID NO 663
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 663

Leu Leu Leu Leu Ser Arg Gly Trp
 1               5

<210> SEQ ID NO 664
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 664

Leu Leu Arg Val Arg Ser Gly Trp
 1               5

<210> SEQ ID NO 665
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 665

Glu Arg Arg Ser Arg Gly Gly Trp
 1               5
```

```
<210> SEQ ID NO 666
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 666

Arg Met Leu Gln Leu Ala Gly Trp
1               5

<210> SEQ ID NO 667
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 667

Arg Gly Trp Ala Asn Ser Gly Trp
1               5

<210> SEQ ID NO 668
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 668

Arg Pro Phe Tyr Ser Tyr Gly Trp
1               5

<210> SEQ ID NO 669
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 669

Ser Ser Ser Trp Asn Ala Gly Trp
1               5

<210> SEQ ID NO 670
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 670

Leu Gly His Leu Glu Glu Gly Trp
1               5

<210> SEQ ID NO 671
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue
```

-continued

<400> SEQUENCE: 671

Ser Ala Val Thr Asn Thr Gly Trp
1               5

<210> SEQ ID NO 672
<211> LENGTH: 7
<212> TYPE: PRT
<213> ORGANISM: Artificial Sequence
<220> FEATURE:
<223> OTHER INFORMATION: Heat shock protein binding domain

<400> SEQUENCE: 672

Phe Tyr Gln Leu Ala Leu Thr
1               5

<210> SEQ ID NO 673
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 673

Phe Tyr Gln Leu Ala Leu Thr Trp
1               5

<210> SEQ ID NO 674
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 674

Arg Lys Leu Phe Phe Asn Leu Arg
1               5

<210> SEQ ID NO 675
<211> LENGTH: 9
<212> TYPE: PRT
<213> ORGANISM: Artificial Sequence
<220> FEATURE:
<223> OTHER INFORMATION: Heat shock protein binding domain

<400> SEQUENCE: 675

Arg Lys Leu Phe Phe Asn Leu Arg Trp
1               5

<210> SEQ ID NO 676
<211> LENGTH: 5
<212> TYPE: PRT
<213> ORGANISM: Artificial Sequence
<220> FEATURE:
<223> OTHER INFORMATION: Heat shock protein binding domain

<400> SEQUENCE: 676

Lys Phe Glu Arg Gln
1               5

<210> SEQ ID NO 677
<211> LENGTH: 7
<212> TYPE: PRT
<213> ORGANISM: Artificial Sequence
<220> FEATURE:
<223> OTHER INFORMATION: Heat shock protein binding domain

<400> SEQUENCE: 677

Asn Ile Val Arg Lys Lys Lys
1               5

<210> SEQ ID NO 678
<211> LENGTH: 8
<212> TYPE: PRT
<213> ORGANISM: Artificial Sequence
<220> FEATURE:
<223> OTHER INFORMATION: Heat shock protein binding domain

<400> SEQUENCE: 678

Arg Gly Tyr Val Tyr Gln Gly Leu
1               5

<210> SEQ ID NO 679
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 679

Asn Leu Leu Arg Leu Thr Gly Trp
1               5

<210> SEQ ID NO 680
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 680

Phe Tyr Gln Leu Ala Leu Tyr Trp
1               5

<210> SEQ ID NO 681
<211> LENGTH: 9
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 681

Arg Lys Leu Phe Phe Asn Leu Arg Trp
1               5

<210> SEQ ID NO 682
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 682

Leu Arg Arg Ala Ser Leu Trp
1               5

<210> SEQ ID NO 683
<211> LENGTH: 7
<212> TYPE: PRT
<213> ORGANISM: Artificial Sequence
<220> FEATURE:

```
<223> OTHER INFORMATION: Heat shock protein binding domain with a
      terminal Trp residue

<400> SEQUENCE: 683

Leu Arg Arg Trp Ser Leu Trp
 1               5

<210> SEQ ID NO 684
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 684

Lys Trp Val His Leu Phe Trp
 1               5

<210> SEQ ID NO 685
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 685

Asn Arg Leu Leu Leu Thr Trp
 1               5

<210> SEQ ID NO 686
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 686

Ala Arg Leu Leu Leu Thr Trp
 1               5

<210> SEQ ID NO 687
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 687

Asn Ala Leu Leu Leu Thr Trp
 1               5

<210> SEQ ID NO 688
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 688

Asn Arg Leu Ala Leu Thr Trp
 1               5
```

```
<210> SEQ ID NO 689
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 689

Asn Leu Leu Arg Leu Thr Trp
 1               5

<210> SEQ ID NO 690
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 690

Asn Arg Leu Trp Leu Thr Trp
 1               5

<210> SEQ ID NO 691
<211> LENGTH: 7
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 691

Asn Arg Leu Leu Leu Ala Trp
 1               5

<210> SEQ ID NO 692
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 692

Phe Tyr Gln Leu Ala Leu Thr Trp
 1               5

<210> SEQ ID NO 693
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 693

Phe Tyr Gln Leu Ala Leu Thr Trp
 1               5

<210> SEQ ID NO 694
<211> LENGTH: 9
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 694
```

Arg Lys Leu Phe Phe Asn Leu Arg Trp
1               5

<210> SEQ ID NO 695
<211> LENGTH: 9
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 695

Arg Lys Leu Phe Phe Asn Leu Arg Trp
1               5

<210> SEQ ID NO 696
<211> LENGTH: 6
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 696

Lys Phe Glu Arg Gln Trp
1               5

<210> SEQ ID NO 697
<211> LENGTH: 8
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 697

Asn Ile Val Arg Lys Lys Lys Trp
1               5

<210> SEQ ID NO 698
<211> LENGTH: 9
<212> TYPE: PRT
<213> ORGANISM: Artificial Sequence
<220> FEATURE:
<223> OTHER INFORMATION: Heat shock protein binding domain with a
      terminal Trp residue

<400> SEQUENCE: 698

Arg Gly Tyr Val Tyr Gln Gly Leu Trp
1               5

<210> SEQ ID NO 699
<211> LENGTH: 4
<212> TYPE: PRT
<213> ORGANISM: Artificial Sequence
<220> FEATURE:
<223> OTHER INFORMATION: Linker for forming hybrid antigen

<400> SEQUENCE: 699

Phe Phe Arg Lys
1

<210> SEQ ID NO 700
<211> LENGTH: 4
<212> TYPE: PRT
<213> ORGANISM: Artificial Sequence
<220> FEATURE:

```
<223> OTHER INFORMATION: Linker for forming hybrid antigen

<400> SEQUENCE: 700

Ala Lys Val Leu
 1

<210> SEQ ID NO 701
<211> LENGTH: 4
<212> TYPE: PRT
<213> ORGANISM: Artificial Sequence
<220> FEATURE:
<223> OTHER INFORMATION: Linker for forming hybrid antigen

<400> SEQUENCE: 701

Phe Arg Lys Asn
 1

<210> SEQ ID NO 702
<211> LENGTH: 5
<212> TYPE: PRT
<213> ORGANISM: Artificial Sequence
<220> FEATURE:
<223> OTHER INFORMATION: Linker for forming hybrid antigen

<400> SEQUENCE: 702

Phe Phe Arg Lys Asn
 1               5

<210> SEQ ID NO 703
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 703

Tyr Thr Leu Val Gln Pro Leu Trp
 1               5

<210> SEQ ID NO 704
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 704

Thr Pro Asp Ile Thr Pro Lys Trp
 1               5

<210> SEQ ID NO 705
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 705

Thr Tyr Pro Asp Leu Arg Tyr Trp
 1               5

<210> SEQ ID NO 706
<211> LENGTH: 8
<212> TYPE: PRT
```

```
<213> ORGANISM: Artificial Sequence
<220> FEATURE:
<223> OTHER INFORMATION: Heat shock protein binding domain with terminal
      "Trp" residue

<400> SEQUENCE: 706

Asp Arg Thr His Ala Thr Ser Trp
1               5

<210> SEQ ID NO 707
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 707

Met Ser Thr Thr Phe Tyr Ser Trp
1               5

<210> SEQ ID NO 708
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 708

Tyr Gln His Ala Val Gln Thr Trp
1               5

<210> SEQ ID NO 709
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 709

Phe Pro Phe Ser Ala Ser Thr Trp
1               5

<210> SEQ ID NO 710
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 710

Ser Ser Phe Pro Pro Leu Asp Trp
1               5

<210> SEQ ID NO 711
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 711

Met Ala Pro Ser Pro Pro His Trp
1               5
```

```
<210> SEQ ID NO 712
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 712

Ser Ser Phe Pro Asp Leu Leu Trp
1               5

<210> SEQ ID NO 713
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 713

His Ser Tyr Asn Arg Leu Pro Trp
1               5

<210> SEQ ID NO 714
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 714

His Leu Thr His Ser Gln Arg Trp
1               5

<210> SEQ ID NO 715
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 715

Gln Ala Ala Gln Ser Arg Ser Trp
1               5

<210> SEQ ID NO 716
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 716

Phe Ala Thr His His Ile Gly Trp
1               5

<210> SEQ ID NO 717
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue
```

```
<400> SEQUENCE: 717

Ser Met Pro Glu Pro Leu Ile Trp
1               5

<210> SEQ ID NO 718
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 718

Ile Pro Arg Tyr His Leu Ile Trp
1               5

<210> SEQ ID NO 719
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 719

Ser Ala Pro His Met Thr Ser Trp
1               5

<210> SEQ ID NO 720
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 720

Lys Ala Pro Val Trp Ala Ser Trp
1               5

<210> SEQ ID NO 721
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 721

Leu Pro His Trp Leu Leu Ile Trp
1               5

<210> SEQ ID NO 722
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 722

Ala Ser Ala Gly Tyr Gln Ile Trp
1               5

<210> SEQ ID NO 723
<211> LENGTH: 8
```

```
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 723

Val Thr Pro Lys Thr Gly Ser Trp
 1               5

<210> SEQ ID NO 724
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 724

Glu His Pro Met Pro Val Leu Trp
 1               5

<210> SEQ ID NO 725
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 725

Val Ser Ser Phe Val Thr Ser Trp
 1               5

<210> SEQ ID NO 726
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 726

Ser Thr His Phe Thr Trp Pro Trp
 1               5

<210> SEQ ID NO 727
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 727

Gly Gln Trp Trp Ser Pro Asp Trp
 1               5

<210> SEQ ID NO 728
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 728

Gly Pro Pro His Gln Asp Ser Trp
```

<210> SEQ ID NO 729
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 729

Asn Thr Leu Pro Ser Thr Ile Trp
1               5

<210> SEQ ID NO 730
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 730

His Gln Pro Ser Arg Trp Val Trp
1               5

<210> SEQ ID NO 731
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 731

Tyr Gly Asn Pro Leu Gln Pro Trp
1               5

<210> SEQ ID NO 732
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 732

Phe His Trp Trp Trp Gln Pro Trp
1               5

<210> SEQ ID NO 733
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 733

Ile Thr Leu Lys Tyr Pro Leu Trp
1               5

<210> SEQ ID NO 734
<211> LENGTH: 8
<212> TYPE: PRT
<213> ORGANISM: Artificial Sequence
<220> FEATURE:
<223> OTHER INFORMATION: Heat shock protein binding domain with terminal -continued "Trp" residue

<400> SEQUENCE: 734

Phe His Trp Pro Trp Leu Phe Trp
1               5

<210> SEQ ID NO 735
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 735

Thr Ala Gln Asp Ser Thr Gly Trp
1               5

<210> SEQ ID NO 736
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 736

Phe His Trp Trp Trp Gln Pro Trp
1               5

<210> SEQ ID NO 737
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 737

Phe His Trp Trp Asp Trp Trp Trp
1               5

<210> SEQ ID NO 738
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 738

Glu Pro Phe Phe Arg Met Gln Trp
1               5

<210> SEQ ID NO 739
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 739

Thr Trp Trp Leu Asn Tyr Arg Trp
1               5

<210> SEQ ID NO 740

```
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 740

Phe His Trp Trp Trp Gln Pro Trp
 1               5

<210> SEQ ID NO 741
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 741

Gln Pro Ser His Leu Arg Trp Trp
 1               5

<210> SEQ ID NO 742
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 742

Ser Pro Ala Ser Pro Val Tyr Trp
 1               5

<210> SEQ ID NO 743
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 743

Phe His Trp Trp Trp Gln Pro Trp
 1               5

<210> SEQ ID NO 744
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 744

His Pro Ser Asn Gln Ala Ser Trp
 1               5

<210> SEQ ID NO 745
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 745
```

```
Asn Ser Ala Pro Arg Pro Val Trp
 1               5

<210> SEQ ID NO 746
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 746

Gln Leu Trp Ser Ile Tyr Pro Trp
 1               5

<210> SEQ ID NO 747
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 747

Ser Trp Pro Phe Phe Asp Leu Trp
 1               5

<210> SEQ ID NO 748
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 748

Asp Thr Thr Leu Pro Leu His Trp
 1               5

<210> SEQ ID NO 749
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 749

Trp His Trp Gln Met Leu Trp Trp
 1               5

<210> SEQ ID NO 750
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 750

Asp Ser Phe Arg Thr Pro Val Trp
 1               5

<210> SEQ ID NO 751
<211> LENGTH: 8
<212> TYPE: PRT
<213> ORGANISM: Artificial Sequence
<220> FEATURE:
```

```
<223> OTHER INFORMATION: Heat shock protein binding domain with terminal
      "Trp" residue

<400> SEQUENCE: 751

Thr Ser Pro Leu Ser Leu Leu Trp
1               5

<210> SEQ ID NO 752
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 752

Ala Tyr Asn Tyr Val Ser Asp Trp
1               5

<210> SEQ ID NO 753
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 753

Arg Pro Leu His Asp Pro Met Trp
1               5

<210> SEQ ID NO 754
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 754

Trp Pro Ser Thr Thr Leu Phe Trp
1               5

<210> SEQ ID NO 755
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 755

Ala Thr Leu Glu Pro Val Arg Trp
1               5

<210> SEQ ID NO 756
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 756

Ser Met Thr Val Leu Arg Pro Trp
1               5
```

```
<210> SEQ ID NO 757
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 757

Gln Ile Gly Ala Pro Ser Trp Trp
 1               5

<210> SEQ ID NO 758
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 758

Ala Pro Asp Leu Tyr Val Pro Trp
 1               5

<210> SEQ ID NO 759
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 759

Arg Met Pro Pro Leu Leu Pro Trp
 1               5

<210> SEQ ID NO 760
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 760

Ala Lys Ala Thr Pro Glu His Trp
 1               5

<210> SEQ ID NO 761
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 761

Thr Pro Pro Leu Arg Ile Asn Trp
 1               5

<210> SEQ ID NO 762
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 762
```

```
Leu Pro Ile His Ala Pro His Trp
 1               5

<210> SEQ ID NO 763
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 763

Asp Leu Asn Ala Tyr Thr His Trp
 1               5

<210> SEQ ID NO 764
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 764

Val Thr Leu Pro Asn Phe His Trp
 1               5

<210> SEQ ID NO 765
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 765

Asn Ser Arg Leu Pro Thr Leu Trp
 1               5

<210> SEQ ID NO 766
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 766

Tyr Pro His Pro Ser Arg Ser Trp
 1               5

<210> SEQ ID NO 767
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 767

Gly Thr Ala His Phe Met Tyr Trp
 1               5

<210> SEQ ID NO 768
<211> LENGTH: 8
<212> TYPE: PRT
<213> ORGANISM: Artificial Sequence
```

```
<220> FEATURE:
<223> OTHER INFORMATION: Heat shock protein binding domain with terminal
      "Trp" residue

<400> SEQUENCE: 768

Tyr Ser Leu Leu Pro Thr Arg Trp
1               5

<210> SEQ ID NO 769
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 769

Leu Pro Arg Arg Thr Leu Leu Trp
1               5

<210> SEQ ID NO 770
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 770

Thr Ser Thr Leu Leu Trp Lys Trp
1               5

<210> SEQ ID NO 771
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 771

Thr Ser Asp Met Lys Pro His Trp
1               5

<210> SEQ ID NO 772
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 772

Thr Ser Ser Tyr Leu Ala Leu Trp
1               5

<210> SEQ ID NO 773
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 773

Asn Leu Tyr Gly Pro His Asp Trp
1               5
```

<210> SEQ ID NO 774
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 774

Leu Glu Thr Tyr Thr Ala Ser Trp
 1               5

<210> SEQ ID NO 775
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 775

Ala Tyr Lys Ser Leu Thr Gln Trp
 1               5

<210> SEQ ID NO 776
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 776

Ser Thr Ser Val Tyr Ser Ser Trp
 1               5

<210> SEQ ID NO 777
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 777

Glu Gly Pro Leu Arg Ser Pro Trp
 1               5

<210> SEQ ID NO 778
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 778

Thr Thr Tyr His Ala Leu Gly Trp
 1               5

<210> SEQ ID NO 779
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue -continued

```
<400> SEQUENCE: 779

Val Ser Ile Gly His Pro Ser Trp
1               5

<210> SEQ ID NO 780
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 780

Thr His Ser His Arg Pro Ser Trp
1               5

<210> SEQ ID NO 781
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 781

Ile Thr Asn Pro Leu Thr Thr Trp
1               5

<210> SEQ ID NO 782
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 782

Ser Ile Gln Ala His His Ser Trp
1               5

<210> SEQ ID NO 783
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 783

Leu Asn Trp Pro Arg Val Leu Trp
1               5

<210> SEQ ID NO 784
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 784

Tyr Tyr Tyr Ala Pro Pro Pro Trp
1               5

<210> SEQ ID NO 785
<211> LENGTH: 8
<212> TYPE: PRT
```

```
<213> ORGANISM: Artificial Sequence
<220> FEATURE:
<223> OTHER INFORMATION: Heat shock protein binding domain with terminal
      "Trp" residue

<400> SEQUENCE: 785

Ser Leu Trp Thr Arg Leu Pro Trp
1               5

<210> SEQ ID NO 786
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 786

Asn Val Tyr His Ser Ser Leu Trp
1               5

<210> SEQ ID NO 787
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 787

Asn Ser Pro His Pro Pro Thr Trp
1               5

<210> SEQ ID NO 788
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 788

Val Pro Ala Lys Pro Arg His Trp
1               5

<210> SEQ ID NO 789
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 789

His Asn Leu His Pro Asn Arg Trp
1               5

<210> SEQ ID NO 790
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 790

Tyr Thr Thr His Arg Trp Leu Trp
1               5
```

<210> SEQ ID NO 791
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 791

Ala Val Thr Ala Ala Ile Val Trp
1               5

<210> SEQ ID NO 792
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 792

Thr Leu Met His Asp Arg Val Trp
1               5

<210> SEQ ID NO 793
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 793

Thr Pro Leu Lys Val Pro Tyr Trp
1               5

<210> SEQ ID NO 794
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 794

Phe Thr Asn Gln Gln Tyr His Trp
1               5

<210> SEQ ID NO 795
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 795

Ser His Val Pro Ser Met Ala Trp
1               5

<210> SEQ ID NO 796
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

```
<400> SEQUENCE: 796

His Thr Thr Val Tyr Gly Ala Trp
1               5

<210> SEQ ID NO 797
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 797

Thr Glu Thr Pro Tyr Pro Thr Trp
1               5

<210> SEQ ID NO 798
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 798

Leu Thr Thr Pro Phe Ser Ser Trp
1               5

<210> SEQ ID NO 799
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 799

Gly Val Pro Leu Thr Met Asp Trp
1               5

<210> SEQ ID NO 800
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 800

Lys Leu Pro Thr Val Leu Arg Trp
1               5

<210> SEQ ID NO 801
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 801

Cys Arg Phe His Gly Asn Arg Trp
1               5

<210> SEQ ID NO 802
<211> LENGTH: 8
```

```
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 802

Tyr Thr Arg Asp Phe Glu Ala Trp
 1               5

<210> SEQ ID NO 803
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 803

Ser Ser Ala Ala Gly Pro Arg Trp
 1               5

<210> SEQ ID NO 804
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 804

Ser Leu Ile Gln Tyr Ser Arg Trp
 1               5

<210> SEQ ID NO 805
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue
<220> FEATURE:
<221> NAME/KEY: VARIANT
<222> LOCATION: 7
<223> OTHER INFORMATION: Xaa = Any Amino Acid

<400> SEQUENCE: 805

Asp Ala Leu Met Trp Pro Xaa Trp
 1               5

<210> SEQ ID NO 806
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue
<220> FEATURE:
<221> NAME/KEY: VARIANT
<222> LOCATION: 3
<223> OTHER INFORMATION: Xaa = Any Amino Acid

<400> SEQUENCE: 806

Ser Ser Xaa Ser Leu Tyr Ile Trp
 1               5

<210> SEQ ID NO 807
<211> LENGTH: 8
<212> TYPE: PRT
```

```
<213> ORGANISM: Artificial Sequence
<220> FEATURE:
<223> OTHER INFORMATION: Heat shock protein binding domain with terminal
      "Trp" residue

<400> SEQUENCE: 807

Phe Asn Thr Ser Thr Arg Thr Trp
1               5

<210> SEQ ID NO 808
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 808

Thr Val Gln His Val Ala Phe Trp
1               5

<210> SEQ ID NO 809
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 809

Asp Tyr Ser Phe Pro Pro Leu Trp
1               5

<210> SEQ ID NO 810
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 810

Val Gly Ser Met Glu Ser Leu Trp
1               5

<210> SEQ ID NO 811
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue
<220> FEATURE:
<221> NAME/KEY: VARIANT
<222> LOCATION: 2, 6
<223> OTHER INFORMATION: Xaa = Any Amino Acid

<400> SEQUENCE: 811

Phe Xaa Pro Met Ile Xaa Ser Trp
1               5

<210> SEQ ID NO 812
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue
```

-continued

```
<400> SEQUENCE: 812

Ala Pro Pro Arg Val Thr Met Trp
 1               5

<210> SEQ ID NO 813
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 813

Ile Ala Thr Lys Thr Pro Lys Trp
 1               5

<210> SEQ ID NO 814
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 814

Lys Pro Pro Leu Phe Gln Ile Trp
 1               5

<210> SEQ ID NO 815
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 815

Tyr His Thr Ala His Asn Met Trp
 1               5

<210> SEQ ID NO 816
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 816

Ser Tyr Ile Gln Ala Thr His Trp
 1               5

<210> SEQ ID NO 817
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 817

Ser Ser Phe Ala Thr Phe Leu Trp
 1               5

<210> SEQ ID NO 818
<211> LENGTH: 8
<212> TYPE: PRT
```

```
<213> ORGANISM: Artificial Sequence
<220> FEATURE:
<223> OTHER INFORMATION: Heat shock protein binding domain with terminal
      "Trp" residue

<400> SEQUENCE: 818

Thr Thr Pro Pro Asn Phe Ala Trp
1               5

<210> SEQ ID NO 819
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 819

Ile Ser Leu Asp Pro Arg Met Trp
1               5

<210> SEQ ID NO 820
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 820

Ser Leu Pro Leu Phe Gly Ala Trp
1               5

<210> SEQ ID NO 821
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 821

Asn Leu Leu Lys Thr Thr Leu Trp
1               5

<210> SEQ ID NO 822
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 822

Asp Gln Asn Leu Pro Arg Arg Trp
1               5

<210> SEQ ID NO 823
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 823

Ser His Phe Glu Gln Leu Leu Trp
1               5
```

```
<210> SEQ ID NO 824
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 824

Thr Pro Gln Leu His His Gly Trp
 1               5

<210> SEQ ID NO 825
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 825

Ala Pro Leu Asp Arg Ile Thr Trp
 1               5

<210> SEQ ID NO 826
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 826

Phe Ala Pro Leu Ile Ala His Trp
 1               5

<210> SEQ ID NO 827
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 827

Ser Trp Ile Gln Thr Phe Met Trp
 1               5

<210> SEQ ID NO 828
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 828

Asn Thr Trp Pro His Met Tyr Trp
 1               5

<210> SEQ ID NO 829
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue
```

```
<400> SEQUENCE: 829

Glu Pro Leu Pro Thr Thr Leu Trp
 1               5

<210> SEQ ID NO 830
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 830

His Gly Pro His Leu Phe Asn Trp
 1               5

<210> SEQ ID NO 831
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 831

Tyr Leu Asn Ser Thr Leu Ala Trp
 1               5

<210> SEQ ID NO 832
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 832

His Leu His Ser Pro Ser Gly Trp
 1               5

<210> SEQ ID NO 833
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 833

Thr Leu Pro His Arg Leu Asn Trp
 1               5

<210> SEQ ID NO 834
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 834

Ser Ser Pro Arg Glu Val His Trp
 1               5

<210> SEQ ID NO 835
<211> LENGTH: 8
```

```
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 835

Asn Gln Val Asp Thr Ala Arg Trp
 1               5

<210> SEQ ID NO 836
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 836

Tyr Pro Thr Pro Leu Leu Thr Trp
 1               5

<210> SEQ ID NO 837
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 837

His Pro Ala Ala Phe Pro Trp Trp
 1               5

<210> SEQ ID NO 838
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 838

Leu Leu Pro His Ser Ser Ala Trp
 1               5

<210> SEQ ID NO 839
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 839

Leu Glu Thr Tyr Thr Ala Ser Trp
 1               5

<210> SEQ ID NO 840
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 840

Lys Tyr Val Pro Leu Pro Pro Trp
```

<210> SEQ ID NO 841
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 841

Ala Pro Leu Ala Leu His Ala Trp
1               5

<210> SEQ ID NO 842
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 842

Tyr Glu Ser Leu Leu Thr Lys Trp
1               5

<210> SEQ ID NO 843
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 843

Ser His Ala Ala Ser Gly Thr Trp
1               5

<210> SEQ ID NO 844
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 844

Gly Leu Ala Thr Val Lys Ser Trp
1               5

<210> SEQ ID NO 845
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 845

Gly Ala Thr Ser Phe Gly Leu Trp
1               5

<210> SEQ ID NO 846
<211> LENGTH: 8
<212> TYPE: PRT
<213> ORGANISM: Artificial Sequence
<220> FEATURE:
<223> OTHER INFORMATION: Heat shock protein binding domain with terminal "Trp" residue

<400> SEQUENCE: 846

Lys Pro Pro Gly Pro Val Ser Trp
1               5

<210> SEQ ID NO 847
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 847

Thr Leu Tyr Val Ser Gly Asn Trp
1               5

<210> SEQ ID NO 848
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 848

His Ala Pro Phe Lys Ser Gln Trp
1               5

<210> SEQ ID NO 849
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 849

Val Ala Phe Thr Arg Leu Pro Trp
1               5

<210> SEQ ID NO 850
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 850

Leu Pro Thr Arg Thr Pro Ala Trp
1               5

<210> SEQ ID NO 851
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 851

Ala Ser Phe Asp Leu Leu Ile Trp
1               5

<210> SEQ ID NO 852

```
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 852

Arg Met Asn Thr Glu Pro Pro Trp
1               5

<210> SEQ ID NO 853
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 853

Lys Met Thr Pro Leu Thr Thr Trp
1               5

<210> SEQ ID NO 854
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 854

Ala Asn Ala Thr Pro Leu Leu Trp
1               5

<210> SEQ ID NO 855
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 855

Thr Ile Trp Pro Pro Pro Val Trp
1               5

<210> SEQ ID NO 856
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 856

Gln Thr Lys Val Met Thr Thr Trp
1               5

<210> SEQ ID NO 857
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 857
```

```
Asn His Ala Val Phe Ala Ser Trp
1               5

<210> SEQ ID NO 858
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue
<220> FEATURE:
<221> NAME/KEY: VARIANT
<222> LOCATION: 5
<223> OTHER INFORMATION: Xaa = Any Amino Acid

<400> SEQUENCE: 858

Leu His Ala Ala Xaa Thr Ser Trp
1               5

<210> SEQ ID NO 859
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 859

Thr Trp Gln Pro Tyr Phe His Trp
1               5

<210> SEQ ID NO 860
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 860

Ala Pro Leu Ala Leu His Ala Trp
1               5

<210> SEQ ID NO 861
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 861

Thr Ala His Asp Leu Thr Val Trp
1               5

<210> SEQ ID NO 862
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 862

Asn Met Thr Asn Met Leu Thr Trp
1               5

<210> SEQ ID NO 863
```

```
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 863

Gly Ser Gly Leu Ser Gln Asp Trp
1               5

<210> SEQ ID NO 864
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 864

Thr Pro Ile Lys Thr Ile Tyr Trp
1               5

<210> SEQ ID NO 865
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 865

Ser His Leu Tyr Arg Ser Ser Trp
1               5

<210> SEQ ID NO 866
<211> LENGTH: 8
<212> TYPE: PRT
<213> ORGANISM: Artificial Sequence
<220> FEATURE:
<223> OTHER INFORMATION: Heat shock protein binding domain with terminal
      "Trp" residue

<400> SEQUENCE: 866

His Gly Gln Ala Trp Gln Phe Trp
1               5

<210> SEQ ID NO 867
<211> LENGTH: 8
<212> TYPE: PRT
<213> ORGANISM: Artificial Sequence
<220> FEATURE:
<223> OTHER INFORMATION: Hybrid antigen

<400> SEQUENCE: 867

Asn Leu Leu Arg Leu Thr Gly Trp
1               5

<210> SEQ ID NO 868
<211> LENGTH: 8
<212> TYPE: PRT
<213> ORGANISM: Artificial Sequence
<220> FEATURE:
<223> OTHER INFORMATION: Hybrid antigen

<400> SEQUENCE: 868

Ser Ile Ile Asn Phe Glu Lys Leu
1               5
```

```
<210> SEQ ID NO 869
<211> LENGTH: 8
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 869

His Trp Asp Phe Ala Trp Pro Trp
 1               5

<210> SEQ ID NO 870
<211> LENGTH: 8
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 870

Asn Leu Leu Arg Leu Thr Gly Trp
 1               5

<210> SEQ ID NO 871
<211> LENGTH: 8
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 871

Phe Tyr Gln Leu Ala Leu Thr Trp
 1               5

<210> SEQ ID NO 872
<211> LENGTH: 9
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 872

Arg Lys Leu Phe Phe Asn Leu Arg Trp
 1               5

<210> SEQ ID NO 873
<211> LENGTH: 9
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 873

Ala Leu Phe Asp Ile Glu Ser Lys Val
 1               5

<210> SEQ ID NO 874
<211> LENGTH: 9
<212> TYPE: PRT
<213> ORGANISM: Artificial Sequence
<220> FEATURE:
<223> OTHER INFORMATION: Heat shock-protein binding motif to form hybrid
      antigen
```

```
<400> SEQUENCE: 874

Ile Met Asp Gln Val Pro Phe Ser Val
1               5

<210> SEQ ID NO 875
<211> LENGTH: 9
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 875

Tyr Met Asp Gly Thr Met Ser Gln Val
1               5

<210> SEQ ID NO 876
<211> LENGTH: 8
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 876

Thr Leu Gly Ile Val Cys Pro Ile
1               5

<210> SEQ ID NO 877
<211> LENGTH: 10
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 877

Tyr Met Leu Asp Leu Gln Pro Glu Thr Thr
1               5                   10

<210> SEQ ID NO 878
<211> LENGTH: 20
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 878

Ala Leu Phe Asp Ile Glu Ser Lys Val Gly Ser Gly His Trp Asp Phe
1               5                   10                  15

Ala Trp Pro Trp
            20

<210> SEQ ID NO 879
<211> LENGTH: 8
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 879

Arg Gly Tyr Val Tyr Gln Gly Leu
1               5
```

```
<210> SEQ ID NO 880
<211> LENGTH: 19
<212> TYPE: PRT
<213> ORGANISM: Artificial Sequence
<220> FEATURE:
<223> OTHER INFORMATION: Hybrid antigen

<400> SEQUENCE: 880

Asn Leu Leu Arg Leu Thr Gly Trp Gly Ser Gly Ser Ile Ile Asn Phe
 1               5                  10                  15

Glu Lys Leu

<210> SEQ ID NO 881
<211> LENGTH: 20
<212> TYPE: PRT
<213> ORGANISM: Artificial Sequence
<220> FEATURE:
<223> OTHER INFORMATION: Hybrid antigen

<400> SEQUENCE: 881

Asn Leu Leu Arg Leu Thr Gly Trp Phe Phe Arg Lys Ser Ile Ile Asn
 1               5                  10                  15

Phe Glu Lys Leu
             20

<210> SEQ ID NO 882
<211> LENGTH: 18
<212> TYPE: PRT
<213> ORGANISM: Artificial Sequence
<220> FEATURE:
<223> OTHER INFORMATION: Hybrid antigen

<400> SEQUENCE: 882

Asn Leu Leu Arg Leu Thr Gly Trp Arg Lys Ser Ile Ile Asn Phe Glu
 1               5                  10                  15

Lys Leu

<210> SEQ ID NO 883
<211> LENGTH: 19
<212> TYPE: PRT
<213> ORGANISM: Artificial Sequence
<220> FEATURE:
<223> OTHER INFORMATION: Hybrid antigen

<400> SEQUENCE: 883

Asn Leu Leu Arg Leu Thr Gly Trp Gly Ser Gly Arg Gly Tyr Val Tyr
 1               5                  10                  15

Gln Gly Leu

<210> SEQ ID NO 884
<211> LENGTH: 20
<212> TYPE: PRT
<213> ORGANISM: Artificial Sequence
<220> FEATURE:
<223> OTHER INFORMATION: Hybrid antigen

<400> SEQUENCE: 884

Asn Leu Leu Arg Leu Thr Gly Trp Phe Phe Arg Lys Arg Gly Tyr Val
 1               5                  10                  15

Tyr Gln Gly Leu
             20

<210> SEQ ID NO 885
```

```
<211> LENGTH: 18
<212> TYPE: PRT
<213> ORGANISM: Artificial Sequence
<220> FEATURE:
<223> OTHER INFORMATION: Hybrid antigen

<400> SEQUENCE: 885

Asn Leu Leu Arg Leu Thr Gly Trp Arg Lys Arg Gly Tyr Val Tyr Gln
1               5                   10                  15

Gly Leu

<210> SEQ ID NO 886
<211> LENGTH: 20
<212> TYPE: PRT
<213> ORGANISM: Artificial Sequence
<220> FEATURE:
<223> OTHER INFORMATION: Hybrid antigen

<400> SEQUENCE: 886

Asn Leu Leu Arg Leu Thr Gly Trp Ala Lys Val Leu Ser Ile Ile Asn
1               5                   10                  15

Phe Glu Lys Leu
            20

<210> SEQ ID NO 887
<211> LENGTH: 19
<212> TYPE: PRT
<213> ORGANISM: Artificial Sequence
<220> FEATURE:
<223> OTHER INFORMATION: Hybrid antigen

<400> SEQUENCE: 887

Asn Leu Leu Arg Leu Thr Gly Trp Gln Leu Lys Ser Ile Ile Asn Phe
1               5                   10                  15

Glu Lys Leu

<210> SEQ ID NO 888
<211> LENGTH: 18
<212> TYPE: PRT
<213> ORGANISM: Artificial Sequence
<220> FEATURE:
<223> OTHER INFORMATION: Hybrid antigen

<400> SEQUENCE: 888

Asn Leu Leu Arg Leu Thr Gly Trp Phe Arg Ser Ile Ile Asn Phe Glu
1               5                   10                  15

Lys Leu

<210> SEQ ID NO 889
<211> LENGTH: 21
<212> TYPE: PRT
<213> ORGANISM: Artificial Sequence
<220> FEATURE:
<223> OTHER INFORMATION: Hybrid antigen

<400> SEQUENCE: 889

Asn Leu Leu Arg Leu Thr Gly Trp Phe Phe Arg Lys Ile Met Asp Gln
1               5                   10                  15

Val Pro Phe Ser Val
            20

<210> SEQ ID NO 890
<211> LENGTH: 21
<212> TYPE: PRT
```

-continued

```
<213> ORGANISM: Artificial Sequence
<220> FEATURE:
<223> OTHER INFORMATION: Hybrid antigen

<400> SEQUENCE: 890

Asn Leu Leu Arg Leu Thr Gly Trp Phe Phe Arg Lys Tyr Met Asp Gly
 1               5                  10                  15

Thr Met Ser Gln Val
             20

<210> SEQ ID NO 891
<211> LENGTH: 9
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 891

Phe Ala Pro Gly Asn Tyr Pro Ala Leu
 1               5

<210> SEQ ID NO 892
<211> LENGTH: 21
<212> TYPE: PRT
<213> ORGANISM: Artificial Sequence
<220> FEATURE:
<223> OTHER INFORMATION: Hybrid antigen

<400> SEQUENCE: 892

Asn Leu Leu Arg Leu Thr Gly Trp Phe Phe Arg Lys Phe Ala Pro Gly
 1               5                  10                  15

Asn Tyr Pro Ala Leu
             20

<210> SEQ ID NO 893
<211> LENGTH: 22
<212> TYPE: PRT
<213> ORGANISM: Artificial Sequence
<220> FEATURE:
<223> OTHER INFORMATION: Hybrid antigen

<400> SEQUENCE: 893

Asn Leu Leu Arg Leu Thr Gly Trp Phe Phe Arg Lys Glu Leu Ala Gly
 1               5                  10                  15

Ile Gly Ile Leu Thr Val
             20

<210> SEQ ID NO 894
<211> LENGTH: 21
<212> TYPE: PRT
<213> ORGANISM: Artificial Sequence
<220> FEATURE:
<223> OTHER INFORMATION: Hybrid antigen

<400> SEQUENCE: 894

Asn Leu Leu Arg Leu Thr Gly Trp Phe Phe Arg Lys Ser Leu Leu Met
 1               5                  10                  15

Trp Ile Thr Gln Val
             20

<210> SEQ ID NO 895
<211> LENGTH: 21
<212> TYPE: PRT
<213> ORGANISM: Artificial Sequence
```

<220> FEATURE:
<223> OTHER INFORMATION: Hybrid antigen

<400> SEQUENCE: 895

Asn Leu Leu Arg Leu Thr Gly Trp Phe Phe Arg Lys Ser Val Tyr Asp
1               5                   10                  15

Phe Phe Val Trp Leu
            20

<210> SEQ ID NO 896
<211> LENGTH: 20
<212> TYPE: PRT
<213> ORGANISM: Artificial Sequence
<220> FEATURE:
<223> OTHER INFORMATION: Hybrid antigen

<400> SEQUENCE: 896

Gly Leu Tyr Asp Gly Met Glu His Leu Gly Ser Gly Asn Leu Leu Arg
1               5                   10                  15

Leu Thr Gly Trp
            20

<210> SEQ ID NO 897
<211> LENGTH: 20
<212> TYPE: PRT
<213> ORGANISM: Artificial Sequence
<220> FEATURE:
<223> OTHER INFORMATION: Hybrid antigen

<400> SEQUENCE: 897

Tyr Leu Glu Pro Gly Pro Val Thr Val Gly Ser Gly Asn Leu Leu Arg
1               5                   10                  15

Leu Thr Gly Trp
            20

<210> SEQ ID NO 898
<211> LENGTH: 20
<212> TYPE: PRT
<213> ORGANISM: Artificial Sequence
<220> FEATURE:
<223> OTHER INFORMATION: Hybrid antigen

<400> SEQUENCE: 898

Lys Ala Ser Glu Lys Ile Phe Tyr Val Gly Ser Gly Asn Leu Leu Arg
1               5                   10                  15

Leu Thr Gly Trp
            20

<210> SEQ ID NO 899
<211> LENGTH: 20
<212> TYPE: PRT
<213> ORGANISM: Artificial Sequence
<220> FEATURE:
<223> OTHER INFORMATION: Hybrid antigen

<400> SEQUENCE: 899

Asn Leu Leu Arg Leu Thr Gly Trp Phe Phe Arg Lys Ser Ser Trp Asp
1               5                   10                  15

Phe Ile Thr Val
            20

<210> SEQ ID NO 900
<211> LENGTH: 31
<212> TYPE: PRT

-continued

```
<213> ORGANISM: Artificial Sequence
<220> FEATURE:
<223> OTHER INFORMATION: Hybrid antigen

<400> SEQUENCE: 900

Asn Leu Leu Arg Leu Thr Gly Trp Phe Phe Arg Lys Ser Ile Ile Asn
 1               5                  10                  15
Phe Glu Lys Leu Phe Phe Arg Lys Arg Gly Tyr Val Tyr Gly Leu
            20                  25                  30

<210> SEQ ID NO 901
<211> LENGTH: 32
<212> TYPE: PRT
<213> ORGANISM: Artificial Sequence
<220> FEATURE:
<223> OTHER INFORMATION: Hybrid antigen

<400> SEQUENCE: 901

Asn Leu Leu Arg Leu Thr Gly Trp Phe Phe Arg Lys Arg Gly Tyr Val
 1               5                  10                  15
Tyr Gln Gly Leu Phe Phe Arg Lys Ser Ile Ile Asn Phe Glu Lys Leu
            20                  25                  30

<210> SEQ ID NO 902
<211> LENGTH: 32
<212> TYPE: PRT
<213> ORGANISM: Artificial Sequence
<220> FEATURE:
<223> OTHER INFORMATION: Hybrid antigen

<400> SEQUENCE: 902

Asn Leu Leu Arg Leu Thr Gly Trp Phe Phe Arg Lys Ser Ile Ile Asn
 1               5                  10                  15
Phe Glu Lys Leu Phe Phe Arg Lys Arg Gly Tyr Val Tyr Gln Gly Leu
            20                  25                  30

<210> SEQ ID NO 903
<211> LENGTH: 32
<212> TYPE: PRT
<213> ORGANISM: Artificial Sequence
<220> FEATURE:
<223> OTHER INFORMATION: Hybrid antigen

<400> SEQUENCE: 903

Asn Leu Leu Arg Leu Thr Gly Trp Phe Phe Arg Lys Arg Gly Tyr Val
 1               5                  10                  15
Tyr Gln Gly Leu Phe Phe Arg Lys Ser Ile Ile Asn Phe Glu Lys Leu
            20                  25                  30

<210> SEQ ID NO 904
<211> LENGTH: 8
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 904

Ile Ala Tyr Phe Tyr Pro Glu Leu
 1               5

<210> SEQ ID NO 905
<211> LENGTH: 32
<212> TYPE: PRT
<213> ORGANISM: Artificial Sequence
```

-continued

```
<220> FEATURE:
<223> OTHER INFORMATION: Hybrid antigen

<400> SEQUENCE: 905

Asn Leu Leu Arg Leu Thr Gly Trp Phe Phe Arg Lys Ser Ile Ile Asn
1               5                   10                  15

Phe Glu Lys Leu Phe Phe Arg Lys Arg Gly Tyr Val Tyr Gln Gly Leu
            20                  25                  30

<210> SEQ ID NO 906
<211> LENGTH: 8
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 906

Arg Thr Phe Ser Phe Gln Leu Ile
1               5

<210> SEQ ID NO 907
<211> LENGTH: 20
<212> TYPE: PRT
<213> ORGANISM: Artificial Sequence
<220> FEATURE:
<223> OTHER INFORMATION: Hybrid antigen

<400> SEQUENCE: 907

Asn Leu Leu Arg Leu Thr Gly Trp Phe Phe Arg Lys Arg Thr Phe Ser
1               5                   10                  15

Phe Gln Leu Ile
            20

<210> SEQ ID NO 908
<211> LENGTH: 16
<212> TYPE: PRT
<213> ORGANISM: Artificial Sequence
<220> FEATURE:
<223> OTHER INFORMATION: Hybrid antigen

<400> SEQUENCE: 908

Thr Glu Trp Thr Ser Ser Asn Val Met Glu Glu Arg Lys Ile Lys Val
1               5                   10                  15

<210> SEQ ID NO 909
<211> LENGTH: 28
<212> TYPE: PRT
<213> ORGANISM: Artificial Sequence
<220> FEATURE:
<223> OTHER INFORMATION: Hybrid antigen

<400> SEQUENCE: 909

Asn Leu Leu Arg Leu Thr Gly Trp Phe Phe Arg Lys Thr Glu Trp Thr
1               5                   10                  15

Ser Ser Asn Val Met Glu Glu Arg Lys Ile Lys Val
            20                  25

<210> SEQ ID NO 910
<211> LENGTH: 20
<212> TYPE: PRT
<213> ORGANISM: Artificial Sequence
<220> FEATURE:
<223> OTHER INFORMATION: Hybrid antigen

<400> SEQUENCE: 910
```

```
Asn Leu Leu Arg Leu Thr Gly Trp Phe Phe Arg Lys Asp Ala Pro Ile
1               5                   10                  15

Tyr Thr Asn Val
            20

<210> SEQ ID NO 911
<211> LENGTH: 20
<212> TYPE: PRT
<213> ORGANISM: Artificial Sequence
<220> FEATURE:
<223> OTHER INFORMATION: Hybrid antigen

<400> SEQUENCE: 911

Asn Leu Leu Arg Leu Thr Gly Trp Phe Phe Arg Lys Ser Ser Trp Asp
1               5                   10                  15

Phe Ile Thr Val
            20

<210> SEQ ID NO 912
<211> LENGTH: 20
<212> TYPE: PRT
<213> ORGANISM: Artificial Sequence
<220> FEATURE:
<223> OTHER INFORMATION: Hybrid antigen

<400> SEQUENCE: 912

Asn Leu Leu Arg Leu Thr Gly Trp Phe Phe Arg Lys Arg Thr Phe Ser
1               5                   10                  15

Phe Gln Leu Ile
            20

<210> SEQ ID NO 913
<211> LENGTH: 20
<212> TYPE: PRT
<213> ORGANISM: Artificial Sequence
<220> FEATURE:
<223> OTHER INFORMATION: Hybrid antigen

<400> SEQUENCE: 913

Asn Leu Leu Arg Leu Thr Gly Trp Phe Phe Arg Lys Ile Ala Tyr Phe
1               5                   10                  15

Tyr Pro Glu Leu
            20

<210> SEQ ID NO 914
<211> LENGTH: 8
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 914

Ser Ser Trp Asp Phe Ile Thr Val
1               5

<210> SEQ ID NO 915
<211> LENGTH: 8
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 915
```

```
Asp Ala Pro Ile Tyr Thr Asn Val
1               5
```

<210> SEQ ID NO 916
<211> LENGTH: 19
<212> TYPE: PRT
<213> ORGANISM: Artificial Sequence
<220> FEATURE:
<223> OTHER INFORMATION: Hybrid antigen

<400> SEQUENCE: 916

```
Asn Asn Phe Thr Val Ser Phe Trp Leu Arg Val Pro Lys Val Ser Ala
1               5                   10                  15

Ser His Leu
```

<210> SEQ ID NO 917
<211> LENGTH: 31
<212> TYPE: PRT
<213> ORGANISM: Artificial Sequence
<220> FEATURE:
<223> OTHER INFORMATION: Hybrid antigen

<400> SEQUENCE: 917

```
Asn Leu Leu Arg Leu Thr Gly Trp Phe Phe Arg Lys Asn Asn Phe Thr
1               5                   10                  15

Val Ser Phe Trp Leu Arg Val Pro Lys Val Ser Ala Ser His Leu
            20                  25                  30
```

<210> SEQ ID NO 918
<211> LENGTH: 13
<212> TYPE: PRT
<213> ORGANISM: Artificial Sequence
<220> FEATURE:
<223> OTHER INFORMATION: Hybrid antigen

<400> SEQUENCE: 918

```
Thr Pro Pro Ala Tyr Arg Pro Pro Asn Ala Pro Ile Leu
1               5                   10
```

<210> SEQ ID NO 919
<211> LENGTH: 31
<212> TYPE: PRT
<213> ORGANISM: Artificial Sequence
<220> FEATURE:
<223> OTHER INFORMATION: Hybrid antigen

<400> SEQUENCE: 919

```
His Trp Asp Phe Ala Trp Pro Trp Asn Gly Ser Gly Asn Asn Phe Thr
1               5                   10                  15

Val Ser Phe Trp Leu Arg Val Pro Lys Val Ser Ala Ser His Leu
            20                  25                  30
```

<210> SEQ ID NO 920
<211> LENGTH: 9
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 920

```
Ser Val Tyr Asp Phe Phe Val Trp Leu
1               5
```

```
<210> SEQ ID NO 921
<211> LENGTH: 9
<212> TYPE: PRT
<213> ORGANISM: Artificial Sequence
<220> FEATURE:
<223> OTHER INFORMATION: Heat shock-protein binding motif to form hybrid
      antigen

<400> SEQUENCE: 921

Val Ile Tyr Gln Tyr Met Asp Asp Leu
 1               5

<210> SEQ ID NO 922
<211> LENGTH: 21
<212> TYPE: PRT
<213> ORGANISM: Artificial Sequence
<220> FEATURE:
<223> OTHER INFORMATION: Hybrid antigen

<400> SEQUENCE: 922

Asn Leu Leu Arg Leu Thr Gly Trp Phe Phe Arg Lys Ile Leu Lys Glu
 1               5                  10                  15

Pro Val His Gly Val
            20

<210> SEQ ID NO 923
<211> LENGTH: 21
<212> TYPE: PRT
<213> ORGANISM: Artificial Sequence
<220> FEATURE:
<223> OTHER INFORMATION: Hybrid antigen

<400> SEQUENCE: 923

Asn Leu Leu Arg Leu Thr Gly Trp Phe Phe Arg Lys Val Ile Tyr Gln
 1               5                  10                  15

Tyr Met Asp Asp Leu
            20

<210> SEQ ID NO 924
<211> LENGTH: 21
<212> TYPE: PRT
<213> ORGANISM: Artificial Sequence
<220> FEATURE:
<223> OTHER INFORMATION: Hybrid antigen

<400> SEQUENCE: 924

Asn Leu Leu Arg Leu Thr Gly Trp Phe Phe Arg Lys Ser Leu Tyr Asn
 1               5                  10                  15

Thr Val Ala Thr Leu
            20

<210> SEQ ID NO 925
<211> LENGTH: 25
<212> TYPE: PRT
<213> ORGANISM: Artificial Sequence
<220> FEATURE:
<223> OTHER INFORMATION: Hybrid antigen

<400> SEQUENCE: 925

Asn Leu Leu Arg Leu Thr Gly Trp Phe Phe Arg Lys Thr Pro Pro Ala
 1               5                  10                  15

Tyr Arg Pro Pro Asn Ala Pro Ile Leu
            20                  25
```

-continued

```
<210> SEQ ID NO 926
<211> LENGTH: 30
<212> TYPE: PRT
<213> ORGANISM: Artificial Sequence
<220> FEATURE:
<223> OTHER INFORMATION: Hybrid antigen

<400> SEQUENCE: 926

Asn Asn Phe Thr Val Ser Phe Trp Leu Arg Val Pro Lys Val Ser Ala
1               5                   10                  15

Ser His Leu Gly Ser Gly Asn Leu Leu Arg Leu Thr Gly Trp
            20                  25                  30
```